US008071288B2

(12) United States Patent
Gold et al.

(10) Patent No.: US 8,071,288 B2
(45) Date of Patent: *Dec. 6, 2011

(54) METHODS AND REAGENTS FOR DETECTING TARGET BINDING BY NUCLEIC ACID LIGANDS

(75) Inventors: Larry Gold, Boulder, CO (US); Jonathan Drew Smith, Boulder, CO (US); Dominic Zichi, Boulder, CO (US); Daniel J. Schneider, Arvada, CO (US); Chad Greef, Louisville, CO (US)

(73) Assignee: SomaLogic, Inc., Boulder, CO (US)

( * ) Notice: Subject to any disclaimer, the term of this patent is extended or adjusted under 35 U.S.C. 154(b) by 491 days.

This patent is subject to a terminal disclaimer.

(21) Appl. No.: 12/030,024

(22) Filed: Feb. 12, 2008

(65) Prior Publication Data
US 2008/0160535 A1 Jul. 3, 2008

Related U.S. Application Data

(63) Continuation of application No. 10/504,696, filed as application No. PCT/US03/04142 on Feb. 10, 2003, now abandoned, and a continuation of application No. 10/114,187, filed on Apr. 1, 2002, now abandoned, application No. 12/030,024, which is a continuation-in-part of application No. 10/375,487, filed on Feb. 27, 2003, now Pat. No. 7,709,192, which is a continuation of application No. 09/581,465, filed as application No. PCT/US98/26515 on Dec. 14, 1998, now Pat. No. 6,544,776, which is a continuation of application No. 08/990,436, filed on Dec. 15, 1997, now Pat. No. 6,242,246.

(60) Provisional application No. 60/357,297, filed on Feb. 15, 2002, provisional application No. 60/398,666, filed on Jul. 26, 2002, provisional application No. 60/400,759, filed on Aug. 2, 2002.

(51) Int. Cl.
*C12Q 1/68* (2006.01)
*C07K 14/00* (2006.01)

(52) U.S. Cl. .......................................... 435/6; 530/350
(58) Field of Classification Search ... 435/6; 536/24.31, 536/24.32, 24.33
See application file for complete search history.

(56) References Cited

U.S. PATENT DOCUMENTS

| 4,098,876 | A | 7/1978 | Piasio et al. |
| 4,562,157 | A | 12/1985 | Lowe et al. |
| 4,587,044 | A | 5/1986 | Miller |
| 4,595,661 | A | 6/1986 | Cragle et al. |
| 4,737,453 | A | 4/1988 | Primus et al. |
| 4,743,542 | A | 5/1988 | Graham et al. |
| 4,752,566 | A | 6/1988 | Collins et al. |
| 5,035,996 | A | 7/1991 | Hartley |
| 5,124,246 | A | 6/1992 | Urdea et al. |
| 5,270,163 | A | 12/1993 | Gold et al. |
| 5,382,981 | A | 1/1995 | Inaba et al. |
| 5,412,087 | A | 5/1995 | McGall et al. |
| 5,432,099 | A | 7/1995 | Ekins et al. |
| 5,445,934 | A | 8/1995 | Fodor et al. |
| 5,475,096 | A | 12/1995 | Gold et al. |
| 5,476,766 | A | 12/1995 | Gold et al. |
| 5,510,270 | A | 4/1996 | Fodor et al. |
| 5,527,894 | A | 6/1996 | Gold et al. |
| 5,556,752 | A | 9/1996 | Lockhart et al. |
| 5,567,588 | A | 10/1996 | Gold et al. |
| 5,582,981 | A | 12/1996 | Toole et al. |
| 5,595,877 | A | 1/1997 | Gold et al. |
| 5,599,720 | A | 2/1997 | Ekins et al. |
| 5,605,662 | A | 2/1997 | Heller et al. |
| 5,624,711 | A | 4/1997 | Sundberg et al. |
| 5,639,868 | A | 6/1997 | Janjic et al. |
| 5,654,151 | A | 8/1997 | Allen et al. |
| 5,658,738 | A | 8/1997 | Nadeau et al. |
| 5,681,697 | A | 10/1997 | Urdea et al. |
| 5,688,935 | A | 11/1997 | Stephens et al. |
| 5,744,305 | A | 4/1998 | Fodor et al. |
| 5,756,291 | A | 5/1998 | Griffin et al. |
| 5,763,177 | A | 6/1998 | Gold et al. |
| 5,817,785 | A | 10/1998 | Gold et al. |
| 5,843,653 | A | 12/1998 | Gold et al. |
| 5,861,254 | A | 1/1999 | Schneider et al. |
| 5,874,218 | A | 2/1999 | Drolet et al. |

(Continued)

FOREIGN PATENT DOCUMENTS
GB    2 183 661    6/1987
(Continued)

OTHER PUBLICATIONS

Brody. The use of aptamers in large arrays for molecular diagnostics. Molecular Diagnostics, vol. 4(4), pp. 381-388, 1999.*

(Continued)

*Primary Examiner* — Prabha Chunduru
(74) *Attorney, Agent, or Firm* — Swanson & Bratschun, L.L.C.

(57) ABSTRACT

The present invention provides novel methods and reagents for detecting the binding of protein targets to nucleic acid ligands. Using Universal Protein Stains (UPS), proteins bound by nucleic acid ligands may be labeled with a detectable moiety. The methods and reagents are particularly useful for the detection of protein targets bound to multiplexed arrays of nucleic acid ligands. The present invention also provides novel methods for the multiplexed evaluation of photocrosslinking nucleic acid ligands. The methods allow one simultaneously to: (1) evaluate the performance (dynamic range) of a plurality of photocrosslinking nucleic acid ligands; and (2) assess the specificity of each photocrosslinking nucleic acid ligand for its cognate target protein. Photocrosslinking nucleic acid ligands with the most desirable properties can then be selected for use in diagnostic and prognostic medical assays. The present invention also provides a photocrosslinking nucleic acid ligand that binds specifically to HIV gp120MN.

34 Claims, 31 Drawing Sheets

U.S. PATENT DOCUMENTS

| | | | |
|---|---|---|---|
| 5,908,745 | A | 6/1999 | Mirzabekov et al. |
| 5,955,268 | A | 9/1999 | Granados et al. |
| 5,958,691 | A | 9/1999 | Pieken |
| 6,001,577 | A | 12/1999 | Gold et al. |
| 6,007,987 | A | 12/1999 | Cantor et al. |
| 6,037,137 | A | 3/2000 | Komoriya et al. |
| 6,140,098 | A | 10/2000 | Balasubramanian et al. |
| 6,184,042 | B1 | 2/2001 | Neumann et al. |
| 6,184,364 | B1 | 2/2001 | Pieken et al. |
| 6,207,446 | B1 | 3/2001 | Szostak et al. |
| 6,232,462 | B1 | 5/2001 | Collins et al. |
| 6,242,246 | B1 | 6/2001 | Gold et al. |
| 6,291,184 | B1 | 9/2001 | Gold et al. |
| 6,344,318 | B1 | 2/2002 | Gold et al. |
| 6,346,611 | B1 | 2/2002 | Pagratis et al. |
| 6,412,087 | B1 | 6/2002 | Matsumoto |
| 6,458,539 | B1 | 10/2002 | Gold et al. |
| 6,458,543 | B1 | 10/2002 | Gold et al. |
| 6,503,715 | B1 | 1/2003 | Gold et al. |
| 6,544,776 | B1 | 4/2003 | Gold et al. |
| 6,716,583 | B2 | 4/2004 | Gold et al. |
| 6,942,972 | B2 | 9/2005 | Farooqui et al. |
| 7,368,236 | B2 | 5/2008 | Gold et al. |
| 7,709,192 | B2 * | 5/2010 | Gold et al. .................... 435/6 |
| 7,855,054 | B2 | 12/2010 | Schneider et al. |
| 2002/0037506 | A1 | 3/2002 | Lin et al. |
| 2003/0162216 | A1 | 8/2003 | Gold et al. |
| 2003/0219801 | A1 | 11/2003 | Lipshutz |
| 2004/0209261 | A1 | 10/2004 | Keys et al. |
| 2004/0219526 | A1 | 11/2004 | Reddy et al. |
| 2004/0235053 | A1 | 11/2004 | Lam et al. |
| 2005/0142582 | A1 | 6/2005 | Doyle et al. |
| 2005/0227225 | A1 | 10/2005 | Krevolin |
| 2005/0250147 | A1 | 11/2005 | Macevicz |
| 2005/0288244 | A1 | 12/2005 | Manoharan et al. |
| 2006/0057573 | A1 | 3/2006 | Gold et al. |
| 2006/0105341 | A1 | 5/2006 | Krause et al. |
| 2007/0003950 | A1 | 1/2007 | Shen et al. |
| 2007/0161015 | A1 | 7/2007 | Zheng et al. |
| 2007/0166741 | A1 | 7/2007 | Heil et al. |
| 2007/0166742 | A1 | 7/2007 | Gold et al. |
| 2008/0160535 | A1 | 7/2008 | Gold et al. |
| 2009/0004667 | A1 | 1/2009 | Zichi et al. |
| 2010/0317120 | A1 | 12/2010 | Heil et al. |

FOREIGN PATENT DOCUMENTS

| | | |
|---|---|---|
| WO | WO 88/09810 | 12/1988 |
| WO | WO 92/14842 | 3/1992 |
| WO | WO 92/14843 | 9/1992 |
| WO | WO 93/04204 | 3/1993 |
| WO | WO 95/08003 | 3/1995 |
| WO | WO 95/18377 | 7/1995 |
| WO | WO 95/21265 | 8/1995 |
| WO | WO 96/06950 | 3/1996 |
| WO | WO 96/41019 | 12/1996 |
| WO | WO 99/31119 | 6/1999 |
| WO | WO 99/31275 | 6/1999 |
| WO | WO 99/31275 A1 * | 6/1999 |
| WO | WO 01/06249 | 1/2001 |
| WO | WO 02/06510 | 1/2002 |
| WO | WO 2005/108609 | 11/2005 |

OTHER PUBLICATIONS

Brody (1999) Molecular Diagnosis 4(4):381-388, The Use of Aptamers in Large Arrays for Molecular Diagnostics.

Drolet et al. (1996) Nature Biotechnology 14(8):1021-1025, An enzyme-linked oligonucleotide assay.

Gott et al. (1991) Biochemistry 30:6290-6295, A Specific, UV-Induced RNA-Protein Cross-Link Using 5-Bromouridine-Substitued RNA.

Ito et al. (1980) J. Am. Chem. Soc. 102:7535-7541, Acetone-Sensitized Photocoupling of 5-Bromouridine to Tryptophan Derivatives via Electro-Transfer Process.

Jayasena (1999) Clinical Chemistry 45(9):1628-1650, Aptamers: An Emerging Class of Molecules That Rival Antibodies in Diagnostics.

Jensen et al. (1995) Proc. Natl. Acad. Sci. USA 92:12220-12224,, Using in vitro selection to direct the covalent attachment of human immunodeficiency virus type 1 Rev protein to high-affinity RNA ligands.

Kleinjung et al. (1998) Analytical Chemistry 70:328-331, High-Affinity RNA as a Recognition Element in a Biosensor.

Lipshutz et al. (1995) Biotechniques 19(3):442-447, Using Oligonucleotide Probe Arrays to Access Genetic Diversity.

Scheller et al. (1997) Annals of the New York Academy of Sciences, Oct. 12, 1997, pp. 37-45, New Recognition Elements in Biosensing.

Szostak (1988) "Structure and Activity of Ribozymes" in Redesigning the Molecules of Life. (S.A. Benner ed.) Springer-Verlag Berlin Heidelberg, pp. 87-113.

Tuerk et al. (1990) Science 249-505, Systematic Evolution of Ligands by Exponential Enrichment: RNA Ligands to Bacteriophage T4 DNA Polymerase.

Jankolovits, J. (2008) J. Young Investigators 19(3):1-4, Studying pH Dependence of a Peptide Modification with an N-hydroxysuccinimide Ester Using Mass Spectroscopy.

Banks et al. (1995) Bioconjugate Chem 6:447-458, "Comparison of Three Common Amine Reactive Fluorescent Probes Used for Conjugation to Biomolecules by Capillary Zone Electrophoresis".

Ekins and Chu (Sep. 1997) JIFCC 9(3):100-109, Immunoassay and Other Ligand Assays: Present Status and Future Trends.

Krull et al. (Oct. 1997) J. Chromatology. B, 699:173-208, "Labeling reactions applicable to chromatography and electrophoresis of minute amounts of proteins".

McGown et al. (1995) Anal. Chem. 67:663A-668A, "The Nucleic Acid Ligand. A New Tool for Molecular Recognition".

Potyrailo et al. (Aug. 1998) Anal. Chem. 70:3419-3425, "Adapting Selected Nucleic Acid Ligands (Aptamers) to Biosensors".

Terpetschnig et al. (1994) Anal. Biochem. 217:197-204, "Synthesis of Squaraine-N-Hydroxysuccinimide Esters and Their Biological Application as Long-Wavelength Fluorescent Labels".

Bier and Fürste, (Feb. 1997) EXS 80:97-120, "Nucleic Acid based sensors".

Osborne et al. (1997) Current Opinion in Chemical Biology 1:5-9, "Aptamers as Therapeutic and Diagnostic Reagents: Problems and Prospects".

Abouzied (1994) Journal of the AOAC International 77(2):495-500, abstract only "Simultaneous screening of funomisin B1, aflatoxin B1, and zearaleone by line immunoblot: a computer-assisted multianalyte assay system".

Baldrich et al. (2004) Analytical Chemistry 76(23):7053-7063, "Aptasensor Development: Elucidation of Critical Parameters for Optimal Aptamer Performance".

Bock et al. (Mar. 2004) Proteomics 4(3):609-618, "Photoaptmaer arrays applied to multiplexed proteomic analysis".

Bock et al., (1992) Nature 355:564-565 "Selection of Single-Stranded DNA Molecules That Bind and Inhibit Human Thrombin".

DiDonato (2006) "Disseration. Part II. Synthesis and Evaluation of Modified Nucleotides for DNA Aptamer Selection" University of North Carolina, Raleigh 30-53.

Ellington & Szostak (1990) "Selection of RNAs with ligand-specific binding activity from pools of random sequence molecules" RNA Processing meeting abstract, p. 84.

EP Extended Search Report issued Dec. 9, 2010 in EP application serial No. 10176907.3.

Examination Report prepared Feb. 28, 2005 for European Patent Application No. 98963150.2.

Examination Report prepared Apr. 4, 2008 for European Patent Application No. 98963150.2.

Examination Report prepared Oct. 4, 2010 for European Patent Application No. 98963150.2.

Famulok and Szostak (1992) Angew. Chem. Int. Ed. Engl. 31(8): 979-988, "In Vitro Selection of Specific Ligand-binding Nucleic Acids".

Ferguson et al., (Dec. 1996) Nature Biotechnology, 14:1681-1684, "A fiber-optic DNA biosensor microarray for the analysis of gene expression".

Gold et al. (Jan. 1995) Annual Review of Biochemistry 64:763-797, "Diversity of Oligonucleotide Functions".

Hendrix (Apr. 23, 1977) Journal of the American Chemical Society, 119(16):3641-3648, "Direct observation of aminoglycoside-RNA internationcs by surface plasmon resonance."

International Search Report issued Apr. 13, 1999 for PCT International Patent Application No. PCT/US98/26515.

Joyce (1989) Gene 82:83-87, "Amplification, mutation and selection of catalytic RNA".

Joyce and Inoue (1989) Nucleic Acids Research 17(2): 711-722, "A novel technique for the rapid preparation of mutant RNAs".

Kinzler and Vogelstein (1989) Nucleic Acids Research 17(10): 3645-3653, "Whole genome PCR: application to the identification of sequences bound by gene regulatory proteins".

Kirby et al. (2004) Anal. Chem. 76(14):4066-4075, "Aptamer-Based Sensor Arrays for the Detection and Quantitation of Proteins".

Kramer et al. (1974) J. Mol. Biol. 89: 719-736, "Evolution in vitro: sequence and phenotype of a mutant RNA resistant to ethidium bromide".

Levisohn and Spiegleman (1968) PNAS USA 60: 866-872, "The cloning of a self-replicating RNA molecule".

Levisohn and Spiegleman (1969) PNAS USA 63: 805-811, "Further extracellular Darwinian experiments with replicating RNA moloecules: diverse variants isolated under different selective conditions".

Nelson et al. (Nov. 1, 1997) Amalystical Chemistry 69(21):4363-4368, "Surface plasmon resonance biomolecular interaction analysis".

Niemeyer et al. (Jan. 1, 1994) Nucleic Acid Research 22(25):4430-5539, "Oligonucleotide-Directed Self-Assembly of Proteins: Semisynthetic DNA-Streptavidin Hybrid Molecules as Connectors for the Generation of Macroscopic Arranys and the Construction of Supramolecular Bioconjugates".

Office Action issued Jan. 24, 2008 in U.S. Appl. No. 11/623,822.

Office Action issued Jun. 24, 2010 in U.S. Appl. No. 12/499,967.

Office Action issued Jun. 25, 2010 in U.S. Appl. No. 12/175,434.

Office Action (final) issued Sep. 11, 2008 in U.S. Appl. No. 11/623,822.

Office Action (non-final) issued Aug. 26, 1999 in U.S. Appl. No. 08/990,436 (U.S. Patent No. 6,242,246 B1).

Office Action (final) issued Jun. 7, 2000 in U.S. Appl. No. 08/990,436 (U.S. Patent No. 6,242,246 B1).

Office Action (non-final) issued May 9, 2005 in U.S. Appl. No. 10/375,487 (U.S. Patent No. 7,709,192 B2).

Office Action (final) issued Jan. 24, 2006 in U.S. Appl. No. 10/375,487 (U.S. Patent No. 7,709,192 B2).

Office Action (non-final) issued Oct. 16, 2006 in U.S. Appl. No. 10/375,487 (U.S. Patent No. 7,709,192 B2).

Office Action (final) issued Jun. 27, 2007 in U.S. Appl. No. 10/375,487 (U.S. Patent No. 7,709,192 B2).

Office Action (non-final) issued Feb. 6, 2008 in U.S. Appl. No. 10/375,487 (U.S. Patent No. 7,709,192 B2).

Office Action (final) issued Sep. 25, 2008 in U.S. Appl. No. 10/375,487 (U.S. Patent No. 7,709,192 B2).

Office Action (non-final) issued Apr. 9, 2009 in in U.S. Appl. No. 10/375,487 (U.S. Patent No. 7,709,192 B2).

Office Action (final) issued Nov. 5, 2009 in U.S. Appl. No. 10/375,487 (U.S. Patent No. 7,709,192 B2).

Office Action (non-final) issued Feb. 14, 2001 in U.S. Appl. No. 09/581,465 (U.S. Patent No. 6,544,776 B1).

Office Action (non-final) issued Aug. 22, 2001 in U.S. Appl. No. 09/581,465 (U.S. Patent No. 6,544,776 B1).

Office Action (final) issued Apr. 17, 2002 in U.S. Appl. No. 09/581,465 (U.S. Patent No. 6,544,776 B1).

Office Action (non-final) issued Aug. 23, 2001 in U.S. Appl. No. 09/723,394 (U.S. Patent No. 6,503,715 B1).

Office Action (non-final) issued Aug. 27, 2011 in U.S. Appl. No. 09/723,517 (U.S. Patent No. 6,458,543 B1).

Oliphant and Struhl (1987) Methods in Enzymology 155: 568-582, "The use of random-sequence oligonucleotides for determining consensus sequences".

Oliphant and Struhl (1988) Nucleic Acids Research 16(15): 7673-7683, "Defining the consensus sequences of E. coli promoter elements by random selection".

Oliphant et al. (1986) Gene 44:177-183, "Cloning of random-sequence oligodeoxynucleotides".

Oliphant et al. (Jul. 1989) Mol. Cell. Biol. 9: 2944-2949, "Defining the sequence specificity of DNA-binding proteins by selecting binding sites from random-sequence oligonucleotides: analysis of yeast GCN4 protein".

Robertson and Joyce (Mar. 1990) Nature 344: 467-468, "Selection in vitro of an RNA enzyme that specifically cleaves single-stranded DNA".

Supplementary European Search Report prepared Aug. 9, 2004 for European Patent Application No. 98963150.2.

Thiesen and Bach (Jun. 1990) Nucleic Acids Res. 18(11): 3203-3209, "Target detection assay (TDA): a versatile procedure to determine DNA binding sites as demonstrated on SP1 protein".

Uddin, A.H. et al. (1997) Nucleic Acids Research 25(20):4139-4146, "A fiber optic biosensor for fluorimetric detection of triple-helical DNA".

Willis (1993) Science 262:1255-1257, "Photocrosslinking of 5-Iodouracil-Substituted RNA and DNA to Proteins".

Written Opinion issued Oct. 20, 1999 for PCT International Patent Application No. PCT/US98/26515.

Zichi et al. (Mar. 7, 2008) Current Opinion in Chemical Biology 12(1):78-85, "Proteomics and diagnostics: Let's Get Specific, again".

\* cited by examiner

FIGURE 3

Photocrosslinking Nucleic Acid Ligand Sequences

| PROTEIN | REF. NO. | SEQUENCE | SEQ. ID. NO: |
|---|---|---|---|
| α2-antiplasmin bp | N-28.13 | amino-C6-GGG AGG ACG ATG CGG GGU CAC CUU AAC CAC AUG ACC AGU CUA UGC CAG ACG ACG AGC GGG | 1 |
| α2-antiplasmin bp | N-28.16 | amino-C6-GGG AGG ACG ATG CGG GCG GGA GCA GUC UAU GUC AUC UGU CCA CCU CCA GAC GAC GAG CGG G | 2 |
| α2-antiplasmin bp | N-28.17 | amino-C6-GGG AGG ACG ATG CGG CCG GGA GUU AAA CAC UCA GUC UAU GCG CCC CAG ACG ACG AGC GGG | 3 |
| α2-antiplasmin bp | N-28.2 | amino-C6-GGG AGG ACG ATG CGG GCC CCA CGG CAG UCU AUG UCA UCA ACC CCC CAG ACG ACG AGC GGG | 4 |
| α2-antiplasmin bp | N-28.32 | amino-C6-GGG AGG ACG ATG CGG GCC CAC UUU CUA CAG GGC AGU CUA UGU CAU CAG ACG ACG AGC GGG | 5 |
| Angiogenin | N-11.11 | amino-C6-GGG AGG ACG ATG CGG GCC AAC CAC GUG GUA UUA UUG ACC UUG CAA UGG GAA UGC CCA GAC GAC GAG CGG G | 6 |
| Angiogenin | N-11.12 | amino-C6-GGG AGG ACG ATG CGG GGC AAA CUG CGU CGU AUU AUA AGC CUC GCU ACA GAU GCC ACA GAC GAC GAG CGG G | 7 |
| Angiogenin | N-11.14 | amino-C6-GGG AGG ACG ATG CGG GCA CCU ACC UGA GCU ACA UAU GAC AGU GUC ACC CUG GCC CCA GAC GAC GAG CGG G | 8 |
| Angiogenin | N-11.16 | amino-C6-GGG AGG ACG ATG CGG GCC AAA UGG ACU UUU CGC CAC GAA CUU ACG ACG GUG UUG CCA GAC GAC GAG CGG G | 9 |
| Angiogenin | N-11.27 | amino-C6-GGG AGG ACG ATG CGG CAC CAA AAG GUG GUC UUA GCC UAA UUA UGG ACG UGU CCA CCA GAC GAC GAG CGG G | 10 |
| Angiogenin | N-11.58 | amino-C6-GGG AGG ACG ATG CGG GCC ACG UGU AUU AUC CUC AGC UUA UAG CCA UGG CAU GGA CCA GAC GAC GAG CGG G | 11 |
| Angiogenin | N-11.85 | amino-C6-GGG AGG ACG ATG CnG GCC CUA CUU GCA UGA AUA UCC ACU CCU AGG CUU GAG GGA GCA GAC GAC GAG CGG G | 12 |

| | | | |
|---|---|---|---|
| Angiogenin | N-11.59 | amino-C6-GGG AGG ACG AUG CGG GCA AAG UCU UGG UCC ACC AAA UAU GUG AUG UCA CCA CCA GCA GAC GAC GAG CGG G | 13 |
| Angiogenin | Ac-11.59 | Ac-GGG AGG ACG AUG CGG GCA AAG UCU UGG UCC ACC AAA UAU GUG AUG UCA CCA CCA GCA GAC GAC GAG CGG G | 14 |
| bFGF | 6.7 | GGG AGG ACG AUG CGG GCG AAG GCA CAC CGA GUU CAU AGU AUC CCA CAG ACG ACG AGC GGG A | 15 |
| bFGF | N-6.7 | amino-C6-GGG AGG ACG AUG CGG GCG AAG GCA CAC CGA GUU CAU AGU AUC CCA CAG ACG ACG AGC GGG A | 16 |
| bFGF | N-HEG-6.7 | amino-C18-GGG AGG ACG AUG CGG GCG AAG GCA CAC CGA GUU CAU AGU AUC CCA CAG ACG ACG AGC GGG A | 17 |
| bFGF | B-6.7 | biotin-GGG AGG ACG AUG CGG GCG AAG GCA CAC CGA GUU CAU AGU AUC CCA CAG ACG ACG AGC GGG A | 18 |
| bFGF | N-6.40 | amino-C6-GGG AGG ACG AUG CGG UGA CGU AAG AGU GUA AUC GAU GCA GCC UGG CAG ACG ACG AGC GGG A | 19 |
| bFGF | S-6.7 | thiol-C6-GGG AGG ACG AUG CGG GCG AAG GCA CAC CGA GUU CAU AGU AUC CCA CAG ACG ACG AGC GGG A | 20 |
| bFGF | Ac-6.7 | Ac-GGG AGG ACG AUG CGG GCG AAG GCA CAC CGA GUU CAU AGU AUC CCA CAG ACG ACG AGC GGG | 21 |
| bNGF | N-13.7 | amino-C6-GGG AGG ACG AUG CGG GAC CAA UAA CAC UAC ACU GAU CAU CUC CCU UCU AUG UCC CCA GAC GAC GAG CGG G | 22 |
| bNGF | N-13.17 | amino-C6-GGG AGG ACG AUG CGG GCA CAC UUA AAU CCA CUU CAC CUU ACA AUU CCU UUA UCU GCA GAC GAC GAG CGG G | 23 |
| bNGF | N-13.43 | amino-C6-GGG AGG ACG AUG CGG CCA UAC GCA CUU CAG UGG GGA UAA UCC AAC UGG UUU GGU GCA GAC GAC GAG CGG G | 24 |
| bNGF | N-13.44 | amino-C6-GGG AGG ACG AUG CGG GAC CAA AUA CCA ACU UCA CAU CAC CUU UCU UAU UCU CCG GCA GAC GAC GAG CGG G | 25 |
| bNGF | N-13.65 | amino-C6-GGG AGG ACG AUG CGG GCA CUA ACU UUA CCU CCA CCU CUA ACC ACC CUC CUU UCU GCA GAC GAC GAG CGG G | 26 |

FIGURE 3 (continued)

| | | | |
|---|---|---|---|
| bNGF | N-13.78 | amino-C6-GGG AGG ACG ATG CGG GCC CCA AAC ACU UGU UCC UAU CUU UCA ACC CCC CUU GAU CCA GAC GAC GAG CGG G | 27 |
| bNGF | Ac-13.17 | Ac-GGG AGG ACG ATG CGG GCA CAC UUA AAU CCA CUU CAC CUU ACA AUU CCU UUA UCU GCA GAC GAC GAG CGG G | 28 |
| C1s f | N-31.56 | amino-C6-GGG AGG ACG ATG CGG GCA CAA GCC CAA CCU UUC CUA GAU CUU CCC CAG ACG ACG AGC GGG | 29 |
| C1s f | N-31.62 | amino-C6-GGG AGG ACG ATG CGG CAC CAA CCU AGA AGA GCC AAC CUA GCU GUC CAG ACG ACG AGC GGG | 30 |
| C1s f | N-31.65 | amino-C6-GGG AGG ACG ATG CGG GCA GUA AUC ACC UCG UUG AAC CAG ACC CUU CGU UUA UUG CCA GAC GAC GAG CGG G | 31 |
| C1s f | N-31.73 | amino-C6-GGG AGG ACG ATG CGG CAA CCC CCU UAC UAC ACC UUC UCC AAC UUG AUC ACU CUG CCA GAC GAC GAG CGG G | 32 |
| Calpastatin bp | N-32.17 | amino-C6-GGG AGG ACG ATG CGG GCU ACG UAC AAC GUC CAC UCU ACC UCC GUC CAG ACG ACG AGC GGG | 33 |
| Calpastatin bp | N-32.23 | amino-C6-GGG AGG ACG ATG CGG CAU GCA GUA GGU GCU UAA ACC CUC AGU AGU CAG ACG ACG AGC GGG | 34 |
| Catalase f | N-33.56 | amino-C6-GGG AGG ACG ATG CGG nAC CAC AGG UUC AUU CCA ACA GCU UCU GGC CGA UCU UUA GCA GAC GAC GAG CGG G | 35 |
| Catalase f | N-33.76 | amino-C6-GGG AGG ACG ATG CGG CCA CUA CAC CUC ACU AGG CUU CCU ACC CUC CAG ACG ACG AGC GGG | 36 |
| Catalase f | N-33.77 | amino-C6-GGG AGG ACG ATG CGG CAA GCA GUA AAG GAU CAG GAC CAC CUU AGG CAG ACG ACG AGC GGG | 37 |
| Catalase f | N-33.79 | amino-C6-GGG AGG ACG ATG CGG CCA CAC GAU CUC CUU CAC CCU CCU GUC CCU ACU AGA GCA UCA GAC GAC GAG CGG G | 38 |
| Catalase f | N-33.88 | amino-C6-GGG AGG ACG ATG CGG CAC ACC CUA CCC UUA ACC UCA CCU GUC CCU ACU AGA GCA UCA GAC GAC GAG CGG G | 39 |

FIGURE 3 (continued)

| | | | |
|---|---|---|---|
| C-Reactive Protein | N-71.25 | amino-C6-GGG AGG ACG ATG CGG GGU CAC CUU CGU UUG CUU GCU GCU CCC CCC CAG ACG ACG AGC GGG | 40 |
| C-Reactive Protein | Ac-71.25 | Ac GGG AGG ACG ATG CGG GGU CAC CUU CGU UUG CUU GCU GCU CCC CCC CAG ACG ACG AGC GGG | 41 |
| Elastase | Elas43 | GGG AGG ACG ATG CGG CAA CCC ACC ACU CUA UCU UUC CCA UAA CUG CAG ACG ACG AGC GGG A | 42 |
| Elastase | N-Elas43 | amino-C6-GGG AGG ACG ATG CGG CAA CCC ACC ACU CUA UCU UUC CCA UAA CUG CAG ACG ACG AGC GGG A | 43 |
| Elastase | B-2.43 | biotin-GGG AGG ACG ATG CGG CAA CCC ACC ACU CUA UCU UUC CCA UAA CUG CAG ACG ACG AGC GGG A | 44 |
| Elastase | N-34.15 | amino-C6-GGG AGG ACG ATG CGG GAC GGA CCU ACC UUU UCG CAA CUA CUG GUG CAG ACG ACG AGC GGG | 45 |
| Elastase | N-34.17 | amino-C6-GGG AGG ACG ATG CGG CAC AGC GAG GGU UGG GCU UUU CUC AAU UUC CAG ACG ACG AGC GGG | 46 |
| Elastase | N-34.5 | amino-C6-GGG AGG ACG ATG CGG GCU GCG GCU ACC GUU UCC UUA CCG ACU GGG CAG ACG ACG AGC GGG | 47 |
| Elastase | N-34.8 | amino-C6-GGG AGG ACG ATG CGG GAA CAC UUG UCG AUA GUC UUG GUU AAG CUG CAG ACG ACG AGC GGG | 48 |
| Endostatin | N-92.4 | amino-C6-GGG AGG ACG ATG CGG CAC AAU GAA GUC ACU CUU GAC GCU UGU AUU CAG ACG ACG AGC GGG | 49 |
| Endostatin | Ac-92.4 | Ac-GGG AGG ACG ATG CGG CAC AAU GAA GUC ACU CUU GAC GCU UGU AUU CAG ACG ACG AGC GGG | 50 |
| Ferritin f | N-36.51 | amino-C6-GGG AGG ACG ATG CGG GCG GAC UUG ACG GUG UCU UGC GAA GCU CCU ACU UUA CCU ACA GAC GAC GAG CGG G | 51 |
| Ferritin f | N-36.53 | amino-C6-GGG AGG ACG ATG CGG GCA GUU AGC GAU AGC CUU UCC AAG UCC UUG UGA CGU UGC CCA GAC GAC GAG CGG G | 52 |
| GP120MN | SL0518 | GGG AGG ACG ATG CGG AAU GCG CGA GCU UCC GAA AAG GAA AUU ACG CAG ACG ACG AGC GGG A | 53 |

FIGURE 3 (continued)

| | | | |
|---|---|---|---|
| GP120MN | N-3.7 | amino-C6-GGG AGG ACG ATG CGG AAU GCG CGA GCU UCC GAA AAG GAA AUU ACG CAG ACG ACG AGC GGG A | 54 |
| GP120MN | S-3.7 | thiol-C6-GGG AGG ACG ATG CGG AAU GCG CGA GCU UCC GAA AAG GAA AUU ACG CAG ACG ACG AGC GGG A | 55 |
| GP120MN | N-3.5 | amino-C6-GGG AGG ACG ATG CGG CAA CCA CAC GCA GGA GGA CAC AAC GAU CCG CAG ACG ACG AGC GGG | 56 |
| GP120MN | N-3.54 | amino-C6-GGG AGG ACG ATG CGG GCG AAG GCA CAC CGA GUU CAU AGU AUC CCA CAG ACG ACG AGC GGG | 57 |
| GP120MN | N-3.76 | amino-C6-GGG AGG ACG ATG CGG GAC GAG GGA CCA GAC CGC CAC AGC GGG AUG CAG ACG ACG AGC GGG | 58 |
| GP120MN | N-7.3 | amino-C6-GGG AGG ACG ATG CGG GAG GAC CAC GAC CAU GAC CCA CCA GGA AUG CAG ACG ACG AGC GGG | 59 |
| GP120MN | N-7.4 | amino-C6-GGG AGG ACG ATG CGG GCA CAG GCC UAA CAU ACC UCC AUC UCC UGG CAG ACG ACG AGC GGG | 60 |
| GP120MN | N-7.11 | amino-C6-GGG AGG ACG ATG CGG GAC CAA CGA GAC CAC ACG ACA AGC GCU GUG CAG ACG ACG AGC GGG | 61 |
| GP120MN | N-7.20 | amino-C6-GGG AGG ACG ATG CGG GCC AUG GAU GGU UUG GUU GGC UGU CCU CAG ACG ACG AGC GGG | 62 |
| GP120MN | N-HEG-3.7 | Sp18 GGG AGG ACG ATG CGG AAU GCG CGA GCU UCC GAA AAG GAA AUU ACG CAG ACG ACG AGC GGG A | 63 |
| IGFBP-3 | N-112.65 | amino-C6-GGG AGG ACG ATG CGG GCA AAG UGU UAU UUC UUG AUC UGU UUC ACC CAG ACG ACG AGC GGG | 64 |
| IGFBP-3 | Ac-112.65 | Ac-GGG AGG ACG ATG CGG GCA AAG UGU UAU UUC UUG AUC UGU UUC ACC CAG ACG ACG AGC GGG | 65 |
| IL-2 bc | N-39.56 | amino-C6-GGG AGG ACG ATG CGG CCA CCA UGU CAC CUC AAU UAC CCU UCC UCC CAG ACG ACG AGC GGG | 66 |
| IL-2 bc | N-39.61 | amino-C6-GGG AGG ACG ATG CGG CCA ACC CUC ACU CCU UCU UCA CUU CAC CUC CAG ACG ACG AGC GGG | 67 |

FIGURE 3 (continued)

| | | | |
|---|---|---|---|
| IL-2 bp | N-38.22 | amino-C6-GGG AGG ACG ATG CGG GCA CAA CUC CCA CCA CCC UUC UUU CAA CUC CCU ACU GCC CCA GAC GAC GAG CGG G | 68 |
| IL-2 bp | N-38.26 | amino-C6-GGG AGG ACG ATG CGG GCA GAC AGU GUG GGG UUU AGU GUC CAU GGC CAG ACG ACG AGC GGG | 69 |
| IL-2 bp | N-38.27 | amino-C6-GGG AGG ACG ATG CGG GCA CAC UCU UCA CCC CCU CCU UUU AGC UGC CAG ACG ACG AGC GGG | 70 |
| IL-2 bp | N-38.37 | amino-C6-GGG AGG ACG ATG CGG GAC CUC CGG GUA ACC AGG UAA CUC CUA GCC AGA CGA CGA GCG GG | 71 |
| IL-2 bp | N-38.38 | amino-C6-GGG AGG ACG ATG CGG CCA CCU ACC UCU ACA CUA CCU UAC CUA CUC CAG ACG ACG AGC GGG | 72 |
| IL-2 bp | N-38.47 | amino-C6-GGG AGG ACG ATG CGG GCA GGC AAC CUU ACC AAG AUG CCC CUC CUG CAG ACG ACG AGC GGG | 73 |
| IL-2 bp | N-38.6 | amino-C6-GGG AGG ACG ATG CGG CAC ACC CCU CAA CUU ACC CUA CUU CUU GGC CAG ACG ACG AGC GGG | 74 |
| IL-4 | B-12.48 | biotin-GGG AGG ACG ATG CGG CCC CGA GUU UCC CUA AGG UUU GGU UGA CCU GUC AUU UCA GCA GAC GAC GAG CGG G | 75 |
| IL-4 | N-12.48 | amino-C6-GGG AGG ACG ATG CGG CCC CGA GUU UCC CUA AGG UUU GGU UGA CCU GUC AUU UCA GCA GAC GAC GAG CGG G | 76 |
| IL-4 | N-12.8 | amino-C6-GGG AGG ACG ATG CGG GCC GAA GUC UAA ACC UGC UCG UGA CUU UCU UUC GAU GUU GCA GAC GAC GAG CGG G | 77 |
| IL-4 | N-12.13 | amino-C6-GGG AGG ACG ATG CGG GCC UAC CAA CUC CCC UCU AGU CCU GUU CUA UCC ACG UUG GCA GAC GAC GAG CGG G | 78 |
| IL-4 | N-12.41 | amino-C6-GGG AGG ACG ATG CGG GCC AAG GUU CCC UUC UGC CUC AUU GUG UGG GAC CAU CCA GAC GAC GAG CGG G | 79 |
| IL-4 | N-12.63 | amino-C6-GGG AGG ACG ATG CGG GCA CAG GUU CUA UCA ACG UUG UCC UGA GUA AUU GAC CUG CAG ACG ACG AGC GGG | 80 |

FIGURE 3 (continued)

| | | | |
|---|---|---|---|
| IL-4 | N-12.78 | amino-C6-GGG AGG ACG ATG CGG GCC AAG GAC AUU CUU GUU CGU UGU UGC UGU CCA CUG UCU CCA GAC GAC GAG CGG G | 81 |
| IL-4 | Ac-12.48 | Ac-GGG AGG ACG ATG CGG CCC CGA GUU UCC CUA AGG UUU GGU UGA CCU GUC AUU UCA GCA GAC GAC GAG CGG G | 82 |
| IL-4 bc | N-41.49 | amino-C6-GGG AGG ACG ATG CGG CAC ACG GUU GCC AUA CCC UUC AUU AUU GAG CAG ACG ACG AGC GGG | 83 |
| IL-4 bc | N-41.50 | amino-C6-GGG AGG ACG ATG CGG CCG GCU GCU UCC CCC CUG GUC AUU GUU GUG CAG ACG ACG AGC GGG | 84 |
| IL-4 bc | N-41.56 | amino-C6-GGG AGG ACG ATG CGG GCC AAA GUU CCC AUC CAC GUU ACU CUU UGC CAG ACG ACG AGC GGG | 85 |
| IL-4 bc | N-41.76 | amino-C6-GGG AGG ACG ATG CGG GCC AAG GUU CCC UUC UGC CUC AUU GUU GUG CAG ACG ACG AGC GGG | 86 |
| IL-4 bp | N-40.2 | amino-C6-GGG AGG ACG ATG CGG GCA CCU UCU AUC GAC GUU GCG GUA CCC AUG CAG ACG ACG AGC GGG | 87 |
| IL-4 bp | N-40.3 | amino-C6-GGG AGG ACG ATG CGG GCG GAU CCC AGC GCG GCU AAC GUU UGG GGG CAG ACG ACG AGC GGG | 88 |
| IL-4 bp | N-40.5 | amino-C6-GGG AGG ACG ATG CGG GAG GCG GAU CCU AAC GUU GAU UUG GUG UGC CAG ACG ACG AGC GGG | 89 |
| IL-7 f | N-42.10 | amino-C6-GGG AGG ACG ATG CGG CAA CUA CCG GCU GGG GAC CUG AAC UUC AUA UCC CCU UCC CCA GAC GAC GAG CGG G | 90 |
| IL-7 f | N-42.22 | amino-C6-GGG AGG ACG ATG CGG GCA CCA GAA CCU GAC CUU AAU GCC CCC UUU CUC AGC UAA GCA GAC GAC GAG CGG G | 91 |
| IL-7 f | N-42.27 | amino-C6-GGG AGG ACG ATG CGG GCA GGA CGG ACG GGU GAG CUU CCC UGA UUU AAC UCU ACC ACA GAC GAC GAG CGG G | 92 |
| IL-7 f | N-42.3 | amino-C6-GGG AGG ACG ATG CGG GCC ACC UGA AUC CCU ACG UUG AUA GGA GUA UCC CCU UGC CCA GAC GAC GAG CGG G | 93 |

FIGURE 3 (continued)

| | | | |
|---|---|---|---|
| IL-7 f | N-42.5 | amino-C6-GGG AGG ACG ATG CGG GCU GAA AGG AAA CGG ACG AUU GAG CUU CCC CUU ACC UCU CCA GAC GAC GAG CGG G | 94 |
| Kininogen, 2-chain bc | N-46.13 | amino-C6-GGG AGG ACG ATG CGG GAC GCU AGU ACC CUG GCU GGC UUG GUU GGG CAG ACG ACG AGC GGG | 95 |
| Kininogen, 2-chain bc | N-46.35 | amino-C6-GGG AGG ACG ATG CGG GCA CGC ACU ACA GGU UGG UUU GGU UGG ACU UUC CGC ACA GAC GAC GAG CGG G | 96 |
| Kininogen, 2-chain f | N-43.50 | amino-C6-GGG AGG ACG ATG CGG CAC AAA CCG AGC UCU GUC CAG UCU AUC UUC ACA UCU UCC CCA GAC GAC GAG CGG G | 97 |
| Kininogen, 2-chain f | N-43.57 | amino-C6-GGG AGG ACG ATG CGG CCU GGA UUC AAU AAC CGG CAC UCC CCU UAC CUC AUG GGU CCA GAC GAC GAG CGG G | 98 |
| Kininogen, 2-chain f | N-43.60 | amino-C6-GGG AGG ACG ATG CGG GAC CAC UUU AAC CUU CCU UUC UCA UUU CCA CCC CCC UCC CCA GAC GAC GAG CGG G | 99 |
| PDGF | N-4.24 | amino-C6-GGG AGG ACG ATG CGG GCG GAA GAG GCA GGG UAC CAC GGC AGA GGU CAG ACG ACG AGC GGG | 100 |
| PDGF | N-4.87 | amino-C6-GGG AGG ACG ATG CGG GCC AAC CCC UAG UGA ACA ACA ACA CUC CCA CAG ACG ACG AGC GGG | 101 |
| PDGF | N-8.26 | amino-C6-GGG AGG ACG ATG CGG CAG CAC CGA GGU ACC CAA CAG GGA UCC GCC CAG ACG ACG AGC GGG | 102 |
| PDGF | N-8.27 | amino-C6-GGG AGG ACG ATG CGG GCG GCA GAC GCG CCG GGU ACC CCA GGU CCC CAG ACG ACG AGC GGG | 103 |
| PDGF | N-8.31 | amino-C6-GGG AGG ACG ATG CGG CAC AAG GAA CAA AGC GGC CCC UAU CCC CAA CAG ACG ACG AGC GGG | 104 |
| PDGF | N-8.33 | amino-C6-GGG AGG ACG ATG CGG GGG GCA AGA AGC ACG GUA CCC CAG GUC CGC CAG ACG ACG AGC GGG | 105 |
| PDGF | N-8.35 | amino-C6-GGG AGG ACG ATG CGG CCG GAC AUC CCC CAG GGC AAA ACC AAC UCC CAG ACG ACG AGC GGG | 106 |

FIGURE 3 (continued)

| | | | |
|---|---|---|---|
| PDGF | N-8.37 | amino-C6-GGG AGG ACG ATG CGG CAA GGG AAA CAG AUA GCC CAG GCU CCC CCC CAG ACG ACG AGC GGG | 107 |
| Plasmin f | N-50.25 | amino-C6-GGG AGG ACG ATG CGG CAA CCC UGA CAC CAC GUU GUU UCU CCU UUU GGG GUA ACC GCA GAC GAG CGG G | 108 |
| Plasmin f | Ac-50.25 | Ac-GGG AGG ACG ATG CGG CAA CCC UGA CAC CAC GUU GUU UCU CCU UUU GGG GUA ACC GCA GAC GAG CGG G | 109 |
| P-Selectin | N-14.14 | amino-C6-GGG AGG ACG ATG CGG CGC CCC GAU UGA CCU UCG AUU UAU CCU ACU UAU GGC ACC CCA GAC GAC GAG CGG G | 110 |
| P-Selectin | N-14.21 | amino-C6-GGG AGG ACG ATG CGG CAC GAG GGA AUC ACC UCG AAC UUG UCC UGG AUU ACU GCC CAG ACG ACG AGC GGG | 111 |
| P-Selectin | N-14.17 | amino-C6-GGG AGG ACG ATG CGG CCA UGA ACC CAU CCU CUG GUU CAU AAU CGA CGU GUU CGU GCA GAC GAC GAG CGG G | 112 |
| P-Selectin | N-14.24 | amino-C6-GGG AGG ACG ATG CGG GCU CAA UAA CCU GAA UCU ACC UUU CCC UAG CAA AGG UCU GCA GAC GAC GAG CGG G | 113 |
| P-Selectin | N-14.95 | amino-C6-GGG AGG ACG ATG CGG CCA UAC GCA CUU CAG UGG GGA UAA UCC AAC UGG UUU GGU GCA GAC GAC GAG CGG G | 114 |
| Serum Amyloid Protein f | N-51.50 | amino-C6-GGG AGG ACG ATG CGG GCC GAC UCU GAG GAA AAG GUU UUA UGU AUG GCU ACC CCU GCA GAC GAC GAG CGG G | 115 |
| Serum Amyloid Protein f | Ac-51.50 | Ac-GGG AGG ACG ATG CGG GCC GAC UCU GAG GAA AAG GUU UUA UGU AUG GCU ACC CCU GCA GAC GAC GAG CGG G | 116 |
| TGFb | N-15.74 | amino-C6-GGG AGG ACG ATG CGG GCA CAA CCU UAC CAC CCU AGC CUA CCC CUA ACC UCC UGU CCA GAC GAC GAG CGG G | 117 |
| TGFb | N-15.81 | amino-C6-GGG AGG ACG ATG CGG GAC CAU CCA AUA CCU UCC GUA ACA CUU UCC UUC UUC CUU CCA GAC GAC GAG CGG G | 118 |
| TGFb | N-15.82 | amino-C6-GGG AGG ACG ATG CGG GCA GCA ACC UAC CUU ACC UUC CCC UAG CCU ACC UUA UCC CCA GAC GAC GAG CGG G | 119 |

FIGURE 3 (continued)

| | | | |
|---|---|---|---|
| TGFb | N-15.83 | amino-C6-GGG AGG ACG ATG CGG GCA CCU UUC UUA CAU CUU GGC UUC AUU CUU GCA CCA UUG GCA GAC GAC GAG CGG G | 120 |
| TGFb | N-15.87 | amino-C6-GGG AGG ACG ATG CGG GCA CAA UCA AGA CCU CUC CAA ACU UGA ACU CUG UCU AUC CCA GAC GAC GAG CGG G | 121 |
| Thrombin | Thro4 | GGG AGG ACG ATG CGG GCA GUA GGU UGG GUA GGG UGG UCU GCU CAG ACG ACG AGC GGG A | 122 |
| Thrombin | N-5.4 | amino-C6-GGG AGG ACG ATG CGG GCA GUA GGU UGG GUA GGG UGG UCU GCU CAG ACG ACG AGC GGG A | 123 |
| Thrombin | B-5.4 | biotin-GGG AGG ACG ATG CGG GCA GUA GGU UGG GUA GGG UGG UCU GCU CAG ACG ACG AGC GGG A | 124 |
| Thrombin | B-5.75 | biotin-GGG AGG ACG ATG CGG GCA GGA CGG ACA GCA AGG GGU GAG CAC GAG CAG ACG ACG AGC GGG | 125 |
| Thrombin | N-5.51 | amino-C6-GGG AGG ACG ATG CGG GAG GAG CUG AUG GGU GGU GAG GUU GGC CAG ACG ACG AGC GGG | 126 |
| Thrombin | N-5.75 | amino-C6-GGG AGG ACG ATG CGG GCA GGA CGG ACA GCA AGG GGU GAG CAC GAG CAG ACG ACG AGC GGG | 127 |
| Thrombin | N-5.77 | amino-C6-GGG AGG ACG ATG CGG GCG GUU GGC GUG GUU GGA AAU GUC CCG UCA GAC GAC GAG CGG G | 128 |
| Thrombin | Ac-5.4 | Ac-GGG AGG ACG ATG CGG GCA GUA GGU UGG GUA GGG UGG UCU GCU CAG ACG ACG AGC GGG | 129 |
| VEGF | N-60.78 | amino-C6-GGG AGG ACG ATG CGG GCA GGA GUC CAC UUU CAC UCC ACC UAC CGG AAU GUU ACC CCA GAC GAC GAG CGG G | 130 |
| VEGF | N-60.87 | amino-C6-GGG AGG ACG ATG CGG CCC UCC CGA CCA CAC CUC CUA UCC UGU CCC UAC UAG AGC AUC AGA CGA CGA GCG GG | 131 |
| VEGF | N-60.61 | amino-C6-GGG AGG ACG ATG CGG CAA GGU ACU ACU CCU AAC CUU AUC CCU UCC UCU UUG CCA GAC GAC GAG CGG G | 132 |
| VEGF | N-60.52 | amino-C6-GGG AGG ACG ATG CGG CAU CAA AAC UGG GGG CGA GUG AUU UAU GUU AGG GGC CUG GCC AGA CGA CGA GCG GG | 133 |

FIGURE 3 (continued)

| | | | |
|---|---|---|---|
| tPA | N-56.2 | amino-C6-GGG AGG ACG ATG CGG GCU GGG AAC AUC CCU CUU GUC UUG CUU ACC AAC ACC GCU CCA GAC GAC GAG CGG G | 134 |
| tPA | N-56.41 | amino-C6-GGG AGG ACG ATG CGG CAA CAU CCC UCU UGU CUU GCU UGC CCU ACA GAC GAC GAG CGG G | 135 |
| VEGF | N-467.65 | amino-C6-GCG GAT CAG CTT GCA CCG GUG CAC UGG GUC AGU AUG GCG GGG GGU UUG GCC AGA AGC AGA AGG ACG | 136 |
| VEGF | N-509.80 | amino-C6-GCG GAT CAG CTT GCA CCG GUG UCC GAA UGG CUC GUU AGG UGG AAC GUG GCC AGA AGC AGA AGG ACG | 137 |
| Von Willebrand Factor | N-311.37 | Amino-C6-GCC GTA GTG ATC GCT CGG GGC CGU UGA CAC AGG GAC CCC AUG UUG UAG GCG AAA CGA CAA GAA GAC | 138 |
| C3 | N-225.65 | amino-C6-GCC GTA GTG ATC GCT CGG UCA GGC CCC CCA GUU UGG GGU AGU UCA GGU GCG AAA CGA CAA GAA GAC | 139 |
| Catalase | N-672.195 | amino-C6-GCC GTA GTG ATC GCT CGG AUU CGU CCG GGA UAG GAC CUG AUC AUG AAG GCC AGA AGC AGA AGG ACG | 140 |
| Catalase | N-434.37 | amino-C6-GCG GAT CAG CTT GCA CCG CUA AGG UGG GUG CGC GUG GGG CGG GGA CAA GCC AGA AGC AGA AGG ACG | 141 |
| IL-4 | N-455.68 | Amino-C6-GCG GAT CAG CTT GCA CCG UCC GCG CGC GGA UAU GCU UUG GGA GUG CUG GCC AGA AGC AGA AGG ACG | 142 |
| IL-8 | N-457.4 | Amino-C6-GCG GAT CAG CTT GCA CCG GGG GUG UAG AGA AUG CCA CAA AGU GCC CGG GCC AGA AGC AGA AGG ACG | 143 |
| VEGF | N-60.87 | amino-C6-GGG AGG ACG ATG CGG CCC UCC CGA CCA CAC CUC CUA UCC UGU CCC UAC UAG AGC AUC AGA CGA CGA GCG GG | 144 |
| VEGF | N-60.61 | amino-C6-GGG AGG ACG ATG CGG CAA GGU ACU ACU CCU AAC CUU AUC CCU UCC UCU UCC UUG CCA GAC GAC GAG CGG G | 145 |
| VEGF | N-60.52 | amino-C6-GGG AGG ACG ATG CGG CAU CAA AAC UGG GGG CGA GUG AUU UAU GUU AGG GGC CUG GCC AGA CGA CGA GCG GG | 146 |

Figure 3 (continued)

U = 5-BrdU
n = A,G,C, or 5-BrdU
amino-C18= amino-(hexaethylene glycol (HEG))

Ac= 5' Acrydite:

| Antibody | 30N12 | N-6.40 | Antibody |
|---|---|---|---|
| OH 6.7 | N-41.76 IL-4 bc | N-12.48 IL-4 | N-28.13 α-2-antiplasmin bp |
| N-5.77 thrombin | N-42.1 IL-7 f | N-8.31 PDGF | N-4.87 PDGF |
| N-40.2 IL-4 | N-14.14 pSelectin | N-13.78 bNGF | N-11.27 angiogenin |
| N-5.4 thrombin | N-7.3 gp120MN | N-3.7 gp120MN | N-50.25 Plasmin f |
| N-71.25 C reactive protein | N-5.51 thrombin | N-41.49 IL-4 bc | N-14.24 pSelectin |
| N-15.83 TGF-β | N-8.37 PDGF | N-7.11 gp120MN | N-112.65 IGFBP-3 |
| N-7.2 gp120MN | N-11.58 angiogenin | N-41.5 IL-4 bc | N-12.8 IL-4 |
| N-92.4 endostatin | Antibody | 30N12 | N-6.40 |
| Antibody | N-11.14 angiogenin | N-38.22 IL-2bp | N-37.93 IgG bs |
| N-42.22 IL-7 f | N-38.47 IL-2 bp | N-13.7 bNGF | N-12.41 IL-4 |
| N-11.11 angiogenin | N-8.27 PDGF | N-12.13 IL-4 | N-11.59 angiogenin |
| N-38.37 IL-2 bp | N-40.3 IL-4 bp | N-15.81 TGF-β | N-14.95 pSelectin |
| N-6.7 bFGF | N-38.38 IL-2 bp | N-15.74 TGF-β | N-13.43 bNGF |
| N-42.5 IL-7 f | N-12.63 IL-4 | N-8.35 PDGF | N-40.5 IL-4 bp |
| N-42.3 IL-7 f | N-14.17 pSelectin | N-8.33 PDGF | N-3.76 gp120MN |
| N-8.26 PDGF | N-11.12 angiogenin | N-28.16 α-2-antiplasmin bp | N-14.21 pSelectin |
| N-6.4 bFGF | N-7.4 gp120MN | N-13.17 bNGF | N-104.49 Epo |
| N-4.24 PDGF | N-51.5 serum amyloid protein | N-5.77 thrombin | OH 6.7 |
| Antibody | 30N12 | N-N6.40 | Antibody |

FIGURE 8

| Cy3-oligo-corner marker | Random DNA (30N12) | Cy3-oligo-corner marker |
|---|---|---|
| N-11.58 angiogenin | N-11.12 angiogenin | N-328.43 endostatin |
| N-334.56 endostatin | N-5.51 thrombin | N-5.77 thrombin |
| N-56.41 tPA | N-56.2 tPA | N-467.65 VEGF |
| N-509.80 VEGF | N-311.37 von Willebrand Factor | N-6.40 bFGF |
| N-6.7 bFGF | N-225.65 C3 | N-672.195 catalase |
| N-434.37 catalase | N-3.7 HIV gp120MN | N-7.20 HIV gp120MN |
| N-112.65 IGFBP-3 | N-455.68 IL-4 | N-40.3 IL-4 |
| N-457.4 IL-8 | N-458.33 Luciferase | N-458.45 Luciferase |
| Cy3-oligo-corner marker | Buffer spots | Cy3-oligo-corner marker |

FIGURE 14

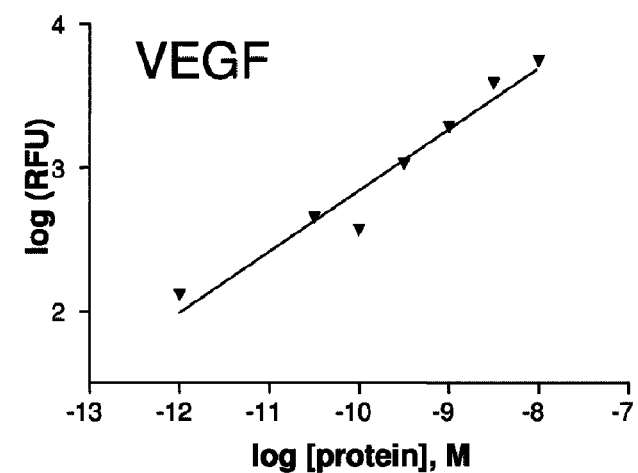
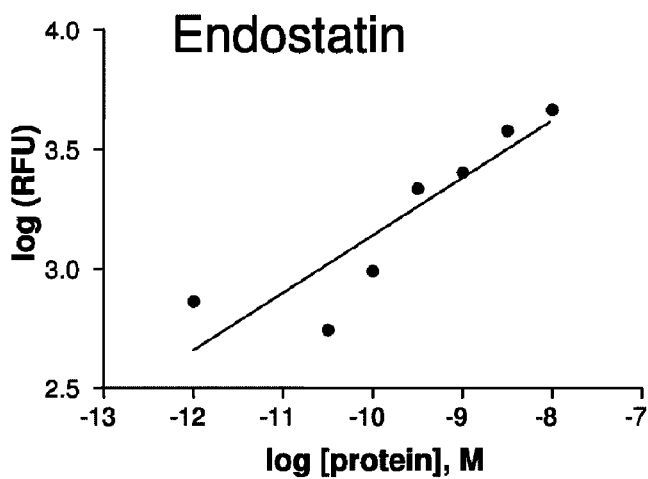
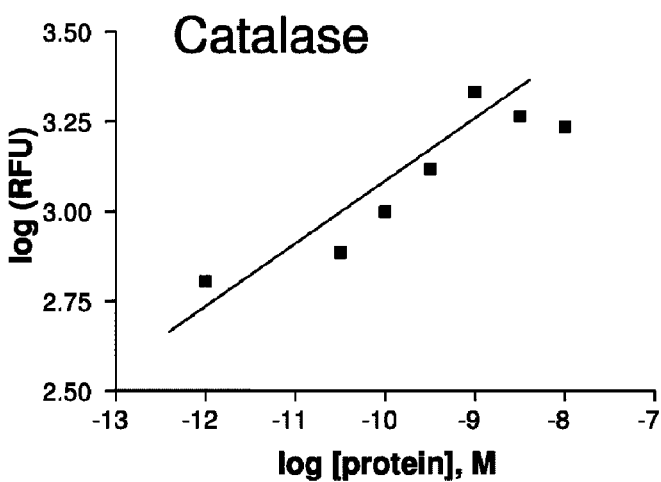
FIGURE 18

SEQUENCE LISTING

```
<160> NUMBER OF SEQ ID NOS: 145

<210> SEQ ID NO 1
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g
```

```
<400> SEQUENCE: 1
gggaggacga tgcggggtca ccttaaccac atgaccagtc tatgccagac gacgagcggg        60

<210> SEQ ID NO 2
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 2
gggaggacga tgcgggcggg agcagtctat gtcatctgtc cacctccaga cgacgagcgg        60
g                                                                        61

<210> SEQ ID NO 3
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 3
gggaggacga tgcggccggg agttaaacac tcagtctatg cgccccagac gacgagcggg        60

<210> SEQ ID NO 4
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 4
gggaggacga tgcgggcccc acggcagtct atgtcatcaa cccccccagac gacgagcggg       60

<210> SEQ ID NO 5
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
```

<223> OTHER INFORMATION: 5'-amino-C6-g

<400> SEQUENCE: 5
gggaggacga tgcgggccca ctttctacag ggcagtctat gtcatcagac gacgagcggg    60

<210> SEQ ID NO 6
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 6
gggaggacga tgcgggccaa ccacgtggta ttattgacct tgcaatggga atgcccagac    60
gacgagcggg    70

<210> SEQ ID NO 7
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 7
gggaggacga tgcggggcaa actgcgtcgt attataagcc tcgctacaga tgccacagac    60
gacgagcggg    70

<210> SEQ ID NO 8
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 8
gggaggacga tgcgggcacc tacctgagct acatatgaca gtgtcaccct ggccccagac    60
gacgagcggg    70

<210> SEQ ID NO 9
<211> LENGTH: 70
<212> TYPE: DNA
<213> ORGANISM: Artificial Sequence
<220> FEATURE:
<223> OTHER INFORMATION: Synthetic Sequence
<220> FEATURE:

```
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 9
gggaggacga tgcgggccaa atggactttt cgccacgaac ttacgacggt gttgccagac    60
gacgagcggg                                                           70

<210> SEQ ID NO 10
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 10
gggaggacga tgcggcacca aaaggtggtc ttagcctaat tatggacgtg tccaccagac    60
gacgagcggg                                                           70

<210> SEQ ID NO 11
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 11
gggaggacga tgcgggccac gtgtattatc ctcagcttat agccatggca tggaccagac    60
gacgagcggg                                                           70

<210> SEQ ID NO 12
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 12
```

```
gggaggacga tgcnggccct acttgcatga atatccactc ctaggcttga gggagcagac    60
gacgagcggg                                                           70

<210> SEQ ID NO 13
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 13
gggaggacga tgcgggcaaa gtcttggtcc accaaatatg tgatgtcacc accagcagac    60
gacgagcggg                                                           70

<210> SEQ ID NO 14
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-acrydite-g

<400> SEQUENCE: 14
gggaggacga tgcgggcaaa gtcttggtcc accaaatatg tgatgtcacc accagcagac    60
gacgagcggg                                                           70

<210> SEQ ID NO 15
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU

<400> SEQUENCE: 15
gggaggacga tgcgggcgaa ggcacaccga gttcatagta tcccacagac gacgagcggg    60
a                                                                    61

<210> SEQ ID NO 16
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU
<220> FEATURE:
<221> NAME/KEY: modified_base
<222> LOCATION: (1)..(1)
```

<223> OTHER INFORMATION: 5'-amino-C6-g

<400> SEQUENCE: 16
gggaggacga tgcgggcgaa ggcacaccga gttcatagta tcccacagac gacgagcggg    60
a    61

<210> SEQ ID NO 17
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-hexaethylene glycol-g

<400> SEQUENCE: 17
gggaggacga tgcgggcgaa ggcacaccga gttcatagta tcccacagac gacgagcggg    60
a    61

<210> SEQ ID NO 18
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU
<220> FEATURE:
<221> NAME/KEY: modified_base
<222> LOCATION: (1)..(1)
<223> OTHER INFORMATION: 5'-biotin-g

<400> SEQUENCE: 18
gggaggacga tgcgggcgaa ggcacaccga gttcatagta tcccacagac gacgagcggg    60
a    61

<210> SEQ ID NO 19
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 19
gggaggacga tgcggtgacg taagagtgta atcgatgcag cctggcagac gacgagcggg    60
a    61

<210> SEQ ID NO 20
<211> LENGTH: 61
<212> TYPE: DNA
<213> ORGANISM: Artificial Sequence
<220> FEATURE:

<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU
<220> FEATURE:
<221> NAME/KEY: modified_base
<222> LOCATION: (1)..(1)
<223> OTHER INFORMATION: 5'-SH-C6-g

<400> SEQUENCE: 20
gggaggacga tgcgggcgaa ggcacaccga gttcatagta tcccacagac gacgagcggg    60
a                                                                    61

<210> SEQ ID NO 21
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-Acrydite-g

<400> SEQUENCE: 21
gggaggacga tgcgggcgaa ggcacaccga gttcatagta tcccacagac gacgagcggg    60

<210> SEQ ID NO 22
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 22
gggaggacga tgcgggacca ataacactac actgatcatc tcccttctat gtccccagac    60
gacgagcggg                                                           70

<210> SEQ ID NO 23
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 23
gggaggacga tgcgggcaca cttaaatcca cttcacctta caattccttt atctgcagac    60
gacgagcggg                                                           70

<210> SEQ ID NO 24
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 24
gggaggacga tgcggccata cgcacttcag tggggataat ccaactggtt tggtgcagac    60
gacgagcggg                                                          70

<210> SEQ ID NO 25
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 25
gggaggacga tgcgggacca ataccaact tcacatcacc tttcttattc tccggcagac     60
gacgagcggg                                                          70

<210> SEQ ID NO 26
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 26
gggaggacga tgcgggcact aactttacct ccacctctaa ccaccctcct ttctgcagac    60
gacgagcggg                                                          70

<210> SEQ ID NO 27
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)

<223> OTHER INFORMATION: 5'-amino-C6-g

<400> SEQUENCE: 27
gggaggacga tgcgggcccc aaacacttgt tcctatcttt caaccccct tgatccagac    60 gacgagcggg                                                          70

<210> SEQ ID NO 28
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-Acrydite-g

<400> SEQUENCE: 28
gggaggacga tgcgggcaca cttaaatcca cttcaccta caattccttt atctgcagac    60
gacgagcggg                                                          70

<210> SEQ ID NO 29
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 29
gggaggacga tgcgggcaca agcccaacct ttcctagatc ttccccagac gacgagcggg    60

<210> SEQ ID NO 30
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 30
gggaggacga tgcggcacca acctagaaga gccaacctag ctgtccagac gacgagcggg    60

<210> SEQ ID NO 31
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)

<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 31
gggaggacga tgcgggcagt aatcacctcg ttgaaccaga cccttcgttt attgccagac    60
gacgagcggg                                                          70

<210> SEQ ID NO 32
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 32
gggaggacga tgcggcaacc cccttactac accttctcca acttgatcac tctgccagac    60
gacgagcggg                                                          70

<210> SEQ ID NO 33
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 33
gggaggacga tgcgggctac gtacaacgtc cactctacct ccgtccagac gacgagcggg    60

<210> SEQ ID NO 34
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 34
gggaggacga tgcggcatgc agtaggtgct taaaccctca gtagtcagac gacgagcggg    60

<210> SEQ ID NO 35
<211> LENGTH: 70
<212> TYPE: DNA
<213> ORGANISM: Artificial Sequence
<220> FEATURE:

```
<223> OTHER INFORMATION: Synthetic Sequence
<220> FEATURE:
<221> NAME/KEY: misc_feature
<222> LOCATION: (16)..(16)
<223> OTHER INFORMATION: n is a, c, g, or 5-BrdU
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 35
gggaggacga tgcggnacca caggttcatt ccaacagctt ctggccgatc tttagcagac      60
gacgagcggg                                                            70

<210> SEQ ID NO 36
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 36
gggaggacga tgcggccact acacctcact aggcttccta ccctccagac gacgagcggg      60

<210> SEQ ID NO 37
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 37
gggaggacga tgcggcaagc agtaaaggat caggaccacc ttaggcagac gacgagcggg      60

<210> SEQ ID NO 38
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 38
gggaggacga tgcggccaca cgatctcctt caccctcctg tccctactag agcatcagac      60
``` gacgagcggg													70

<210> SEQ ID NO 39
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 39
gggaggacga tgcggcacac cctaccctta acctcacctg tccctactag agcatcagac     60 gacgagcggg													70

<210> SEQ ID NO 40
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 40
gggaggacga tgcggggtca ccttcgtttg cttgctgctc cccccagac gacgagcggg      60

<210> SEQ ID NO 41
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-Acrydite-g

<400> SEQUENCE: 41
gggaggacga tgcggggtca ccttcgtttg cttgctgctc cccccagac gacgagcggg      60

<210> SEQ ID NO 42
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU

<400> SEQUENCE: 42
gggaggacga tgcggcaacc caccactcta tctttcccat aactgcagac gacgagcggg     60
a                                                                61

<210> SEQ ID NO 43
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 43
gggaggacga tgcggcaacc caccactcta tctttcccat aactgcagac gacgagcggg      60
a                                                                61

<210> SEQ ID NO 44
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU
<220> FEATURE:
<221> NAME/KEY: modified_base
<222> LOCATION: (1)..(1)
<223> OTHER INFORMATION: 5'-Biotin-g

<400> SEQUENCE: 44
gggaggacga tgcggcaacc caccactcta tctttcccat aactgcagac gacgagcggg      60
a                                                                61

<210> SEQ ID NO 45
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 45
gggaggacga tgcgggacgg acctaccttt tcgcaactac tggtgcagac gacgagcggg      60

<210> SEQ ID NO 46
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)

<223> OTHER INFORMATION: 5'-amino-C6-g

<400> SEQUENCE: 46
gggaggacga tgcggcacag cgagggttgg gcttttctca atttccagac gacgagcggg    60

<210> SEQ ID NO 47
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 47
gggaggacga tgcgggctgc ggctaccgtt tccttaccga ctgggcagac gacgagcggg    60

<210> SEQ ID NO 48
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 48
gggaggacga tgcgggaaca cttgtcgata gtcttggtta agctgcagac gacgagcggg    60

<210> SEQ ID NO 49
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 49
gggaggacga tgcggcacaa tgaagtcact cttgacgctt gtattcagac gacgagcggg    60

<210> SEQ ID NO 50
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)

```
<223> OTHER INFORMATION: 5'-Acrydite-g

<400> SEQUENCE: 50
gggaggacga tgcggcacaa tgaagtcact cttgacgctt gtattcagac gacgagcggg    60

<210> SEQ ID NO 51
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 51
gggaggacga tgcgggcgga cttgacggtg tcttgcgaag ctcctacttt acctacagac    60
gacgagcggg                                                            70

<210> SEQ ID NO 52
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 52
gggaggacga tgcgggcagt tagcgatagc ctttccaagt ccttgtgacg ttgcccagac    60
gacgagcggg                                                            70

<210> SEQ ID NO 53
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU

<400> SEQUENCE: 53
gggaggacga tgcggaatgc gcgagcttcc gaaaaggaaa ttacgcagac gacgagcggg    60
a                                                                     61

<210> SEQ ID NO 54
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU
<220> FEATURE:
```

<221> NAME/KEY: modified_base
<222> LOCATION: (1)..(1)
<223> OTHER INFORMATION: 5'-amino-C6-g

<400> SEQUENCE: 54
gggaggacga tgcggaatgc gcgagcttcc gaaaaggaaa ttacgcagac gacgagcggg    60
a                                                                    61

<210> SEQ ID NO 55
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU
<220> FEATURE:
<221> NAME/KEY: modified_base
<222> LOCATION: (1)..(1)
<223> OTHER INFORMATION: 5'-SH-C6-g

<400> SEQUENCE: 55
gggaggacga tgcggaatgc gcgagcttcc gaaaaggaaa ttacgcagac gacgagcggg    60
a                                                                    61

<210> SEQ ID NO 56
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 56
gggaggacga tgcggcaacc acacgcagga ggacacaacg atccgcagac gacgagcggg    60

<210> SEQ ID NO 57
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 57
gggaggacga tgcgggcgaa ggcacaccga gttcatagta tcccacagac gacgagcggg    60

<210> SEQ ID NO 58
<211> LENGTH: 60
<212> TYPE: DNA
<213> ORGANISM: Artificial Sequence
<220> FEATURE:
<223> OTHER INFORMATION: Synthetic Sequence
<220> FEATURE:

```
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 58
gggaggacga tgcgggacga gggaccagac cgccacagcg ggatgcagac gacgagcggg    60

<210> SEQ ID NO 59
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 59
gggaggacga tgcgggagga ccacgaccat gacccaccag gaatgcagac gacgagcggg    60

<210> SEQ ID NO 60
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 60
gggaggacga tgcgggcaca ggcctaacat acctccatct cctggcagac gacgagcggg    60

<210> SEQ ID NO 61
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 61
gggaggacga tgcgggacca acgagaccac acgacaagcg ctgtgcagac gacgagcggg    60

<210> SEQ ID NO 62
<211> LENGTH: 57
<212> TYPE: DNA
<213> ORGANISM: Artificial Sequence
<220> FEATURE:
<223> OTHER INFORMATION: Synthetic Sequence
<220> FEATURE:
```

```
<221> NAME/KEY: modified_base
<222> LOCATION: (1)..(57)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 62
gggaggacga tgcgggccat ggatggtttg gttggctgtc ctcagacgac gagcggg        57

<210> SEQ ID NO 63
<211> LENGTH: 61
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(61)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-hexaethylene glycol-g

<400> SEQUENCE: 63
gggaggacga tgcggaatgc gcgagcttcc gaaaaggaaa ttacgcagac gacgagcggg     60
a                                                                    61

<210> SEQ ID NO 64
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 64
gggaggacga tgcgggcaaa gtgttatttc ttgatctgtt tcacccagac gacgagcggg     60

<210> SEQ ID NO 65
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-Acrydite-g

<400> SEQUENCE: 65
gggaggacga tgcgggcaaa gtgttatttc ttgatctgtt tcacccagac gacgagcggg     60

<210> SEQ ID NO 66
<211> LENGTH: 60
<212> TYPE: DNA
<213> ORGANISM: Artificial Sequence
<220> FEATURE:
```

```
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 66
gggaggacga tgcggccacc atgtcacctc aattacccct cctcccagac gacgagcggg    60

<210> SEQ ID NO 67
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 67
gggaggacga tgcggccaac cctcactcct tcttcacttc acctccagac gacgagcggg    60

<210> SEQ ID NO 68
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 68
gggaggacga tgcgggcaca actcccacca cccttctttc aactccctac tgccccagac    60
gacgagcggg                                                            70

<210> SEQ ID NO 69
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 69
gggaggacga tgcgggcaga cagtgtgggg tttagtgtcc atggccagac gacgagcggg    60

<210> SEQ ID NO 70
<211> LENGTH: 60
<212> TYPE: DNA
```

<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 70
gggaggacga tgcgggcaca ctcttcaccc cctccttta gctgccagac gacgagcggg    60

<210> SEQ ID NO 71
<211> LENGTH: 59
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(59)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 71
gggaggacga tgcgggacct ccgggtaacc aggtaactcc tagccagacg acgagcggg    59

<210> SEQ ID NO 72
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 72
gggaggacga tgcggccacc tacctctaca ctaccttacc tactccagac gacgagcggg    60

<210> SEQ ID NO 73
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 73
gggaggacga tgcgggcagg caaccttacc aagatgcccc tcctgcagac gacgagcggg    60

<210> SEQ ID NO 74
<211> LENGTH: 60
<212> TYPE: DNA

<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 74
gggaggacga tgcggcacac ccctcaactt accctacttc ttggccagac gacgagcggg    60

<210> SEQ ID NO 75
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-Biotin-g

<400> SEQUENCE: 75
gggaggacga tgcggccccg agtttcccta aggtttggtt gacctgtcat ttcagcagac    60
gacgagcggg                                                            70

<210> SEQ ID NO 76
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 76
gggaggacga tgcggccccg agtttcccta aggtttggtt gacctgtcat ttcagcagac    60
gacgagcggg                                                            70

<210> SEQ ID NO 77
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 77
gggaggacga tgcgggccga agtctaaacc tgctcgtgac tttctttcga tgttgcagac    60
gacgagcggg                                                          70

<210> SEQ ID NO 78
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 78
gggaggacga tgcgggccta ccaactcccc tctagtcctg ttctatccac gttggcagac    60
gacgagcggg                                                          70

<210> SEQ ID NO 79
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 79
gggaggacga tgcgggccaa ggttcccttc tgcctcattg ttgtgggaac ccatccagac    60
gacgagcggg                                                          70

<210> SEQ ID NO 80
<211> LENGTH: 69
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(69)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 80
gggaggacga tgcgggcaca ggttctatca acgttgtcct gagtaattga cctgcagacg    60
acgagcggg                                                           69

<210> SEQ ID NO 81
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:

```
<221> NAME/KEY: modified_base
<222> LOCATION: (1)..(1)
<223> OTHER INFORMATION: 5'-amino-C6-g

<400> SEQUENCE: 81
gggaggacga tgcgggccaa ggacattctt gttcgttgtt gctgtccact gtctccagac    60
gacgagcggg                                                           70

<210> SEQ ID NO 82
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-Acrydite-g

<400> SEQUENCE: 82
gggaggacga tgcggccccg agtttcccta aggtttggtt gacctgtcat ttcagcagac    60
gacgagcggg                                                           70

<210> SEQ ID NO 83
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 83
gggaggacga tgcggcacac ggttgccata cccttcatta ttgagcagac gacgagcggg    60

<210> SEQ ID NO 84
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 84
gggaggacga tgcggccggc tgcttccccc ctggtcattg ttgtgcagac gacgagcggg    60

<210> SEQ ID NO 85
<211> LENGTH: 60
<212> TYPE: DNA
<213> ORGANISM: Artificial Sequence
<220> FEATURE:
<223> OTHER INFORMATION: Synthetic Sequence
<220> FEATURE:
```

```
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 85
gggaggacga tgcgggccaa agttcccatc cacgttactc tttgccagac gacgagcggg    60

<210> SEQ ID NO 86
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 86
gggaggacga tgcgggccaa ggttcccttc tgcctcattg ttgtgcagac gacgagcggg    60

<210> SEQ ID NO 87
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 87
gggaggacga tgcgggcacc ttctatcgac gttgcggtac ccatgcagac gacgagcggg    60

<210> SEQ ID NO 88
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 88
gggaggacga tgcgggcgga tcccagcgcg gctaacgttt ggggcagac gacgagcggg    60

<210> SEQ ID NO 89
<211> LENGTH: 60
<212> TYPE: DNA
<213> ORGANISM: Artificial Sequence
<220> FEATURE:
<223> OTHER INFORMATION: Synthetic Sequence
<220> FEATURE:
```

```
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 89
gggaggacga tgcgggaggc ggatcctaac gttgatttgg tgtgccagac gacgagcggg    60

<210> SEQ ID NO 90
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 90
gggaggacga tgcggcaact accggctggg gacctgaact tcatatcccc ttccccagac    60
gacgagcggg                                                          70

<210> SEQ ID NO 91
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 91
gggaggacga tgcgggcacc agaacctgac cttaatgccc cctttctcag ctaagcagac    60
gacgagcggg                                                          70

<210> SEQ ID NO 92
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 92
gggaggacga tgcgggcagg acggacgggt gagcttccct gatttaactc taccacagac    60
gacgagcggg                                                          70

<210> SEQ ID NO 93
```

```
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 93
gggaggacga tgcgggccac ctgaatccct acgttgatag gagtatcccc ttgcccagac    60
gacgagcggg                                                           70

<210> SEQ ID NO 94
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 94
gggaggacga tgcgggctga aaggaaacgg acgattgagc ttcccctyac ctctccagac    60
gacgagcggg                                                           70

<210> SEQ ID NO 95
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 95
gggaggacga tgcgggacgc tagtaccctg gctggcttgg ttgggcagac gacgagcggg    60

<210> SEQ ID NO 96
<211> LENGTH: 67
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(67)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 96
```
gggaggacga tgcgggcacg cactacaggt tggtttggtt ggactttccg cacagacgac    60
gagcggg    67

<210> SEQ ID NO 97
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 97
gggaggacga tgcggcacaa accgagctct gtccagtcta tcttcacatc ttccccagac    60
gacgagcggg    70

<210> SEQ ID NO 98
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 98
gggaggacga tgcggcctgg attcaataac cggcactccc cttacctcat gggtccagac    60
gacgagcggg    70

<210> SEQ ID NO 99
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 99
gggaggacga tgcgggacca ctttaacctt cctttctcat ttccaccccc ctccccagac    60
gacgagcggg    70

<210> SEQ ID NO 100
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)

<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 100
gggaggacga tgcgggcgga agaggcaggg taccacggca gaggtcagac gacgagcggg    60

<210> SEQ ID NO 101
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 101
gggaggacga tgcgggccaa cccctagtga acaacaacac tcccacagac gacgagcggg    60

<210> SEQ ID NO 102
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 102
gggaggacga tgcggcagca ccgaggtacc caacagggat ccgcccagac gacgagcggg    60

<210> SEQ ID NO 103
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 103
gggaggacga tgcgggcggc agacgcgccg ggtaccccag gtccccagac gacgagcggg    60

<210> SEQ ID NO 104
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)

```
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 104
gggaggacga tgcggcacaa ggaacaaagc ggcccctatc cccaacagac gacgagcggg    60

<210> SEQ ID NO 105
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 105
gggaggacga tgcgggggggc aagaagcacg gtaccccagg tccgccagac gacgagcggg    60

<210> SEQ ID NO 106
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 106
gggaggacga tgcggccgga catcccccag ggcaaaacca actcccagac gacgagcggg    60

<210> SEQ ID NO 107
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 107
gggaggacga tgcggcaagg gaaacagata gcccaggctc cccccagac gacgagcggg    60

<210> SEQ ID NO 108
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
```

-continued

```
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 108
gggaggacga tgcggcaacc ctgacaccac gttgtttctc cttttggggt aaccgcagac    60
gacgagcggg                                                           70

<210> SEQ ID NO 109
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-Acrydite-g

<400> SEQUENCE: 109
gggaggacga tgcggcaacc ctgacaccac gttgtttctc cttttggggt aaccgcagac    60
gacgagcggg                                                           70

<210> SEQ ID NO 110
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 110
gggaggacga tgcggcgccc cgattgacct tcgatttatc ctacttatgg caccccagac    60
gacgagcggg                                                           70

<210> SEQ ID NO 111
<211> LENGTH: 69
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(69)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 111
gggaggacga tgcggcacga gggaatcacc tcgaacttgt cctggattac tgcccagacg    60
acgagcggg                                                            69

<210> SEQ ID NO 112
```

```
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 112
gggaggacga tgcggccatg aacccatcct ctggttcata atcgacgtgt tcgtgcagac    60
gacgagcggg                                                            70

<210> SEQ ID NO 113
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 113
gggaggacga tgcgggctca ataacctgaa tctacctttc cctagcaaag gtctgcagac    60
gacgagcggg                                                            70

<210> SEQ ID NO 114
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 114
gggaggacga tgcggccata cgcacttcag tggggataat ccaactggtt tggtgcagac    60
gacgagcggg                                                            70

<210> SEQ ID NO 115
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g
```

<400> SEQUENCE: 115
gggaggacga tgcgggccga ctctgaggaa aaggttttat gtatggctac ccctgcagac    60
gacgagcggg    70

<210> SEQ ID NO 116
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-Acrydite-g

<400> SEQUENCE: 116
gggaggacga tgcgggccga ctctgaggaa aaggttttat gtatggctac ccctgcagac    60
gacgagcggg    70

<210> SEQ ID NO 117
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 117
gggaggacga tgcgggcaca accttaccac cctagcctac ccctaacctc ctgtccagac    60
gacgagcggg    70

<210> SEQ ID NO 118
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 118
gggaggacga tgcgggacca tccaatacct tccgtaacac tttccttctt ccttccagac    60
gacgagcggg    70

<210> SEQ ID NO 119
<211> LENGTH: 70
<212> TYPE: DNA
<213> ORGANISM: Artificial Sequence
<220> FEATURE:
<223> OTHER INFORMATION: Synthetic Sequence
<220> FEATURE:

```
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 119
gggaggacga tgcgggcagc aacctacctt accttcccct agcctacctt atccccagac    60
gacgagcggg                                                           70

<210> SEQ ID NO 120
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 120
gggaggacga tgcgggcacc tttcttacat cttggcttca ttcttgcacc attggcagac    60
gacgagcggg                                                           70

<210> SEQ ID NO 121
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 121
gggaggacga tgcgggcaca atcaagacct ctccaaactt gaactctgtc tatcccagac    60
gacgagcggg                                                           70

<210> SEQ ID NO 122
<211> LENGTH: 58
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(58)
<223> OTHER INFORMATION: t is 5-BrdU

<400> SEQUENCE: 122
gggaggacga tgcgggcagt aggttgggta gggtggtctg ctcagacgac gagcggga      58

<210> SEQ ID NO 123
<211> LENGTH: 58
<212> TYPE: DNA
<213> ORGANISM: Artificial Sequence
<220> FEATURE:
```

```
<223> OTHER INFORMATION: Synthetic Sequence
<220> FEATURE:
<221> NAME/KEY: modified_base
<222> LOCATION: (1)..(58)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 123
gggaggacga tgcgggcagt aggttgggta gggtggtctg ctcagacgac gagcggga        58

<210> SEQ ID NO 124
<211> LENGTH: 58
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(58)
<223> OTHER INFORMATION: t is 5-BrdU
<220> FEATURE:
<221> NAME/KEY: modified_base
<222> LOCATION: (1)..(1)
<223> OTHER INFORMATION: 5'-Biotin-g

<400> SEQUENCE: 124
gggaggacga tgcgggcagt aggttgggta gggtggtctg ctcagacgac gagcggga        58

<210> SEQ ID NO 125
<211> LENGTH: 60
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-Biotin-g

<400> SEQUENCE: 125
gggaggacga tgcgggcagg acggacagca agggtgagc acgagcagac gacgagcggg       60

<210> SEQ ID NO 126
<211> LENGTH: 57
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(57)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 126
gggaggacga tgcgggagga gctgatgggt ggtgaggttg ccagacgac gagcggg          57

<210> SEQ ID NO 127
<211> LENGTH: 60
<212> TYPE: DNA
<213> ORGANISM: Artificial Sequence
<220> FEATURE:
```

-continued

```
<223> OTHER INFORMATION: Synthetic Sequence
<220> FEATURE:
<221> NAME/KEY: modified_base
<222> LOCATION: (1)..(60)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 127
gggaggacga tgcgggcagg acggacagca aggggtgagc acgagcagac gacgagcggg    60

<210> SEQ ID NO 128
<211> LENGTH: 58
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(58)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 128
gggaggacga tgcgggcggt tggcgtggtt ggaaatgtcc cgtcagacga cgagcggg      58

<210> SEQ ID NO 129
<211> LENGTH: 57
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(57)
<223> OTHER INFORMATION: t is 5-BrdU
<220> FEATURE:
<221> NAME/KEY: modified_base
<222> LOCATION: (1)..(1)
<223> OTHER INFORMATION: 5'-Acrydite-g

<400> SEQUENCE: 129
gggaggacga tgcgggcagt aggttgggta gggtggtctg ctcagacgac gagcggg       57

<210> SEQ ID NO 130
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 130
gggaggacga tgcgggcagg agtccacttt cactccacct accggaatgt taccccagac    60
gacgagcggg                                                           70

<210> SEQ ID NO 131
<211> LENGTH: 71
<212> TYPE: DNA
```

```
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(71)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 131
gggaggacga tgcggccctc ccgaccacac ctcctatcct gtccctacta gagcatcaga    60
cgacgagcgg g                                                         71

<210> SEQ ID NO 132
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 132
gggaggacga tgcggcaagg tactactcct aaccttatcc cttcctcttc cttgccagac    60
gacgagcggg                                                           70

<210> SEQ ID NO 133
<211> LENGTH: 71
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(71)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 133
gggaggacga tgcggcatca aaactggggg cgagtgattt atgttagggg cctggccaga    60
cgacgagcgg g                                                         71

<210> SEQ ID NO 134
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(70)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 134
```

```
gggaggacga tgcgggctgg aacatccct cttgtcttgc ttaccaacac cgctccagac    60
gacgagcggg                                                          70
```

<210> SEQ ID NO 135
<211> LENGTH: 58
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(58)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 135

```
gggaggacga tgcggcaaca tccctcttgt cttgcttgcc ctacagacga cgagcggg    58
```

<210> SEQ ID NO 136
<211> LENGTH: 66
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(66)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 136

```
gcggatcagc ttgcaccggt gcactgggtc agtatggcgg ggggtttggc cagaagcaga    60
aggacg                                                               66
```

<210> SEQ ID NO 137
<211> LENGTH: 66
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(66)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 137

```
gcggatcagc ttgcaccggt gtccgaatgg ctcgttaggt ggaacgtggc cagaagcaga    60
aggacg                                                               66
```

<210> SEQ ID NO 138
<211> LENGTH: 66
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(66)
<223> OTHER INFORMATION: t is 5-BrdU
<220> FEATURE:

```
<221> NAME/KEY: modified_base
<222> LOCATION: (1)..(1)
<223> OTHER INFORMATION: 5'-amino-C6-g

<400> SEQUENCE: 138
gccgtagtga tcgctcgggg ccgttgacac agggacccca tgttgtaggc gaaacgacaa      60
gaagac                                                                66

<210> SEQ ID NO 139
<211> LENGTH: 66
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(66)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 139
gccgtagtga tcgctcggtc aggcccccca gtttgggta gttcaggtgc gaaacgacaa       60
gaagac                                                                66

<210> SEQ ID NO 140
<211> LENGTH: 66
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(66)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 140
gccgtagtga tcgctcggat tcgtccggga taggacctga tcatgaaggc cagaagcaga      60
aggacg                                                                66

<210> SEQ ID NO 141
<211> LENGTH: 66
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(66)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 141
gcggatcagc ttgcaccgct aaggtgggtg cgcgtggggc ggggacaagc cagaagcaga      60
aggacg                                                                66

<210> SEQ ID NO 142
<211> LENGTH: 66
<212> TYPE: DNA
```

<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(66)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 142
gcggatcagc ttgcaccgtc cgcgcgcgga tatgctttgg gagtgctggc cagaagcaga    60
aggacg    66

<210> SEQ ID NO 143
<211> LENGTH: 66
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(66)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 143
gcggatcagc ttgcaccggg ggtgtagaga atgccacaaa gtgcccgggc cagaagcaga    60
aggacg    66

<210> SEQ ID NO 144
<211> LENGTH: 66
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(66)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 144
gcggatcagc ttgcaccgta ggggctcggt tgggcagggg tagggtaagc cagaagcaga    60
aggacg    66

<210> SEQ ID NO 145
<211> LENGTH: 66
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(66)
<223> OTHER INFORMATION: t is 5-BrdU
<220> FEATURE:
<221> NAME/KEY: modified_base
<222> LOCATION: (1)..(1)
<223> OTHER INFORMATION: 5'-amino-C6-g

<400> SEQUENCE: 145

```
gcggatcagc ttgcaccggg gtgctcgggt tagggcaggg atgggtaagc cagaagcaga      60
aggacg                                                                 66
```

METHODS AND REAGENTS FOR DETECTING TARGET BINDING BY NUCLEIC ACID LIGANDS

RELATED APPLICATIONS

This application is a continuation of U.S. application Ser. No. 10/504,696, filed Apr. 15, 2005, now abandoned which is a 35 U.S.C. § 371 national phase application of PCT/US03/04142 (WO 03/070984), filed on Feb. 10, 2003, both of which are entitled "Methods and Reagents for Detecting Target Binding by Nucleic Acid Ligands." PCT/US03/04142 claims the benefit of U.S. Provisional Application Ser. No. 60/357,297, filed Feb. 15, 2002, U.S. Provisional Application Ser. No. 60/398,666, filed Jul. 26, 2002 and U.S. Provisional Application Ser. No. 60/400,759, filed Aug. 2, 2002, each of which is entitled "Methods for the Multiplexed Evaluation of Photocrosslinking Nucleic Acid Ligands." PCT/US03/04142 is also a continuation of U.S. application Ser. No. 10/114,187, filed Apr. 1, 2002, now abandoned entitled "Photoselection of Nucleic Acid Ligands". This application is also continuation in part of U.S. patent application Ser. No. 10/375,487, filed Feb. 27, 2003, now U.S. Pat. No. 7,709,192, which is a continuation of U.S. patent application Ser. No. 09/581,465, filed Aug. 14, 2000, now U.S. Pat. No. 6,544,776, which is a 35 U.S.C. § 371 national phase application of International Application No. PCT/US98/26515, filed Dec. 14, 1998 (WO 99/31275), each of which is entitled "Nucleic Acid Ligand Diagnostic Biochip." PCT/US98/26515 is a continuation of U.S. patent application Ser. No. 08/990,436, filed Dec. 15, 1997, now U.S. Pat. No. 6,242,246, entitled "Nucleic Acid Ligand Diagnostic Biochip." Each of these applications is specifically incorporated herein by reference in its entirety

FIELD OF THE INVENTION

The invention is directed towards nucleic acid ligands, methods of characterizing nucleic acid ligands, and methods and reagents for detecting target binding to nucleic acid ligands.

BACKGROUND OF THE INVENTION

The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096 entitled "Nucleic Acid Ligands", and U.S. Pat. No. 5,270,163 (see also WO 91/19813) entitled "Nucleic Acid Ligands" each of which is specifically incorporated by reference herein. Each of these patents and applications, collectively referred to herein as the SELEX patent applications, describes a fundamentally novel method for making a nucleic acid ligand to any desired target molecule. The SELEX process provides a class of products which are referred to as nucleic acid ligands or aptamers, each having a unique sequence, and which has the property of binding specifically to a desired target compound or molecule. Each SELEX process-identified nucleic acid ligand is a specific ligand of a given target compound or molecule.

The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX process applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX process includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

One particularly important embodiment of the SELEX process is described in U.S. patent application Ser. No. 08/123,935, filed Sep. 17, 1993, and U.S. patent application Ser. No. 08/443,959 filed May 18, 1995, both entitled "Photoselection of Nucleic Acid Ligands," and both now abandoned, and U.S. Pat. Nos. 5,763,177, 6,001,577, WO 95/08003, U.S. Pat. Nos. 6,291,184, 6,458,539, and U.S. patent application Ser. No. 09/723,718, filed Nov. 28, 2000, each of which is entitled "Systematic Evolution of Nucleic Acid Ligands by Exponential Enrichment: Photoselection of Nucleic Acid Ligands and Solution SELEX," and each of which describe a SELEX process-based method for selecting nucleic acid ligands containing photoreactive groups capable of binding and/or photocrosslinking to and/or photoinactivating a target molecule. The resulting nucleic acid ligands are referred to interchangeably as "photocrosslinking nucleic acid ligands" and "photoaptamers." These patents and patent applications are referred to in this application collectively as "the PhotoSELEX Process Applications." In the photoSELEX process embodiment of the SELEX process, a modified nucleotide activated by absorption of light is incorporated in place of a native base in either RNA- or in ssDNA-randomized oligonucleotide libraries. One such photoreactive nucleotide whose photochemistry is particularly well-suited for this purpose is 5-bromo-2'-deoxyuridine (5-BrdU) (Meisenheimer and Koch (1997) Crit. Rev. Biochem. Mol. Biol. 32:101-140). The 5-BrdU chromophore absorbs ultraviolet (UV) light in the 310 nm range where native chromophores of nucleic acids and proteins do not absorb or absorb very weakly. The resulting excited singlet state intersystem crosses to the lowest triplet state which specifically crosslinks with aromatic and sulfur-bearing amino acid residues of a protein target in suitable proximity (Dietz and Koch (1987) Photochem. Photobiol. 46:971-8; Dietz and Koch (1989) Photochem. Photobiol. 49:121-9; Dietz et al. (1987) J. Am. Chem. Soc. 109:1793-1797; Ito et al. (1980) J. Am. Chem. Soc. 102:7535-7541; Swanson et al. (1981) J. Am. Chem. Soc. 103:1274-1276). Crosslinking may also occur via excitation of an aromatic residue of the protein in proximity to the bromouracil chromophore (Norris et al. (1997) Photochem. Photobiol. 65:201-207). Of particular importance, excited bromouracil in DNA is relatively unreactive in the absence of a proximal, oriented, reactive amino acid (Gott et al. (1991) Biochemistry 30:6290-6295; Willis et al. (1994) Nucleic Acids Res. 22:4947-4952; Norris et al. (1997) Photochem. Photobiol. 65:201-207) or nucleotide residue (Sugiyama et al. (1990) J. Am. Chem. Soc. 112:6720-6721; Cook and Greenberg (1996) J. Am. Chem. Soc. 118:10025-10030). The importance of orientation is evident in crystal structures of protein-nucleic acid complexes which show a lock and key arrangement of the bromouracil chromophore with the aromatic amino acid residue to which it crosslinks (Horvath et al. (1998) Cell 95:963-974; Meisenheimer and Koch (1997) Crit. Rev. Biochem. Mol. Biol. 32:101-140).

In a basic embodiment, the photoSELEX process comprises the following steps:

a) A candidate mixture of nucleic acids is prepared. The candidate mixture nucleic acids comprise sequences with randomized regions including photoreactive groups, e.g. by incorporating 5-BrdU into the candidate mixture.

b) The candidate mixture is contacted with a quantity of target. Nucleic acid ligands of the target in the candidate mixture form complexes with the target;

c) The photoreactive groups in candidate nucleic acid ligands are photoactivated by irradiation. Nucleic acid ligands that have formed specific complexes with target thereby become photocrosslinked to the target;

d) Nucleic acid ligands that have become photocrosslinked to target are partitioned from other nucleic acids in the candidate mixture;

e) The nucleic acid ligands that photocrosslinked to the target are released from the target (e.g., by protease digestion if the target is a protein), and then amplified; and f) The amplified nucleic acid ligands are used as the candidate mixture to initiate another round of the photoSELEX process.

The photoSELEX process produces nucleic acid ligands that are single- or double-stranded RNA or DNA oligonucleotides. A photoreactive group may comprise a natural nucleic acid residue with a relatively simple modification that confers increased reactivity or photoreactivity to the nucleic acid residue. Such modifications include, but are not limited to, modifications at cytosine exocyclic amines, substitution with halogenated groups, e.g., 5'-bromo- or 5'-iodo-uracil, modification at the 2'-position, e.g., 2'-amino (2'-NH$_2$) and 2'-fluoro (2'-F), backbone modifications, methylations, unusual base-pairing combinations and the like. For example, photocrosslinking nucleic acid ligands produced by the photoSELEX process can include a photoreactive group selected from the following: 5-bromouracil (BrU), 5-iodouracil (IU), 5-bromovinyluracil, 5-iodovinyluracil, 5-azidouracil, 4-thiouracil, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-azidoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-bromodeoxyuridine, 8-bromo-2'-deoxyadenine, 5-iodo-2'-deoxyuracil, 5-iodo-2'-deoxycytosine, 5-[(4-azidophenacyl)thio]cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine. Preferably, the photoreactive group will absorb light in a spectrum of the wavelength that is not absorbed by the target or the non-modified portions of the oligonucleotide. In preferred embodiments of the photoSELEX process, the photoreactive nucleotides incorporated into the photocrosslinking nucleic acid ligands are 5-bromo-2'-deoxyuridine (5-BrdU) and 5-iodo-2'-deoxyuridine (5-IdU). These nucleotides can be incorporated into DNA in place of thymidine nucleotides.

Photocrosslinking nucleic acid ligands produced by the photoSELEX process have particular utility in diagnostic or prognostic medical assays. In one such embodiment, photocrosslinking nucleic acid ligands of targets implicated in disease are attached to a planar solid support in an array format, and the solid support is then contacted with a biological fluid to be analyzed for the presence or absence of the targets. The photocrosslinking nucleic acid ligands are photoactivated and the solid support is washed under very stringent, aggressive conditions (preferably under conditions that denature nucleic acids and/or proteins) in order to remove all non-specifically bound molecules. Bound target is not removed because it is covalently crosslinked to nucleic acid ligand via the photoreactive group. The ability to photocrosslink, followed by stringent washing, allows diagnostic and prognostic assays of unparalleled sensitivity and specificity to be performed. Arrays (also commonly referred to as "biochips" or "microarrays") of nucleic acid ligands, including photocrosslinking nucleic acid ligands and aptamers, and methods for their manufacture and use, are described in U.S. Pat. Nos. 6,242,246, U.S. patent application Ser. No. 08/211,680, filed Dec. 14, 1998, now abandoned, WO 99/31275, U.S. patent application Ser. No. 09/581,465, filed Jun. 12, 2000, U.S. Pat. Nos. 6,503,715, and 6,458,543, each of which is entitled "Nucleic Acid Ligand Diagnostic Biochip." These patents and patent applications are referred to collectively as "the biochip applications," and are each specifically incorporated herein by reference in their entirety.

Automated methods and apparatus for the generation of photocrosslinking nucleic acid ligands are provided in U.S. patent application Ser. No. 09/993,294, filed Nov. 21, 2001, U.S. patent application Ser. No. 09/815,171, filed Mar. 22, 2001, U.S. patent application Ser. No. 09/616,284, filed Jul. 14, 2000, U.S. patent application Ser. No. 09/356,233, filed Jul. 16, 1999, U.S. patent application Ser. No. 09/232,946, filed Jan. 19, 1999, each of which is entitled "Method and Apparatus for the Automated Generation of Nucleic Acid Ligands." Given the rapidity with which these highly parallel, automated methods can generate photocrosslinking nucleic acid ligands, it is desirable to have multiplexed methods for evaluation of the specificity and dose-response characteristics of those photocrosslinking nucleic acid ligands. The present invention includes such methods.

SUMMARY OF THE INVENTION

In one aspect, the invention provides a method for detecting the presence of a target molecule suspected of being contained in a test mixture, wherein said target molecule is a protein, the method comprising:

a) providing a solid support, said solid support comprising a photoreactive nucleic acid ligand having specific affinity for said target protein, said photoreactive nucleic acid ligand binding specifically to said target molecule through non-Watson-Crick interactions;

b) contacting said solid support with said test mixture suspected of containing said target molecule, wherein a nucleic acid ligand-target molecule complex is formed if said target molecule is present;

c) irradiating said solid support, wherein said nucleic acid ligand-target molecule complex photocrosslinks;

d) removing non-specifically bound material from said solid support;

e) contacting said solid support with a Universal Protein Stain (UPS), said UPS comprising one or more reagents that label proteins with a detectable moiety; and f) detecting the presence of said target molecule by detecting the presence of said detectable moiety on said solid support.

In preferred embodiments, step d) is accomplished by exposing said biochip to conditions that denature nucleic acids and/or proteins.

Suitable detectable moieties include, but are not limited to, dyes (including fluorophores), enzymes (including, but not limited to, alkaline phosphatase and horseradish peroxidase), enzyme substrates, and radiolabels.

In preferred embodiments, at least one of said UPS reagents reacts with a group found on a protein, including but not limited to primary amines (preferably on lysine residues), thiols, alcohols (including, but not limited to, alcohols groups on serine, threonine, tyrosine, and sugar moieties on glycoproteins), and carboxylates.

In some embodiments, the UPS comprises an N-hydroxysuccinimide-activated dye, most preferably an N-hydroxysuccinimide-activated fluorophore, including but not limited to NHS-ALEXA fluorophores.

In other embodiments, the UPS comprises CBQCA (3-(4-carboxybenzoyl)quinoline-2-carboxaldehyde).

In still further embodiments, the UPS comprises a reagent that bears an amine reactive group selected from the list consisting of isocyanates, isothiocyanates, acyl azides, sulfonyl chlorides, aldehydes, 4-sulfo-2,3,5,6-tetrafluorophenol (STP) esters, NBD (7-nitrobenz-2-oxa-1,3-diazole) chloride, NBD fluoride, and dichlorotriazines.

In still further embodiments, the UPS comprises a biotin derivative capable of reacting with primary amines and a streptavidin derivatized with said detectable moiety.

In even further embodiments, the UPS comprises: a first biotin derivative capable of reacting with primary amines, streptavidin, and a second biotin derivative conjugated to said detectable moiety.

In yet further embodiments, the UPS comprises: 2-iminothiolane and a thiol-reactive derivative of a dye, preferably a maleimide derivative of a dye.

In still further embodiments, the UPS comprises: a hapten derivative capable of reacting with primary amines and an anti-hapten antibody conjugated to said detectable moiety. Alternatively, the detectable moiety may be conjugated to a secondary antibody that recognizes the anti-hapten antibody.

In further embodiments, the UPS comprises: a reagent that modifies amino acid side chains and an antibody that specifically recognizes said modified amino acid side chain. In this embodiment, the antibody may be conjugated to the detectable moiety. Alternatively, the detectable moiety may be conjugated to a secondary antibody that recognizes the anti-modified side chain antibody. Suitable reagents for the modification of amino acid side chains according to this embodiment include, but are not limited to nitrosylating agents (such as tetranitromethane) and acetylating agents (such as sulfo-N-hydroxysuccinimide acetate). Nitrosylated proteins may be recognized by anti-nitro tyrosine antibodies; acetylated proteins may be recognized by anti-acetylated lysine antibodies.

The UPS reagents and methods provided herein are especially useful in embodiments where multiplexed assays are performed using a biochip (also referred to as an "array" or "microarray"). In one such embodiment, the invention provides a method for detecting the presence of a target molecule suspected of being contained in a test mixture, wherein said target molecule to be detected is a protein, the method comprising:
 a) providing a biochip comprising a solid support, said solid support comprising a plurality of spatially defined addresses, each said address comprising at least one copy of a single species of nucleic acid ligand attached thereto, each said species of nucleic acid ligand having specific affinity for one of said target molecules suspected of being contained in said test mixture, and each said species of nucleic acid ligand binding specifically to said target molecule through non-Watson-Crick interactions;
 b) contacting said biochip with said test mixture suspected of containing said target molecule;
 c) removing non-specifically bound material from said biochip;
 d) contacting said solid support with a Universal Protein Stain (UPS), said UPS comprising one or more reagents that label proteins with a detectable moiety; and
 e) detecting the presence of said target molecule by detecting the presence of said detectable moiety at the appropriate address on said biochip.

In a related embodiment, the invention provides a method for detecting the presence of a target molecule suspected of being contained in a test mixture, wherein said target molecule be to detected is a protein, the method comprising;
 a) providing a biochip comprising a solid support, said solid support comprising a plurality of spatially defined addresses, each said address comprising at least one copy of a single species of nucleic acid ligand attached thereto, each said species of nucleic acid ligand having specific affinity for one of said target molecules suspected of being contained in said test mixture, each said species of nucleic acid ligand binding specifically to said target molecule through non-Watson-Crick interactions, and wherein said nucleic acid ligand having specific affinity for said target molecule to be detected is a photoreactive nucleic acid ligand;
 b) contacting said biochip with said test mixture suspected of containing said target molecule, wherein a nucleic acid ligand-target molecule complex is formed if said target molecule is present;
 c) irradiating said biochip, wherein said nucleic acid ligand-target molecule complex photocrosslinks;
 d) removing non-specifically bound material from said biochip;
 e) contacting said biochip with a reagent that reacts covalently with proteins and not with nucleic acids; and
 f) detecting the presence of said target molecule by detecting the presence of said detectable moiety at the appropriate address on said biochip.

Using these methods, a single UPS can be used to detect all target proteins that have bound to nucleic acid ligands (both photocrosslinking and non-photocrosslinking) on the array.

In another aspect, the invention provides a biochip comprising an array of a plurality of nucleic acid ligands attached to a solid support, wherein a plurality of said nucleic acid ligands are specifically associated with a target molecule through non-Watson-Crick interactions, and wherein said target molecules are labeled with a detectable moiety.

In another aspect, the invention provides a method for simultaneously measuring the dose-response characteristics of a plurality of species of photocrosslinking nucleic acid ligands, each said species of photocrosslinking nucleic acid ligands having specific affinity for a cognate target protein, the method comprising:
 a) providing a plurality of arrays, each said array comprising a plurality of spatially defined addresses, each said address having at least one copy of a single species of photocrosslinking nucleic acid ligand attached thereto;
 b) providing a plurality of target protein mixtures, wherein each mixture comprises a unique target protein concentration profile;
 c) contacting each said array with a different one of said mixtures; and d) measuring the amount of target protein bound to each said address on each said array;
whereby the dose-response characteristics of each said species of photocrosslinking nucleic acid ligands are measured simultaneously.

Preferably, each said target protein is absent from at least one of the target protein mixtures. The target protein concentration profiles are preferably further configured such that for each pairwise combination of said cognate target proteins, at least one target protein mixture comprises the first member of the pairwise combination at a concentration that is at least one order of magnitude higher than the second member of the pairwise combination and at least one target protein mixture comprises the first member of the pairwise combination at a concentration that is at least one order of magnitude lower than the second member of the pairwise combination. More preferably, the target protein concentration profiles are configured such that for each pairwise combination of said cognate target proteins, at least one target protein mixture comprises the first member of the pairwise combination at a concentration that is at least two orders of magnitude higher than the second member of the pairwise combination and at least one target protein mixture comprises the first member of the pairwise combination at a concentration that is at least two orders of magnitude lower than the second member of the pairwise combination.

The methods provided by the invention allow one simultaneously to: (1) evaluate the performance (dynamic range) of a plurality of photocrosslinking nucleic acid ligands; and (2) assess the specificity of each photocrosslinking nucleic acid ligand for its cognate target protein. Photocrosslinking nucleic acid ligands with the most desirable properties can then be selected for use in diagnostic and prognostic medical assays.

In another aspect, the invention provides a method for attaching a nucleic acid ligand to a solid support comprising:
  a) derivatizing said nucleic acid ligand with a poly(ethylene glycol) (PEG);
  b) attaching said PEG to said solid support.
Preferably the PEG in step a) is vinyl sulfone-PEG, and the solid support comprises thiol groups.

In yet another aspect, the present invention provides a photocrosslinking nucleic acid ligand to Human Immunodeficiency Virus (HIV) gp120MN.

BRIEF DESCRIPTION OF THE DRAWINGS

FIG. 8 illustrates the layout of a photocrosslinking nucleic acid array. Each feature is spotted three times in succession.

FIG. 14 illustrates the layout of a photocrosslinking nucleic acid array.

FIG. 18 illustrates dose-response curves for VEGF, endostatin, and catalase in 5% serum on Accelr8 slide surfaces. The individual plots are of log [protein, M] versus log RFU.

DETAILED DESCRIPTION OF THE PREFERRED EMBODIMENTS

Definitions

Figure 1:
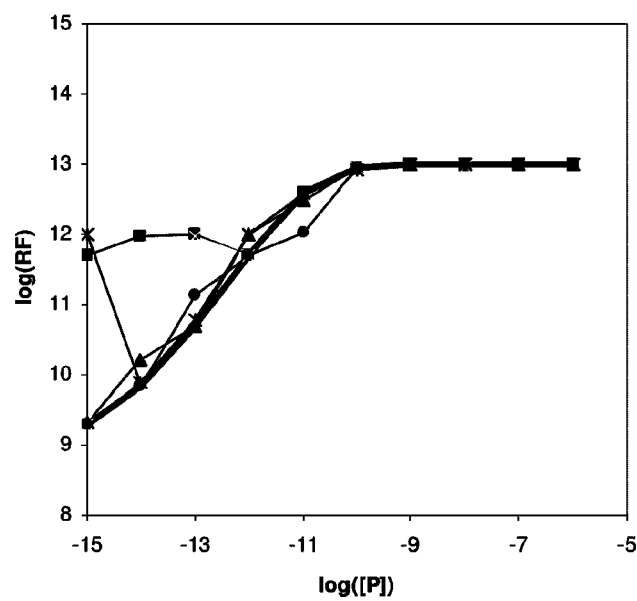
FIG. 1 illustrates a predicted assay response for different target protein mixtures (shown as a plot of log ([P]) vs log Relative Fluorescence (RF). The heavy curve is the response expected with no cross-reactivity. The responses for non-specific interactions for proteins 1-5 are shown by the marked curves.

Various terms are used herein to refer to aspects of the present invention. To aid in the clarification of the description of the components of this invention, the following definitions are provided:

As used herein, "nucleic acid ligand" is a non-naturally occurring nucleic acid having a desirable action on a target. Nucleic acid ligands are also sometimes referred to in this application as "aptamers." A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids, whereby nucleic acid ligands of the target molecule are identified.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. Modified nucleotides, such as nucleotides with photoreactive groups, can be incorporated into the candidate mixture. In addition, a candidate mixture can be produced by a prior SELEX process e.g., a first SELEX process experiment can be used to produce a ligand-enriched mixture of nucleic acids that is then used as the candidate mixture in a second SELEX process experiment. A candidate mixture can also comprise nucleic acids with one or more common structural motifs. For example, U.S. Provisional Patent Application Ser. No. 60/311,281, filed Aug. 9, 2001, entitled "Nucleic Acid Ligands With Intramolecular Duplexes" and incorporated herein by reference in its entirety, describes candidate mixtures comprising nucleic acids with intramolecular duplexes formed between their 5' and 3' ends.

In a preferred embodiment, each nucleic acid has fixed sequences surrounding a randomized region to facilitate the amplification process. As detailed in the automated SELEX process applications, the candidate mixture nucleic acids can further comprise fixed "tail" sequences at their 5' and 3' termini to prevent the formation of high molecular weight contaminants of the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. The SELEX methodology is described in the SELEX patent applications. In some embodiments of the SELEX process, aptamers that bind non-covalently to their targets are generated. In other embodiments of the SELEX process, aptamers that bind covalently to their targets are generated.

As used herein, "Universal Protein Stain" or "UPS" refers to a reagent or reagents that labels proteins and not nucleic acids with a detectable moiety.

As used herein, "target protein concentration profile" refers to the description of the concentrations of individual target proteins present in a mixture of said target proteins. In preferred embodiments of the invention, for a particular collection of target proteins a plurality of target protein mixtures is produced, each mixture comprises a unique target protein concentration profile. If a specific target protein in the collection is absent from one of the mixtures, then the target protein concentration profile for that mixture will include the value 0 M for that target protein.

"SELEX target" or "target molecule" or "target" refers herein to any compound upon which a nucleic acid can act in a predetermined desirable manner. A SELEX target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, etc., without limitation. Virtually any chemical or biological effector would be a suitable SELEX target. Molecules of any size can serve as SELEX targets. A target can also be modified in certain ways to enhance the likelihood of an interaction between the target and the nucleic acid. Embodiments of the SELEX process in which the target is a peptide are described in U.S. patent application Ser. No. 09/668,602, filed Sep. 22, 2000, entitled "Modified SELEX Processes Without Purified Protein," incorporated herein by reference in its entirety.

"Tissue target" or "tissue" refers herein to a certain subset of the SELEX targets described above. According to this definition, tissues are macromolecules in a heterogeneous environment. As used herein, tissue refers to a single cell type, a collection of cell types, an aggregate of cells, or an aggregate of macromolecules. This differs from simpler SELEX targets which are typically isolated soluble molecules, such as proteins. In the preferred embodiment, tissues are insoluble macromolecules which are orders of magnitude larger than simpler SELEX targets. Tissues are complex targets made up of numerous macromolecules, each macromolecule having numerous potential epitopes. The different macromolecules which comprise the numerous epitopes can be proteins, lipids, carbohydrates, etc., or combinations thereof. Tissues are generally a physical array of macromolecules that can be either fluid or rigid, both in terms of structure and composition. Extracellular matrix is an example of a more rigid tissue, both structurally and compositionally, while a membrane bilayer is more fluid in structure and composition. Tissues are generally not soluble and remain in solid phase, and thus partitioning can be accomplished relatively easily. Tissue includes, but is not limited to, an aggregate of cells usually of a particular kind together with their intercellular substance that form one of the structural materials commonly used to denote the general cellular fabric of a given organ, e.g., kidney tissue, brain tissue. The four general classes of tissues are epithelial tissue, connective tissue, nerve tissue and muscle tissue.

Examples of tissues which fall within this definition include, but are not limited to, heterogeneous aggregates of macromolecule such as fibrin clots which are acellular; homogeneous or heterogeneous aggregates of cells; higher ordered structures containing cells which have a specific function, such as organs, tumors, lymph nodes, arteries, etc.; and individual cells. Tissues or cells can be in their natural environment, isolated, or in tissue culture. The tissue can be intact or modified. The modification can include numerous changes such as transformation, transfection, activation, and substructure isolation, e.g., cell membranes, cell nuclei, cell organelles, etc. Sources of the tissue, cell or subcellular structures can be obtained from prokaryotes as well as eukaryotes. This includes human, animal, plant, bacterial, fungal and viral structures.

As used herein, "solid support" is defined as any surface to which molecules may be attached through either covalent or non-covalent bonds. This includes, but is not limited to, membranes, plastics, paramagnetic beads, charged paper, nylon, Langmuir-Bodgett films, functionalized glass, germanium, silicon, PTFE, polystyrene, gallium arsenide, gold and silver. Any other material known in the art that is capable of having functional groups such as amino, carboxyl, thiol or hydroxyl incorporated on its surface, is also contemplated. This includes surfaces with any topology, including, but not limited to, spherical surfaces, grooved surfaces, and cylindrical surfaces e.g., columns. Multiple nucleic acid ligands, each specific for a different target, may be attached to specific locations ("addresses") on the surface of a solid support in an addressable format to form an array, also referred to as a "microarray" or as a "biochip." By way of non-limiting example only, an array may be formed with a planar solid support, the surface of which is attached to nucleic acid ligands. By way of non-limiting example only, an array may be also be formed by attaching nucleic acid ligands to beads, and then placing the beads in an array format on another solid support, such as a microtiter plate.

"Partitioning" means any process whereby ligands bound to target molecules can be separated from nucleic acids not bound to target molecules. More broadly stated, partitioning allows for the separation of all the nucleic acids in a candidate mixture into at least two pools based on their relative affinity to the target molecule. Partitioning can be accomplished by various methods known in the art. Nucleic acid-protein pairs can be bound to nitrocellulose filters while unbound nucleic acids are not. Columns which specifically retain nucleic acid-target complexes can be used for partitioning. For example, oligonucleotides able to associate with a target molecule bound on a column allow use of column chromatography for separating and isolating the highest affinity nucleic acid ligands. Beads upon which target molecules are conjugated can also be used to partition nucleic acid ligands in a mixture. If the beads are paramagnetic, then the partitioning can be achieved through application of a magnetic field. Surface plasmon resonance technology can be used to partition nucleic acids in a mixture by immobilizing a target on a sensor chip and flowing the mixture over the chip, wherein those nucleic acids having affinity for the target can be bound to the target, and the remaining nucleic acids can be washed away. Liquid-liquid partitioning can be used as well as filtration gel retardation, and density gradient centrifugation.

As used herein, "PhotoSELEX" is an acronym for Photochemical Systematic Evolution of Ligands by EXponential enrichment, and refers to embodiments of the SELEX process in which photocrosslinking nucleic acid ligands (also referred to as "photoaptamers" or "photocrosslinking aptamers") are generated. In the photoSELEX process, a photoreactive nucleotide activated by absorption of light is incorporated in place of a native base in either RNA- or in ssDNA-randomized oligonucleotide libraries, the nucleic acid target molecule mixture is irradiated causing some nucleic acids incorporated in nucleic acid-target molecule complexes to crosslink to the target molecule via the photoreactive functional groups, and the selection step is a selection for photocrosslinking activity. The photoSELEX process is described in great detail in the PhotoSELEX Process Applications.

The SELEX patent applications and the PhotoSELEX Process Applications describe and elaborate on the aforementioned processes in great detail. Included are targets that can be used; methods for the preparation of the initial candidate mixture; methods for partitioning nucleic acids within a candidate mixture; and methods for amplifying partitioned nucleic acids to generate enriched candidate mixtures. The SELEX patent applications and the PhotoSELEX Process Applications also describe ligand solutions obtained to a number of target species, including protein targets wherein the protein is or is not a nucleic acid binding protein.

Note that throughout this application, various publications, publications, and patent applications are mentioned; each is incorporated by reference to the same extent as if each was specifically and individually incorporated by reference.

Multiplexed Evaluation of Photocrosslinking Nucleic Acid Ligands

In one embodiment of the invention, photocrosslinking nucleic acid ligands that are identified as possessing potentially useful affinity and photocrosslinking activity are rapidly assayed using a multiplexed assay on a nucleic acid ligand array, also referred to herein interchangeably as a "microarray" or "biochip." Nucleic acid ligands can be immobilized onto a wide variety of solid support surfaces that can be used in assay protocols including, but not limited to, the following formats: microtiter wells, microscope slides, silicon wafer chips, flow through chips, and microbeads. Methods for immobilizing nucleic acids on solids supports are well known in the art.

For each protein target, one or more identified photocrosslinking nucleic acid ligands can be immobilized to discrete addresses on the array. A plurality of identical arrays is preferably constructed, and then each individual array can be contacted with the analyte solution (for example, a mixture of protein targets (also herein referred to as a "cocktail") or a biological fluid, including, but not limited to, serum, tissue culture supernatant, urine, and tissue homogenate). The array can be used to either (1) test the multiplexed performance of the nucleic acid ligand; or (2) assay a sample for analyte protein concentration. If the arrays are used to test multiplexed performance of the nucleic acid ligand, then each protein target for which a corresponding photocrosslinking nucleic acid ligand is present on the array is included in the target protein mixtures that are incubated with the array.

Following the incubation of the analyte with the microarray, the photocrosslinking nucleic acid ligands are photocrosslinked to their cognate protein targets, and the arrays are washed under stringent conditions in order to remove non-specifically bound proteins. Protein binding by the arrays can the be quantified by using a Universal Protein Stain (UPS) as described below in the section entitled "Universal Protein Stains." Examples 3 and 4 provide exemplary methods for processing the multiplexed arrays.

The multiplex assays described herein allow a two-fold evaluation of photocrosslinking nucleic acid ligands by allowing one to: (1) evaluate the performance (dynamic range) of a photocrosslinking nucleic acid ligand in the array format and (2) assess its specificity for the cognate target protein. If the arrays are used to assess the performance of nucleic acid ligands, mixtures of target proteins can be produced, each mixture having a different target protein concentration profile, and the mixtures may be used as samples to contact the arrays. By varying the absolute concentrations of each protein, it is possible to obtain a dose-response curve for each photocrosslinking nucleic acid ligand. It is possible to evaluate simultaneously the specificity of each photocrosslinking nucleic acid ligand. The multiplexed assays can also be performed in the presence and absence of serum in order to further screen for non-specific interactions. In this way, it is possible to evaluate simultaneously many photocrosslinking nucleic acid ligands on a single series of arrays. Photocrosslinking nucleic acid ligands with the most desirable properties can then be selected for use in diagnostic and prognostic medical assays.

The multiplexed assays of the invention allow for dramatic streamlining of the photocrosslinking nucleic acid ligand evaluation process, saving both time and resources. For example, running separate assays for each photocrosslinking nucleic acid ligand would require, say, 10 measurements each in buffer and serum. To evaluate 5 photocrosslinking nucleic acid ligands to each of 100 different proteins would require 2×10×5×100=10,000 experiments. A multiplex assay can simultaneously measure 500 photocrosslinking nucleic acid ligand responses to target protein mixtures ("cocktails"). Measurement of 10 target protein mixtures, each having a specific target protein concentration profile, both in buffer and serum, requires only 20 experiments and will provide the same data as 10,000 experiments plus yield additional information about specificity.

In one non-limiting example of this embodiment of the invention, the dynamic ranges of a single photocrosslinking nucleic acid ligand is assessed by collecting data for 9 different protein concentrations in target protein mixtures starting at $10^{-6}$ M and decreasing a log in concentration to $10^{-14}$ M. A tenth target protein mixture will contain no cognate protein i.e., the target protein concentration profile for that mixture will be 0 M. It will be apparent to those skilled in the art that the exact number and ranges of these can be adjusted for more suitable limits. For a highly multiplexed assay, it may be desirable to evaluate the dynamic range of 100 or more different proteins simultaneously, so at least ten target protein mixtures are required as in the single ligand case. For example, for photocrosslinking nucleic acid ligands with negligible non-specific binding, one can make ten target protein mixtures where the first ten target proteins are absent in the first target protein mixture, the next ten target proteins are present at the lowest concentration in the range and so on, with the last ten target proteins at the highest concentration. The next target protein mixture could then have the first ten target proteins at the lowest concentration, the next ten at the second lowest, and so on, with the last 10 target proteins absent in this target protein mixture. Repeating this pattern eight more times would result in 10 complex target protein mixtures, each having a unique target protein concentration profile. Each target protein would sample the entire concentration range desired. Although this strategy could potentially measure the dynamic range of 100 different protein targets, a different protein distribution strategy will simultaneously yield specificity data as well.

Non-specific binding/crosslinking and interference is a possibility in multiplexed assays, although the unique characteristics of photocrosslinking nucleic acid ligands reduce this to an extremely low level compared to other reagents used in diagnostic chip-based assays. In order to minimize further the likelihood of such effects in multiplexed assays, it is desirable to detect these effects and eliminate those photocrosslinking nucleic acid ligands that demonstrate crosslinking to noncognate proteins (or at least minimize such effects by proper photocrosslinking nucleic acid ligand choice). In one embodiment of the invention, this may be achieved by appropriate configuration of the target protein concentration profiles of the individual target protein mixtures. Since any protein in a target protein mixture may affect the signal of any other protein, in preferred embodiments each pairwise combination of target proteins is tested in varying concentrations across all of the protein target mixtures—some high with respect to the first protein and some high with respect to the second since photocrosslinking nucleic acid ligand cross-reactivity is certainly not symmetric. For example, for ten proteins 1-10, the pairwise combinations for protein 1 would be: [1,2], [1,3], [1,4] . . . [1,10]. In especially preferred embodiments, each protein pair differs by plus and minus at least one log of concentration (i.e. at least one order of magnitude higher and lower) in some number of the target protein mixtures, more preferably by plus and minus at least two logs of concentration, and even more preferably by plus and minus at least three logs of concentration. For example, with reference to the aforementioned pairwise combination members 1 and 2, in at least one target protein test mixture, protein 1 would be present at a concentration that is two orders of magnitude higher than protein 2; and in at least one target protein mixture, protein 1 would be present at a concentration that is at least two orders of magnitude lower than protein 2. This will ensure that one can detect cross-reactivity in the evaluation assays. In addition, this constraint on target protein mixture composition will also require that no two proteins have the same concentration in any two target protein mixtures.

Consider ten proteins 1-10 present at ten different concentrations in ten target protein mixtures A-J. For the first protein there are 10!=3628800 ways to distribute the ten concentrations among ten target protein mixtures. There are 10!−1 ways for the second since it cannot have the same distribution among the protein mixtures as the first, and so on. A key aspect of configuring the target protein concentration profiles should be related to maximizing the difference in distributions for each of the 100 proteins, as described above. Table 1 below enumerates exemplary target protein concentration profiles in the ten resulting target protein mixtures A-J. For example protein 1 is absent from the mixture A, has a concentration of $10^{-11}$ in the mixture B, $10^{-9}$ in the mixture C, etc. The target protein concentration profiles displayed in the table ensures that each protein pair has concentrations separated by three logs, both plus and minus, at least twice in the ten target protein mixtures. For instance, in mixture A, protein 6 is at least three logs less than proteins 10, 8, 9, 2, 7, and 5. In mixture E protein 6 is at least three logs higher than proteins 5, 10, 8, 7, and 4.

TABLE 1

Exemplary target protein concentration profiles

| Mixture | Target Protein Concentration Profiles (M) | | | | | | | | | |
|---|---|---|---|---|---|---|---|---|---|---|
| | 0 | $10^{-14}$ | $10^{-13}$ | $10^{-12}$ | $10^{-11}$ | $10^{-10}$ | $10^{-9}$ | $10^{-8}$ | $10^{-7}$ | $10^{-6}$ |
| A | 1 | 6 | 4 | 3 | 10 | 8 | 9 | 2 | 7 | 5 |
| B | 2 | 7 | 5 | 4 | 1 | 9 | 10 | 3 | 8 | 6 |
| C | 3 | 8 | 6 | 5 | 2 | 10 | 1 | 4 | 9 | 7 |
| D | 4 | 9 | 7 | 6 | 3 | 1 | 2 | 5 | 10 | 8 |
| E | 5 | 10 | 8 | 7 | 4 | 2 | 3 | 6 | 1 | 9 |
| F | 6 | 1 | 9 | 8 | 5 | 3 | 4 | 7 | 2 | 10 |
| G | 7 | 2 | 10 | 9 | 6 | 4 | 5 | 8 | 3 | 1 |
| H | 8 | 3 | 1 | 10 | 7 | 5 | 6 | 9 | 4 | 2 |
| I | 9 | 4 | 2 | 1 | 8 | 6 | 7 | 10 | 5 | 3 |
| J | 10 | 5 | 3 | 2 | 9 | 7 | 8 | 1 | 6 | 4 |

Out of 3,628,800 possible target protein concentration profiles, it is possible to find 100 that provide the best chance of revealing cross-reactivity of proteins for non-cognate photocrosslinking nucleic acid ligands. These distributions are generated using Monte Carlo techniques, by randomly sampling distributions and accepting only those that satisfy the criteria of having multiple comparisons between each pair of proteins. Maximizing the number of times one measures a cognate protein in the presence of excess "background" proteins will provide a reasonable test of specificity. In the absence of significant cross-reactivity a reasonable standard curve will be generated. Spikes in these curves at low cognate protein levels, or losses in sensitivity will be indicative of cross-reactivity.

In the absence of any non-specific binding or interference, multiplexed evaluation assays performed according to the aforementioned methods will produce standard curves for each photocrosslinking nucleic acid ligand, wherein each curve will reveal the dynamic range of the photocrosslinking nucleic acid ligand. In order to determine the effect of non-specific binding, the present invention now provides a model to evaluate the fraction of the complex mixture that binds to each photocrosslinking nucleic acid ligand.

The model is based on a standard treatment of equilibrium binding according to the following equation:

$$P_i + L_j \rightleftharpoons P_i{:}L_j \quad K_{ij} = [P_i{:}L_j]/[P_i][L_j] \tag{1}$$

where $[P_i]$ is the concentration of unbound protein analyte i (i varies from 1 to 100) in the sample, $[L_j]$ is the concentration of unbound photocrosslinking nucleic acid ligand j (j varies from 1 to 500, i.e., there are five photocrosslinking nucleic acid ligands for each protein measured in one assay) on the chip, $[P_i{:}L_j]$ is the concentration of immobilized protein/photocrosslinking nucleic acid ligand complex, and $K_{ij}$ is the equilibrium association constant for the reaction. If there was no nonspecific binding the matrix of association constants K is diagonal for a protein chip in which there is only one photocrosslinking nucleic acid ligand per protein; off diagonal entries indicate cross-reactivity and most likely have association constants several logs lower than the specific (diagonal) interaction term. The mass balance equations, in terms of total protein and photocrosslinking nucleic acid ligand concentrations, are $$[P_i]_{total} = [P_i] + \Sigma_j [P_i{:}L_j] = [P_i](1 + \Sigma_j K_{ij}[L_j]) \tag{2}$$

$$[L_j]_{total} = [L_j] + \Sigma_i [P_i{:}L_j] = [L_j](1 + \Sigma_i K_{ij}[P_i]) \tag{3}$$

where the second equality is obtained by substituting $[P_i]K_{ij}[L_j]$ for $[P_i{:}L_j]$ (see Eq. (1)). Substitution of Eq. (3) into Eq. (2) yields a system of equations for the free protein concentrations $$[P_i] = [P_i]_{total}(1 + \Sigma_j K_{ij}[L_j]_{total}/(1 + \Sigma_k K_{kj}[P_k]))^{-1} \tag{4}$$

The system of equations can be solved iteratively to self-consistency in the free protein concentrations $[P_i]$. The concentrations of the bound photocrosslinking nucleic acid ligands are then calculated with the following $$[P_i{:}L_j] = [P_i]K_{ij}[L_j]_{total}/(1 + \Sigma_k K_{kj}[P_k]))^{-1} \tag{5}$$

The washing and crosslinking will reduce the amount of protein detected from that originally bound. The fraction of loss due to washing will depend on the off rate of the individual complexes; high affinity interactions with slow off rates will lose little specific bound protein whereas non-specific binders should be substantially reduced. The crosslinking efficiencies for aptamers recovered from an enriched pool will certainly vary from 0-100%; it is possible to eliminate the non-crosslinking photocrosslinking nucleic acid ligands since they will not remain on the array following the harsh washing. Finally, each protein will produce a signal proportional to the number of stain molecules that specifically bind to the captured proteins, for example, as a function of the number of lysines contained in the protein and their reactivity.

For the following discussion, washing and crosslinking losses, as well as the stain signal enhancement will be treated as a factor unique to each complex. The final signal measured for each photocrosslinking nucleic acid ligand on the array is given as $$RF_j = \Sigma_i f_{ij}[P_i{:}L_j] + b \tag{6}$$

where $RF_j$ is the relative fluorescence measured for photocrosslinking nucleic acid ligand j, $f_{ij}$ accounts for the washing, crosslink efficiency, and staining of each protein/photocrosslinking nucleic acid ligand complex $P_i{:}L_j$, and b is the instrument background that sets the absolute lower limit of detection.

This completes the model. Using the ten target protein mixtures defined above as an example, one can explore the proposed assay qualitatively. To illustrate, consider one photocrosslinking nucleic acid ligand at a concentration of $10^{-11}$ M with a target protein specific interaction $K_{ij} = 10^{11}$ M$^{-1}$ (Kd=10 pM) and $f_{ij}/b = 5.0 \times 10^{13}$ (this is somewhat arbitrary and only affects the lower limit of detection—saturation of the photocrosslinking nucleic acid ligand sets the upper limit here). FIG. 1 illustrates the assay response for the different target protein mixtures (shown as a plot of log ([P]) vs log Relative Fluorescence (RF). The heavy curve is the response expected with no cross-reactivity. The responses for non-specific interactions for proteins 1-5 are shown by the marked curves. With no cross-reactivity to background proteins, the heavy curve in FIG. 1 would be the expected response curve. The linear region is roughly from $10^{-14}$ to $10^{-11}$, four logs of protein concentration. The saturation here is primarily set by the photocrosslinking nucleic acid ligand concentration.

To explore the behavior of the response in the presence of a single non-specific interaction, nine curves were generated, one for each of the other proteins in the target protein mixtures; only one protein was allowed to cross-react in each simulation. For the same photocrosslinking nucleic acid ligand as above, the nonspecific interaction was set three logs less than the specific one, $K_{ij}=10^8$ $M^{-1}$ (Kd=10 nM), and $f_{ij}/b=5.0\times10^{12}$, ten percent of the specific. The same target protein mixtures were used in each calculation. FIG. 1 contains five curves (proteins 1-5) and the remaining four (proteins 6-9) are displayed in FIG. 2. Again, in FIG. 2 the heavy curve is the response expected with no cross-reactivity. The responses for non-specific interactions with proteins 6-9 are shown by the marked curves.

Since the data are plotted on a log/log scale the deviations from linearity due to the non-specific interactions are usually quite apparent. Two curves display deviations that may be difficult to discern in the presence of noise, but that is entirely a consequence of the target protein mixtures used here; further enhancements can be achieved by a more careful choice of protein mixtures.

Figure 2:
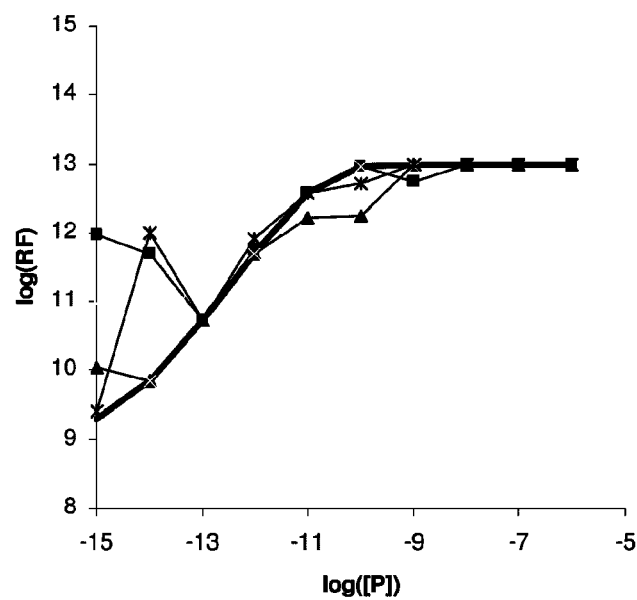
FIG. 2 illustrates the assay response for different target protein mixtures (shown as a plot of log ([P]) vs log Relative Fluorescence (RF). The heavy curve is the response expected with no cross-reactivity. The responses for non-specific interactions for proteins 6-9 are shown by the marked curves.

FIG. 1 and FIG. 2 show that most non-specific binding/crosslinking can result in positive deviations from linearity, however some combinations of protein concentrations will result in a loss of specific signal when the non-specific protein is in great excess over the cognate protein—competing for sites that would otherwise be occupied.

The model provided herein shows that the dynamic range and potential non-specific interactions of photocrosslinking nucleic acid ligands in a multiplexed evaluation assay can be obtained from a set of 10 measurements. It is important to note that there is no restriction on using ten target protein mixtures—twenty could be used to ensure more comparisons at low levels of cognate protein to every other protein in the mixture to maximize the detection of non-specific interactions. Doubling the number of experiments would not compromise the efficiency of the approach. Crossreactivity of photocrosslinking nucleic acid ligands is assessed for every target protein in the target protein mixtures.

Array Synthesis

Many surface attachment chemistries may be used for nucleic acid ligand immobilization including, but not limited to: thiol-modified nucleic acid ligands bound to thiol-reactive surfaces including gold; acrydite-modified nucleic acid ligands bound to thiol containing surfaces; biotinylated nucleic acid ligands bound to streptavidin surfaces; amine-modified nucleic acid ligands bound to carboxylate, isothiocyanate, N-hydroxy-succinimide, or epoxide-activated surfaces. A wide variety of surface coatings have been demonstrated for nucleic acid ligand arrays including: epoxide on glass, epoxide on silicon, Accelr8 N-hydroxy-succinimide-activated organic polymer, Surmodics N-hydroxy-succinimide-activated acrylamide polymer, Rosatech amine-reactive organic polymer, gold coated with organic self-assembled monolayers (SAMs), and Matrix thiol-containing acrylamide polymer.

Printing (also referred to as "spotting") buffer components that are routinely evaluated in initial screens include buffer ($NaPO_4$, $NaBO_4$, $NaCO_3$ are commonly used), detergent (sarkosyl, Tween20, and SDS), hydrophilic additives (PEG, Me-PEG, glycerol), and organic solvents (dimethyl sulfoxide (DMSO), dimethylformamide (DMF), N-methylpyrrolidone (NMP)).

Following printing of the nucleic acid ligands onto the modified surface, in preferred embodiments post printing treatments are carried out to eliminate residual functional groups and to modify the environment around the nucleic acid ligand features. Typical post-printing treatments carried out to cap residual functionality on the surface include alkaline washes to hydrolyze labile groups and acetylation of primary amines or free sulfhydryls.

Additional post printing treatments can include the reaction of surface functional groups with alkyl or polyethylene glycol chains to modify the environment around the nucleic acid ligands themselves (see Example 5 below). For example, in some embodiments, poly(ethylene glycol) (PEG) spacers are inserted between the nucleic acid ligands and the surface of the solid support. It has been found by the inventors that PEG spacers promote specific protein binding activity by the nucleic acid ligands in microarrays. Similarly, the use of PEG molecules cospotted with nucleic acid ligands to create an array promotes the specific binding activity of the nucleic acid ligands in microarrays. Without being limited by a single theory or hypothesis, it is believed that the PEG molecule minimizes denaturation and improves specific activity of the nucleic acid ligand by providing a long, flexible, neutrally charged and hydrophilic spacer between each nucleic acid ligand and surface of the array.

Specifically, the conjugation of bifunctional linkers that include, but are not limited to, PEG spacers (and may also include fluoro compounds) to 5'-derivatized nucleic acid ligands facilitates the attachment to the surface, and also moves the nucleic acid ligand to a more hydrophilic environment removed from the substrate itself. Surface-specific inactivation effects are observed for some nucleic acid ligands in the absence of PEG spacers and protein binding activity has been regained when the PEG spacer is used for the nucleic acid ligand immobilization. PEG polymers, co-spotted on the surface, have been used to reduce non specific interactions on various surfaces. Methods and reagents for coupling PEG molecules to nucleic acids and to solid supports are well known in the art. For example, NHS-PEG-vinyl sulfone may be reacted with a 5' amine derivatized nucleic acid ligand, leading to coupling of the PEG vinyl-sulfone moiety to the nucleic acid ligand. The resulting vinyl sulfone-PEG nucleic acid ligands may then be coupled to a solid support that is labeled with thiol groups.

It will be understood that the aforementioned methods for array synthesis can be used with both photocrosslinking nucleic acid ligands and with non-photocrosslinking nucleic acid ligands.

Example 5 provides an exemplary protocol for PEGylation of nucleic acid ligands.

Photoaptamer Assay Protocols

The present invention provides methods for designing multiplexed assays that employ arrays of photocrosslinking nucleic acid ligands. Exemplary methods for processing those multiplexed arrays are now provided.

In preferred embodiments of the invention, multiplexed detection of protein target binding to an array of photocrosslinking nucleic acid ligands is carried out by first equilibrating the arrays with SELEX buffer, a blocking nucleic acid, such as tRNA, and a blocking protein, such as methylated casein carrier. Protein analyte is incubated with the surface, preferably for enough time to approach equilibrium (either under static conditions or with flow across the array surface). To ensure minimal noncognate protein background, the affinity-bound proteins are preferably washed with buffer, most preferably SELEX buffer (40 mM HEPES, pH 7.5, 111 mM NaCl, 5 mM KCl, 1 mM $MgCl_2$, 1 mM $CaCl_2$, 0.05% TWEEN-20), to remove noncognate, low affinity proteins from the array. In some embodiments, this pre-crosslinking wash is carried out at increased ionic strength to increase the likelihood of disrupting such non-specific interactions.

The array is then exposed to UV light (preferably at 308 nm from a monochromatic light source, or using wavelengths above 312 nm, selected by applying a cutoff filter to a mercury lamp) to photocrosslink nucleic acid ligands that have bound to their cognate protein target. Preferably, crosslinking is carried out with a thin layer of aqueous buffer over the array surface.

Most preferably, the array is then washed harshly under conditions that denature nucleic acids and/or proteins. Suitable harsh conditions are achieved by combinations of, for example, salt (for example 20 mM $NaH_2PO_4$, pH 7.4, 150 mM NaCl, 0.1% SDS, 1 mM EDTA), detergent, hydroxide (for example 20 mM NaOH), acid, chaotropic agents (for example 8M urea), heat (for example 40° C.), and flow. The harshness of the washing is limited only by the ability of the organic surface coating to maintain structural integrity. The immobilization chemistries provided above and the photocrosslinks themselves are both stable to such washes.

Following the harsh washing of the slide to remove non-specifically bound protein, the array is stained with a UPS in order to label all proteins with a detectable moiety. To minimize background signals, in preferred embodiments the array is again washed harshly following the UPS treatments. The array is then "read" by quantifying the signal from the detectable moiety. In preferred embodiments, a standard microarray fluorescent reader with the appropriate excitation source and filters is used.

Universal Protein Stains

A Universal Protein Stain (UPS) comprises a reagent or reagents that label all proteins with a detectable moiety but does not label nucleic acids or other components of an array, such as the derivatized surface used to immobilize the nucleic acid ligands. The detectable moiety may be detected via fluorescent, chemiluminescent signal or any other quantifiable signal depending on its identity. It is preferred, but not required, that at least one of the UPS reagents reacts covalently with the protein. Any reactive chemical group found on proteins, but not found on nucleic acids or the slide substrate, can serve as the site of covalent attachment. In the detection of protein targets, these groups include, but are not limited to, primary amines (lysine), thiols (cysteine, which may be produced by the reduction of disulfide linkages), alcohols (serine, threonine, tyrosine and sugar moieties on glycoproteins (including the products of oxidation of cis diols on such sugars)), and carboxylates (glutamic and aspartic acid).

The detectable moiety may be, without limitation, a dye (most preferably a fluorophore), a radiolabel, a quantum dot, an enzyme, an enzyme substrate, or any other substance that may be used in any manner to generate a quantifiable signal. In the case where the detectable moiety is an enzyme (for example, alkaline phosphatase), the quantifiable signal may be generated in the presence of the enzyme substrate and any additional factors necessary for enzyme activity. In the case where the detectable moiety is an enzyme substrate the quantifiable signal may be generated in the presence of the enzyme and any additional factors necessary for enzyme activity. Suitable reagent configurations for attaching the detectable moiety to the protein include, but are not limited to, covalent attachment of the detectable moiety to the protein, non-covalent association of the detectable moiety with another UPS component that is covalently attached to the proteins, and covalent attachment of the detectable moiety to a UPS component that is non-covalently associated with the protein.

In its most basic embodiment, the UPS is a single chemical reagent that reacts covalently with functional groups unique to proteins and in doing so covalently attaches the detectable moiety to the protein. Preferred UPSs according to this embodiment comprise dyes with groups capable of reacting covalently with functional groups that are unique to proteins. Such groups may be added to the dyes by derivatization, or may be present on the unmodified dye. N-hydroxysuccinimide-activated dyes (also known as NHS-activated dyes) react with amine groups, and are especially preferred UPSs. Another especially preferred UPS is CBQCA (3-(4-carboxybenzoyl)quinoline-2-carboxaldehyde) which also reacts with amines in the presence of cyanide or thiols to form highly fluorescent isoindoles. Other amine reactive groups suitable for use in UPS reagents include, but are not limited to, isocyanates, isothiocyanates, acyl azides, sulfonyl chlorides, aldehydes, 4-sulfo-2,3,5,6-tetrafluorophenol (STP) esters, and arylating agents such as NBD (7-nitrobenz-2-oxa-1,3-diazole) chloride, NBD fluoride, and dichlorotriazines.

In some embodiments, the UPS comprises a plurality of reagents. For example, the UPS can comprise a first reagent that reacts covalently with the proteins, and one or more further reagents that attach the detectable moiety, either directly or indirectly, covalently or non-covalently, to the protein via a chemical group or other functionality introduced by the first reagent. For example, in one embodiment a suitable UPS comprises (a) a biotin derivative that reacts with proteins; and (b) a streptavidin-detectable moiety conjugate, for example a fluorescent streptavidin derivative or a streptavidin-enzyme conjugate. The biotin derivative reacts with amine groups, thereby covalently attaching biotin to proteins; the streptavidin-detectable moiety conjugate binds to the immobilized biotin groups, thereby localizing the detectable moiety to sites of protein binding on the array.

In another embodiment, a suitable UPS comprises: i) biotin or a biotin derivative, conjugated to a reactive group that is capable of covalently attaching the biotin or biotin derivative to the bound protein targets; ii) avidin and/or streptavidin; and iii) a biotin-detectable moiety conjugate, for example a fluorescent biotin derivative. Preferably, the biotin derivative in i) is an amine-reactive biotin derivative, most preferably NHS-Biotin, wherein the biotin is optionally separated from the NHS by spacer atoms (Calbiochem, Inc.). Reaction of the NHS group with primary amines on bound protein targets leads to the covalent attachment of biotin to protein targets that are bound to nucleic acid ligands on the array. The array can then be treated with the streptavidin or avidin. Since streptavidin and avidin can each bind four biotins, the addition of these proteins provides three biotin binding sites for each biotin originally coupled to the bound protein target by the NHS-biotin. The biotin-detectable moiety derivative of iii) can then be added, whereupon it binds tightly to the unoccupied biotin binding sites on the streptavidin or avidin.

In another embodiment, the UPS comprises (a) a hapten, such as dinitrophenol (DNP), that is derivatized with a group that reacts with proteins; and (b) an anti-hapten antibody conjugated to a detectable moiety, for example a fluorescent anti-hapten antibody or an enzyme-anti-hapten antibody conjugate. In still further embodiments, the UPS may comprise: (a) a hapten, such as dinitrophenol (DNP), that is derivatized with a group that reacts with proteins; and (b) an anti-hapten antibody; (c) a secondary antibody that binds to the anti-hapten antibody (for example, an antibody preparation that reacts with all immunoglobulins from the animal species used to prepare the anti-hapten antibody), which secondary antibody is conjugated to a detectable moiety.

Where the UPS comprises multiple reagents, those skilled in the art will understand that in some cases the reagents should be added sequentially, whereas in other cases they may be added together.

In another embodiment, the UPS comprises an agent for the reduction of disulfides (e.g., cysteine) to thiol groups, and further comprises a thiol-reactive compound. Suitable thiol-reactive groups that may be used in UPSs include, but are not limited to, iodoacetamides, maleimides, benzylic halides and bromomethylketones. For example, one suitable UPS according to this embodiment comprises (a) a reducing agent; and (b) a detectable moiety derivatized with a thiol-reactive group. Another example of a UPS according to this embodiment comprises (a) a reducing agent; (b) a biotin derivative that reacts with thiol groups; and (c) a streptavidin-detectable moiety conjugate.

In a further embodiment, the UPS comprises an agent for oxidizing cis-diols at protein glycosylation sites, and further comprises a compound bearing a hydrazide reactive group. For example, one suitable UPS according to this embodiment comprises: (a) an oxidizing agent for the oxidation of cis-diols in sugars; (b) a hydrazide derivative of a detectable moiety.

In another embodiment, carboxylates on protein can be reacted with a UPS comprising (a) EDC (1-(3-dimethylaminopropyl)-3-ethylcarbodiimide)/sulfo-NHS (N-hydroxysulfosuccinimide) which reacts with carboxylates to form NHS-ester groups; and (b) a detectable moiety conjugated to a group that reacts with the NHS-ester groups, for example amine group(s) or hydrazide group(s). In one such embodiment, a UPS may comprise: (a) EDC (1-(3-dimethylaminopropyl)-3-ethylcarbodiimide)/sulfo-NHS (N-hydroxysulfosuccinimide); (b) a biotin derivative with an amine group; (c) a streptavidin-enzyme conjugate or fluorescent streptavidin derivative.

Those skilled in the art will recognize that it may be necessary to "block" unreacted functional groups in certain embodiments of the invention. For example, in the example described above involving EDC (1-(3-dimethylaminopropyl)-3-ethylcarbodiimide)/sulfo-NHS (N-hydroxysulfosuccinimide), unreacted NHS-ester groups on the protein may remain after the addition of the biotin derivative with the amine group; those unreacted NHS-ester groups might then react with the enzyme, leading to its inactivation. Blocking of unreacted NHS-ester groups in this embodiment can be achieved using a small molecule with amine group, such as ethanol amine.

In some embodiments, the UPS comprises a reagent(s) that reacts with a group unique to proteins, including thiol groups produced by reduction of disulfide linkages and oxidized cis diols, and in doing so introduces a functional group into the protein. For example Traut's reagent (2-iminothiolane) and N-succinimidyl 3-[2-pyridyldithio]-propionamido (SPDP) heterobifunctional linker both react with amine groups, thereby introducing thiol groups. The newly-introduced thiol group can then be reacted with other reagents as described above in order to label the protein with a detectable moiety. For example, one suitable UPS according to this embodiment comprises: (a) Traut's reagent; and (b) a dye derivatized with a thiol-reactive group. Many other reagents for derivatizing proteins with functional groups, including homobifunctional linker and heterobifunctional linkers, are well known to those skilled in the art.

To enhance the signal achieved by staining the protein target, in some embodiments amplification may be exploited using a UPS that includes an enzyme as the detectable moiety. Amplification, a consequence of turnover of multiple substrates by each enzyme, yields better signal to noise ratios for protein quantification in systems with minimal general backgrounds. In these embodiments, the quantifiable signal is generated upon addition of the enzyme substrate and any additional factors necessary for enzyme activity. One suitable UPS for labeling proteins with an enzyme comprises (a) a biotin derivatized with a group that reacts with a group unique to proteins; and (b) a streptavidin-enzyme conjugate. Another suitable UPS comprises (a) a hapten derivative that reacts with a group unique to proteins (for example, a dinitrophenol derivative); and (b) an anti-hapten antibody which is conjugated to the enzyme.

One suitable enzyme that may be used in a UPS system according to the embodiment provided above is alkaline phosphatase, particularly when used with the soluble, non-fluorescent substrate 2-(5'-chloro-2'-phosphoryloxyphenyl)-6-chloro-4-(3H)-quinazolinone (ELF-97 phosphate). Alkaline phosphatase cleaves this substrate to produce the insoluble and fluorescent ELF alcohol which precipitates locally, thereby providing a quantifiable signal at the site of immobilization of the enzyme.

Another suitable enzyme that may be used in a UPS system according to the embodiment described above is horseradish peroxidase (HRP), particularly when used in the tyramide signal amplification (TSA) system. HRP accepts various fluorescently-labeled tyramide derivatives as substrates. The resulting tyramide radical product is highly reactive and forms covalent bonds with localized tyrosine and other aromatic amino acids, leading to a localized fluorescent signal at the sites of protein binding on the array.

In embodiments of the invention that employ a UPS reagent with an N-hydroxy succinimide group, the desired reaction of the NHS group (for example, reaction of a N-hydroxysuccinimide-activated dye with amine groups on protein) competes with hydrolysis of the NHS group. In order to minimize NHS hydrolysis, the NHS reagent is preferably stored in dry DMSO prior to dilution into aqueous buffer, and the diluted reagent is preferably used immediately after dilution. In addition, in preferred embodiments, a dry organic solvent such as dimethylformamide (DMF) may be included in the reaction, thereby allowing more efficient utilization of the NHS group, and consequently more efficient protein labeling. Non-nucleophilic organic bases such as DIEA (diisopropylethylamine) may also be included in the UPS reaction to catalyze the reaction of the lysine amine side chain with N-hydroxysuccinimidyl esters.

Organic solvents have strong protein denaturing properties, because of their ability to solubilize hydrophobic sidechains, and thus maximize the availability of protein sidechains to active UPS reagents that react with groups on those protein sidechains. The identity of the solvent also has large effects on the degree of staining of the solid support on which the nucleic acid ligand array is immobilized, depending on the characteristics of the surface layer of the solid support and properties of the solvent. Thus, in preferred embodiments of the invention, the UPS reaction(s) are carried out in the presence of an organic solvent(s) selected in least in part for its ability to suppress reactivity of the surface layer of the solid support with components of the UPS. For example, the surface reactivity of OptiChem surfaces on Accelr8 slides for NHS-activated dyes under aqueous conditions is suppressed in the polar aprotic organic solvents DMF or DMSO (possibly due to the dehydration and collapsing of the surface gel layer).

It will be appreciated by those skilled in the art that using organic solvents for the UPS reaction(s) according to the methods provided herein can lead to dramatic improvements in the labeling of proteins relative to the same reactions carried out in aqueous solution. Specifically, if a suitable organic solvent(s) is used for the UPS reaction(s), improvements in the stability of the UPS reagent(s), the availability of the protein sidechain groups, and in the suppression of reactivity of the solid support surface layer may be simultaneously realized. For example, the use of organic solvent in conjunction with a UPS comprising a NHS-activated-dye both increases the staining of the protein (by at least 10-fold due to the increased availability of amines in protein sidechains and due to the decreased hydrolysis of the NHS group) and decreases the staining of the slide surface (by approximately 5-fold), thus increasing the sensitivity of the staining protocol.

The sensitivity of a UPS can be limited by background signals due to reaction of the UPS with the surface of the solid support on which the array is immobilized, or with a small fraction of the DNA bases in nucleic acid ligand features. In some embodiments, the UPS includes a reagent that covalently reacts with amino acids, leading to the formation of a modified amino acid side chain that does not occur naturally. The UPS further comprises a reagent, preferably an antibody that binds to the modified amino acid, but not to the unmodified amino acid. The antibody may be directly conjugated to a detectable moiety, for example, a fluorophore or an enzyme. Alternatively, additional UPS reagents may be added to indirectly localize the detectable moiety to the bound antibody. For example, a fluorescently labeled secondary antibody that recognizes the first antibody may be used.

In one embodiment employing modified amino acids, the UPS comprises tetranitromethane (which nitrosylates tyrosine and other aromatic amino acids) and further comprises an anti-nitro tyrosine antibody. In another embodiment, the UPS comprises sulfo-NHS acetate (which acetylates lysine residues) and further comprises an anti-acetylated lysine antibody.

Examples of UPS reagents are provided in Example 3 and Example 4.

The UPS reagents described herein can be used to detect target protein binding to nucleic acid ligands, including photocrosslinking nucleic acid ligands and non-photocrosslinking nucleic acid ligands. Preferably, the UPS reagents are used to detect target protein binding to nucleic acid ligands that are immobilized on a solid support. In especially preferred embodiments, the UPS reagents are used to detect target protein binding to multiplexed arrays of nucleic acid ligands. In such arrays, target identity is determined by the position ("address") on the array to which protein binds. In some embodiments using multiplexed arrays, a single UPS can be used to detect the binding of hundreds or thousands of different target proteins.

EXAMPLES

The following examples are provided for illustrative purposes only and are not intended to limit the scope of the invention.

Example 1

Protocols for Arraying Photocrosslinking Nucleic Acid Ligands on a Solid Support The following description provides an exemplary and non-limiting method for arraying amine-terminated nucleic acid ligands, including photocrosslinking nucleic acid ligands, on a Surmodics N-hydroxy-succinimide-activated slide surface.

Photoaptamers are prepared for printing by making a 10 µM solution of each nucleic acid ligand in 150 mM $NaPO_4$ pH 8.5, 0.001% Sarkosyl. 15 µL of each aptamer are placed into wells of a 384 well microtiter plate. Controls include 30N12 random DNA, print buffer containing no DNA, and 30N12 random DNA+0.2 µM NH-Model-Cy3 for use as corner markers. The microtiter plate is centrifuged briefly to draw all materials to the bottoms of their wells, and the plate is ready for printing.

The printing process may be carried out using a commercial printer, such as a Packard Gene Array contact spotter according to the following procedure (contact spotter maintained at 22° C. and 62% RH):
1. Deposit ~1 nL droplets onto the slide in arrays.
2. Allow the droplets to incubate for several hours.
3. Soak the slides in post spotting solution (0.2M Tris HCl, 0.05M aspartic acid, pH 9.0, 0.1% SDS (added just prior to use)) for 60 min. at RT (18° C.).
4. Soak the slides in post spotting stabilization buffer (NaCl, Na-citrate, pH 7.0, 0.1% SDS (added just prior to use)) for 60 min. at 48° C.
5. Soak the slides in SELEX Buffer (40 mM HEPES, pH 7.5, 111 mM NaCl, 5 mM KCl, 1 mM $CaCl_2$, 1 mM $MgCl_2$, 0.05% Tween-20) for 30 min at RT (18° C.).
6. Rinse 5× for 1 min. with 300 mL deionized water each time.
7. Store the slides in a humid environment to prevent drying.

More preferably, the printing procedure may be carried out according to the following procedure:
1. Deposit ~1 nL spots into array format and allows the droplets to incubate on the surface for 2 hours.
2. Following the printing process, the residual functional groups on the surfaces are hydrolyzed by immersion in 20 mM NaOH, followed by 20 minutes of agitation and rinsing with $ddH_2O$.
3. The surfaces are then blocked with sulfo-NHS-Acetate at 0.2 mg/ml and incubated with agitation for 60 minutes, then rinsed with $ddH_2O$. This blocking step prevents staining of the slide surface with amine-reactive protein dyes.
4. Dry the slides under nitrogen gas.

The specific printing protocol varies for each surface used for nucleic acid ligand immobilization.

Example 2

Microbead Substrates

Microbeads are another substrate for nucleic acid ligand binding. Carboxy-derivatized beads are washed with NaOH, then activated with 250 mM EDC in 100 mM MES (2-(N-Morpholino)-ethanesulfonic acid) buffer at pH 6.0. The activated beads are then treated with 250 mM Sulfo-N-hydroxy-succinimide in 100 mM MES buffer at pH 6.0 for 3 hours at room temperature. The aptamer is coupled to the beads by addition of a solution of 10 µM 5'-amine nucleic acid ligand in 500 mM CTAB (hexadecyltrimethylammonium bromide), 2% PEG (8 kDa) in 100 mM bicarbonate buffer at pH 9.0. A variety of bead types has been used as substrates including beads derivatized with carboxy, amine, streptavidin, and epoxide functionality.

Example 3

Target Incubation, Photocrosslinking, and Detection with UPS

The following exemplary protocol allows the multiplexed detection of protein targets that have bound and become photocrosslinked to their cognate photocrosslinking nucleic acid ligand. The UPS in this example is the NHS-derivative of the fluorophore ALEXA 555 (Molecular Probes, Inc.); however, those skilled in the art will understand that this example is broadly applicable to other UPS reagents, and is not limited to NHS-derivatives.

1. Equilibrate slide with Dilution Buffer (1× SELEX buffer, 0.05% Tween, 150 µg/ml tRNA, 0.1 mg/ml casein), 15 minutes and remove solution
2. Add protein mixture prepared in appropriate sample matrix to array.
3. Incubate 1-2 hour, 30° C. in humid chamber, more preferably in a flow cell (300 µL volume, 3 mL/min flow rate).
4. Remove protein solution, add Dilution Buffer and incubate 5 min, room temp.
5. Crosslink slide with 308 nm light at 3 J/cm$^2$ (slide maintained moist during irradiation)
6. Wash slide:
   a. 1×SSPE+0.1% SDS: 15 min (20×SSPE=200 mM pH 7.4 $NaH_2PO_4$, 5 M NaCl and 20 mM EDTA)
   b. 20 mM NaOH: 5 min
   c. 3×$H_2O$ 5 min total, $N_2$ dry slide
7. Dilute Alexa 555 NHS in Carbonate buffer (0.1M Na-carbonate, pH 8.75, 1 mM EDTA, 0.1% Tween-20) to 0.01 mg/ml from 10 mg/ml stock
8. Add 1 ml/slide in humid chamber
9. Incubate 30 min RT
10. Wash in slide chamber with
    a. 0.1% SDS 15 min
    b. 20 mM NaOH 5 min
    c. 3×$dH_2O$ 5 min total, dry
11. Read in Array Worx in cy3 channel for Alexa 555

Example 4

Comparison of UPSs

Figure 3:
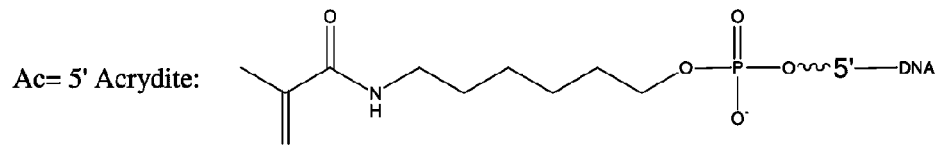
FIG. 3 provides sequences for the photocrosslinking nucleic acid ligands of the invention.
Figure 4:
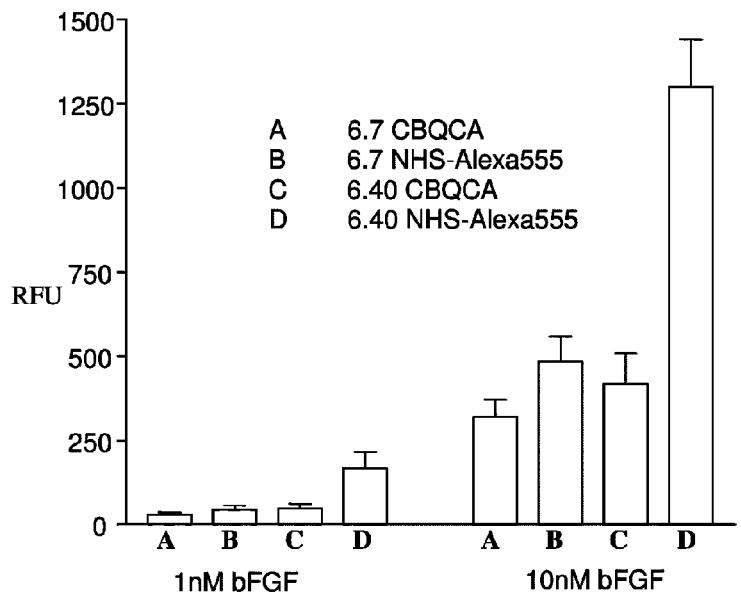
FIG. 4 depicts NHS-Alexa-555 staining compared with CBQCA staining for two different bFGF nucleic acid ligands at 1 nM bFGF and 10 nM bFGF.

Two different photocrosslinking nucleic acid ligands (6.7 and 6.40; see FIG. 3) recognizing bFGF (basic Fibroblast Growth Factor) were attached to the surface of Surmodics slides as described above in Example 1, and the slides contacted with bFGF at 1 nM and 10 nM concentrations. Crosslinking was initiated, and different UPSs were used to determine the level of bFGF binding according to Example 3. FIG. 4 depicts NHS-Alexa-555 staining compared with CBQCA staining for the two different bFGF nucleic acid ligands at 1 nM bFGF and 10 nM bFGF.

Figure 5:
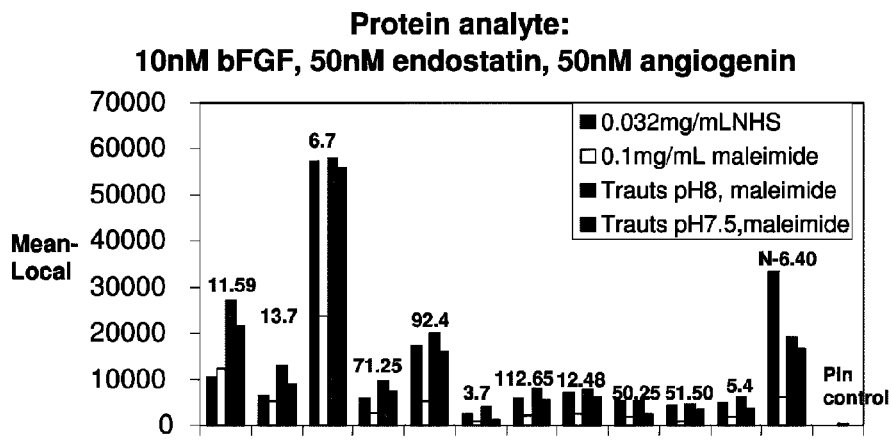
FIG. 5 illustrates comparisons between the target staining observed with photocrosslinking nucleic acid ligands to bFGF, angiogenin, and endostatin at specified concentrations of NHS-Alexa-555, maleimide-Alexa-555, and Traut's reagent followed by maleimide-Alexa-555 at two different pH values.

Using a Surmodics slide with photocrosslinking nucleic acid ligands to bFGF, angiogenin, and endostatin, additional UPS reagents were assayed. The target protein concentrations were 10 nM bFGF, 50 nM endostatin, and 50 nM angiogenin. FIG. 5 illustrates comparisons between the staining observed with specified concentrations of NHS-Alexa-555, maleimide-Alexa-555, and Traut's reagent followed by maleimide-Alexa-555 at two different pH values. The sequences of the photocrosslinking nucleic acid ligands are provided in FIG. 3.

Figure 6:
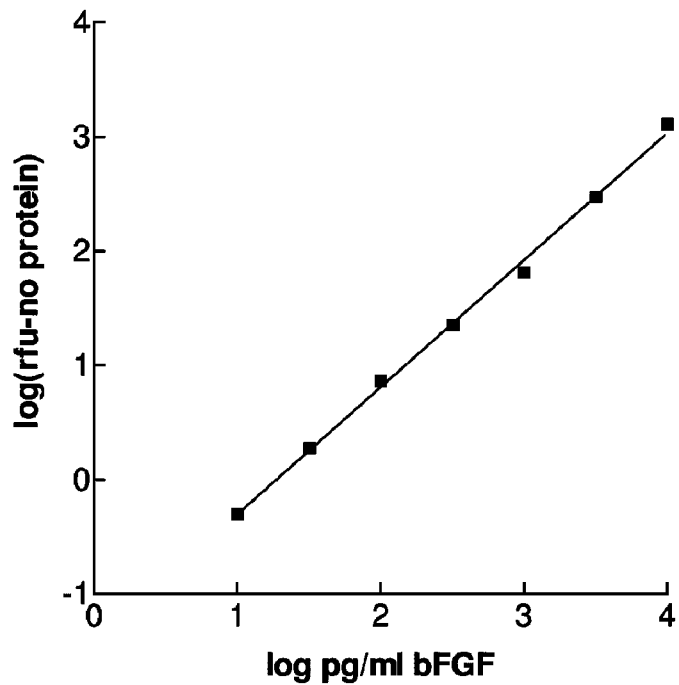
FIG. 6 depicts the results obtained using immobilized bFGF aptamer at different protein concentrations using an UPS comprising tetranitromethane/anti-nitro tyrosine antibody. Specifically, the graph plots log (pg/ml bFGF protein) against log (relative fluorescence units (RFU) in presence of protein–RFU in absence of protein).

Nitrosylation of tyrosine, followed by staining with a anti-nitrosylated tyrosine primary, then followed by staining with a fluorescent secondary antibody was also investigated as a UPS. FIG. 6 depicts the results obtained using immobilized bFGF aptamer at different protein concentrations. Specifically, the graph plots log (pg/ml bFGF protein) against log (relative fluorescence units (RFU) in presence of protein–RFU in absence of protein).

Example 5

Preparation of Vinyl-Sulfone-Peg Nucleic Acid Ligand Conjugates

The preparation of vinyl sulfone-PEG-nucleic acid ligand conjugates for several 5'amine-derivatized nucleic acid ligands (92.4, 328.43, 334.46, 71.25, 12.48, 6.40, 457.4, 311.37) is achieved by treating the nucleic acid ligand with 6 equivalents of the bifunctional NHS-PEG(3400 kDa)-vinyl sulfone (Shearwater) in 2 µL dry DMSO in a 10 uL aliquot of 100 mM borate buffer at pH 9.2 for 30 minutes. Conjugated nucleic acid ligands are purified on a pre-equilibrated ion exchange column (Q5 from Sartorius) to remove excess PEG reagent, then eluted with 1M NaCl, then desalted on a Sephadex G50 desalting column. The vinyl sulfone-PEG-nucleic acid ligands were printed onto thiol activated surfaces (Apogent).

Figure 7:
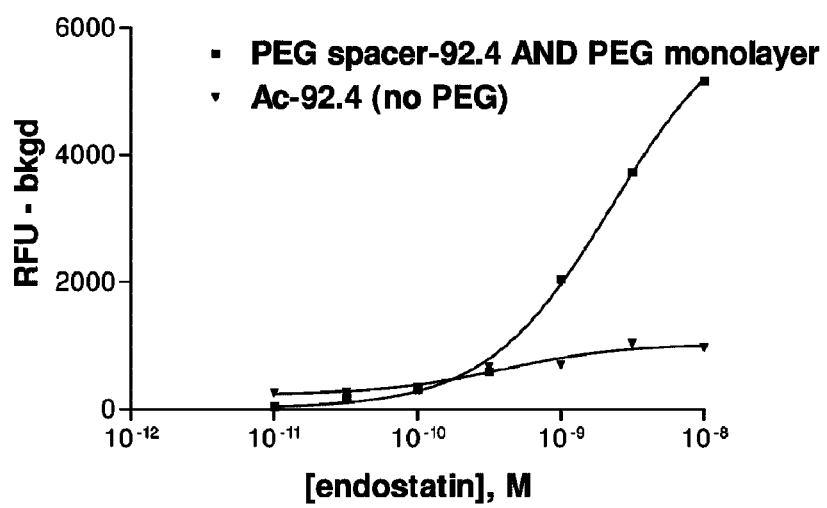
FIG. 7 depicts dose response curves for the specified proteins on an Apogent slide surface with nucleic acid microarrays. The two data sets contrast the activity of a photocrosslinking nucleic acid ligand to endostatin (92.4) with and without a PEG linker attachment. The data is plotted as the concentration of endostatin (M) against the corrected RFU (RFU-background).

FIG. 7 depicts dose response curves for the specified proteins on an Apogent slide surface with nucleic acid microarrays. The two data sets contrast the activity of a photocrosslinking nucleic acid ligand to endostatin (92.4) with and without a PEG linker attachment. The data is plotted as the concentration of endostatin (M) against the corrected RFU (RFU-background). It can be seen that the PEG linker enhances the protein binding activity of the 92.4 photocrosslinking nucleic acid ligand.

Example 6

Array of 67 Photocrosslinking Nucleic Acid Ligands

Sixty-seven photocrosslinking nucleic acid ligands to 25 different protein targets were arrayed according to the method of Example 1. Each photocrosslinking nucleic acid ligand was spotted in triplicate. The array also comprises the following addresses:

1. A fluorescent protein (fluorescently-labeled goat anti-rabbit antibody) in order to locate the arrays in the scanner;
2. Random DNA pools (30N12 DNA) in order to evaluate non-specific binding/labeling of DNA on the array;
3. Addresses that were contacted with hydroxy DNA (OH 6.7), rather than amine-modified DNA. Hydroxy DNA will not bind to the derivatized surface of the slide.
4. N-6.40 DNA. This amine-modified photocrosslinking nucleic acid ligand to basic fibroblast growth factor (bFGF) is found on the array at three different locations (each in triplicate). Since each address was spotted at a distinct time, this allows one to determine if photocrosslinking nucleic acid ligands that are spotted first on the array behave differently from those spotted later. The array layout is provided in FIG. 8 (each feature is present three times in succession).

Eight duplicate arrays were produced with this layout. The sequence of each photoaptamer on the array is provided in FIG. 3 ("N-" indicates the presence of a 5' amino-C6 linker used to attach each photoaptamer to the slide).

Protein mixtures were produced as detailed in Table 2 (which provides a key for the individual concentrations designated Level 1-8) and Table 3 (which shows the target protein concentration profiles (Level 1-8) in each of the individual target protein mixture (Tubes 1-8)).

TABLE 2

| Protein Level Range (moles/L) | | | | | | |
|---|---|---|---|---|---|---|
| Level 1 | Level 2 | Level 3 | Level 4 | Level 5 | Level 6 | Level 7 |
| 0 | 1E−11 | 3.16E−11 | 1E−10 | 3.16E−10 | 1E−09 | 1E−08 |

TABLE 3

Target Protein Concentration Profiles of
the Individual Target Protein Mixtures

|  | Tube 1 | Tube 2 | Tube 3 | Tube 4 | Tube 5 | Tube 6 | Tube 7 | Tube 8 |
|---|---|---|---|---|---|---|---|---|
| IL-4 | 5 | 2 | 3 | 8 | 4 | 1 | 7 | 6 |
| bFGF | 2 | 3 | 8 | 4 | 1 | 7 | 6 | 5 |
| Angiogenin | 3 | 8 | 4 | 1 | 7 | 6 | 5 | 2 |
| Endostatin | 8 | 4 | 1 | 7 | 6 | 5 | 2 | 3 |
| pSelectin | 4 | 1 | 7 | 6 | 5 | 2 | 3 | 8 |
| Serum Amyloid Protein | 1 | 7 | 6 | 5 | 2 | 3 | 8 | 4 |
| Thrombin | 7 | 6 | 5 | 2 | 3 | 8 | 4 | 1 |
| TGF-β1 | 6 | 5 | 2 | 3 | 8 | 4 | 1 | 7 |

Figure 9:
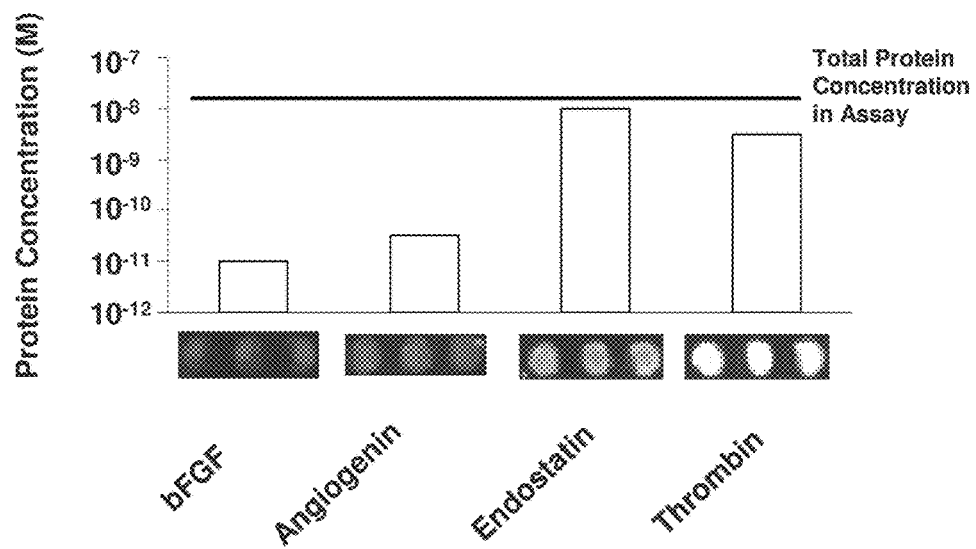
FIG. 9 depicts images taken from an array for bFGF, angiogenin, endostatin, and thrombin photocrosslinking nucleic acid ligands at the specified target concentrations.

FIG. 9 depicts images taken from an array for bFGF, angiogenin, endostatin, and thrombin photocrosslinking nucleic acid ligands at the specified target concentrations.

Figure 10:
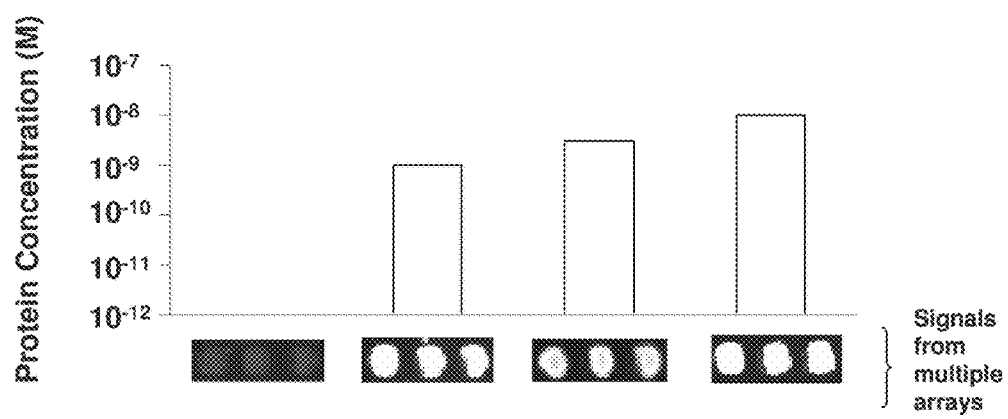
FIG. 10 depicts images from multiple arrays of the thrombin photocrosslinking nucleic acid ligand response. The data is used to provide the dose-response curve of the thrombin photocrosslinking nucleic acid ligand.

FIG. 10 depicts images from multiple arrays of the thrombin photocrosslinking nucleic acid ligand response. The data is used to provide the dose-response curve of the thrombin photocrosslinking nucleic acid ligand.

Figure 11:
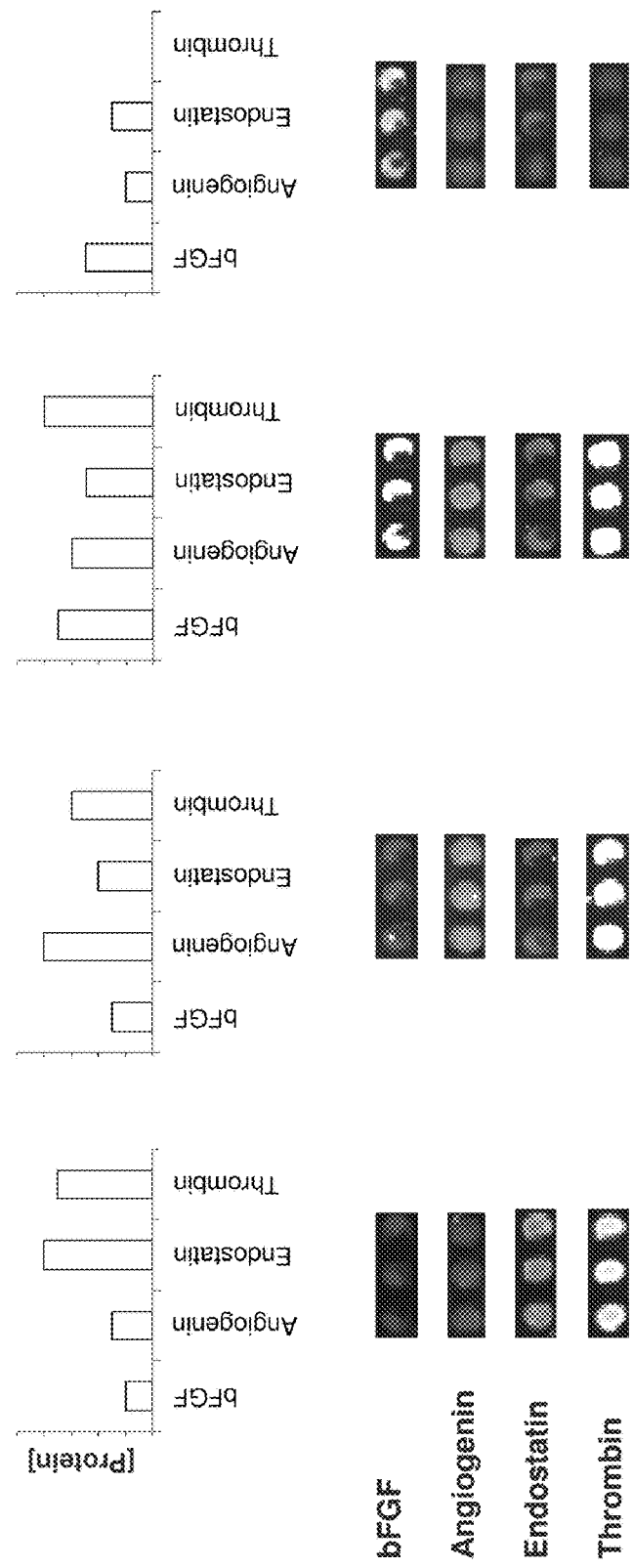
FIG. 11 depicts images of bFGF, angiogenin, endostatin, and thrombin photocrosslinking nucleic acid ligands from four duplicate arrays. The relative concentrations of each target protein are varied between the arrays as indicated by the graphs.

FIG. 11 depicts images of bFGF, angiogenin, endostatin, and thrombin photocrosslinking nucleic acid ligands from four duplicate arrays. The relative concentrations of each target protein are varied between the arrays as indicated by the graphs.

Figure 12:
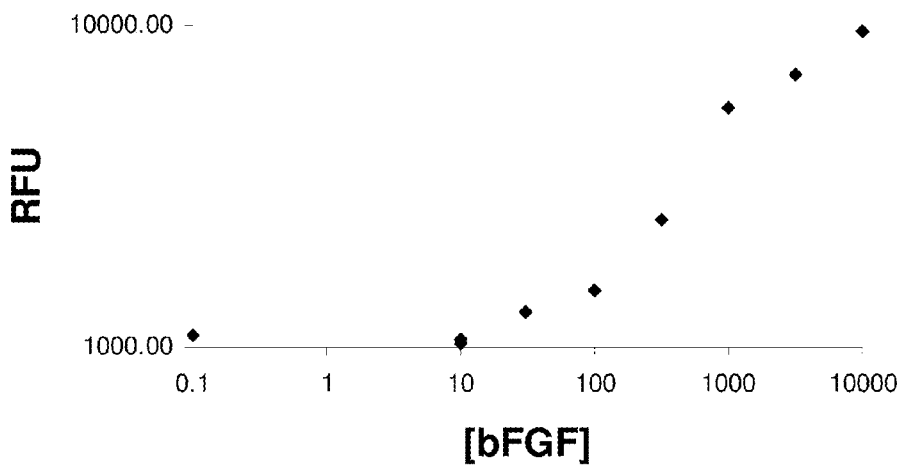
FIG. 12 depicts the bFGF photocrosslinking nucleic acid ligand binding curve derived from multiple arrays, each contacted with a different concentration of bFGF. The graph is a plot of the concentration of bFGF (nM) against RFU.

FIG. 12 depicts the bFGF photocrosslinking nucleic acid ligand binding curve derived from multiple arrays, each contacted with a different concentration of bFGF. The graph is a plot of the concentration of bFGF (pM) against RFU.

Example 7

Detection of HIV gp120MN in Serum

Figure 13:
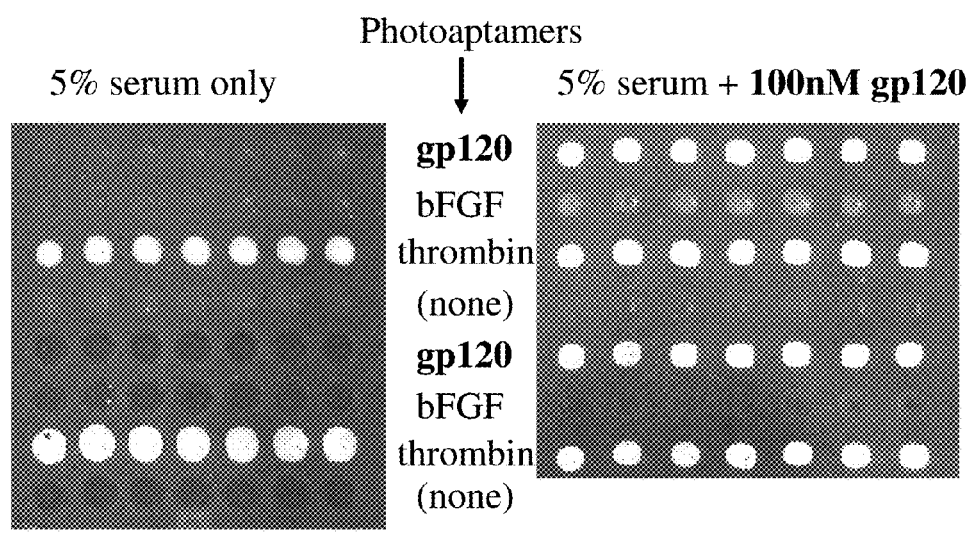
FIG. 13 illustrates arrays comprising photocrosslinking nucleic acid ligands to gp120MN, bFGF, and thrombin. One slide was incubated with 5% serum only; the other was incubated with 5% serum+100 nM gp120MN.

Using the techniques in Examples 1 and 3, photocrosslinking nucleic acid ligands to gp120MN, bFGF, and thrombin were arrayed on slides. One slide was incubated with 5% serum only; the other was incubated with 5% serum+100 nM gp120MN. FIG. 13 illustrates the resulting array signals. It can be seen that thrombin (present in serum) is detected in both, and that the gp120MN photocrosslinking nucleic acid ligand does not cross-react with any serum protein.

Example 8

Array of Photocrosslinking Nucleic Acid Ligands Directed Toward 14 Target Protein Analytes Arrays were printed onto slides according to Example 1. Each slide comprised eight duplicate arrays. Each photocrosslinking nucleic acid ligand was spotted four times in succession, giving a total of 96 photocrosslinking nucleic acid ligand features on each array. The layout of the array is given in FIG. 14. The sequences of the individual photocrosslinking nucleic acid ligands are provided in FIG. 3.

Protein mixtures containing 14 different proteins (endostatin, luciferase, thrombin, IL-4, tPA, catalase, C3, IL-8, von Willebrand Factor, bFGF, HIV gp120$_{MN}$, IGFBP-3, angiogenin, and VEGF) were produced. The protein mixtures were designed to test aptamer sensitivity and specificity. Eight protein mixtures were designed such that each protein is present at least once in excess of each of the other proteins in the mixture. The concentration range of the individual proteins was 10 pM-10 nM for the majority of the proteins. Three of the proteins (bFGF, HIV gp120$_{MN}$, and von Willebrand Factor) were present from 10 pM-2 nM because high concentrations caused some nonspecific reactions. The total added protein concentration in each mixture was approximately 25 nM. An example of the protein mixture multiplex design is given in Table 3 (which provides a key for the individual concentrations designated Level A-H) and Table 4 (which shows the target protein concentration profiles of the individual protein mixtures (Tubes 1-8)).

TABLE 3

Target Protein Concentration Key

| | Protein Level Range (moles/L) | | | | | | | |
|---|---|---|---|---|---|---|---|---|
| | Level A | Level B | Level C | Level D | Level E | Level F | Level G | Level H |
| bFGF, gp120, von Willebrand | 0.00E+00 | 1.00E−11 | 2.40E−11 | 5.80E−11 | 1.40E−10 | 3.40E−10 | 8.30E−10 | 2.00E−09 |
| All other proteins | 0.00E+00 | 1.00E−11 | 3.20E−11 | 1.00E−10 | 3.20E−10 | 1.00E−09 | 3.20E−09 | 1.00E−08 |

TABLE 4

Target Protein Concentration Profiles of
the Individual Target Protein Mixtures

| | Tube 1 | Tube 2 | Tube 3 | Tube 4 | Tube 5 | Tube 6 | Tube 7 | Tube 8 |
|---|---|---|---|---|---|---|---|---|
| gp120MN | E | B | C | H | D | A | G | F |
| bFGF | C | H | D | A | G | F | E | B |
| von Willerand | F | E | B | C | H | D | A | G |
| angiogenin | B | C | H | D | A | G | F | E |
| IL4 | H | D | A | G | F | E | B | C |
| Luciferase | D | A | G | F | E | B | C | H |
| tPA | A | G | F | E | B | C | H | D |
| C3 | G | F | E | B | C | H | D | A |
| IL8 | E | F | D | A | G | B | C | H |
| IGFBP3 | F | D | A | G | B | C | H | E |
| endostatin | D | A | G | B | C | H | E | F |
| VEGF | A | G | B | C | H | E | F | D |
| thrombin | G | B | C | H | E | F | D | A |
| catalase | B | C | H | E | F | D | A | G |

Protein mixtures were added to four sample matrices:
a. Human defibrinated/delipidated serum base matrix: Processed serum engineered to neutralize pathogen activity. This serum is depleted of globulins and much of the lipid content. Total serum protein for 5% base matrix is 3 mg/ml.
b. Urine: pooled male urine, total protein=90 μg/ml. Used at 50% dilution.
c. Tissue culture media: RPMI (Roswell Park Memorial Institute), no serum supplement. Used as 95% of the sample.
d. "Off the clot" (OTC) serum: Pooled human serum. The serum was diluted to 50% in SELEX buffer, filtered through a 300K molecular weight cutoff filter, and diluted to final concentration of 20%, which is 12 mg/ml total protein. The protein mixtures were added after serum filtration.

Each individual protein mixture (in sample matrix) was incubated with an array and processed according to the method of Example 3 using N-hydroxy-succinimide-Alexa-555 as the UPS. Thus, in total there were 32 different assay samples (each the eight protein mixtures in each of the four sample matrices). As each slide had eight duplicate arrays, the entire assay was carried out using only four slides, with each slide providing the dose response curve for 14 proteins targets in a particular sample matrix.

Figure 15:
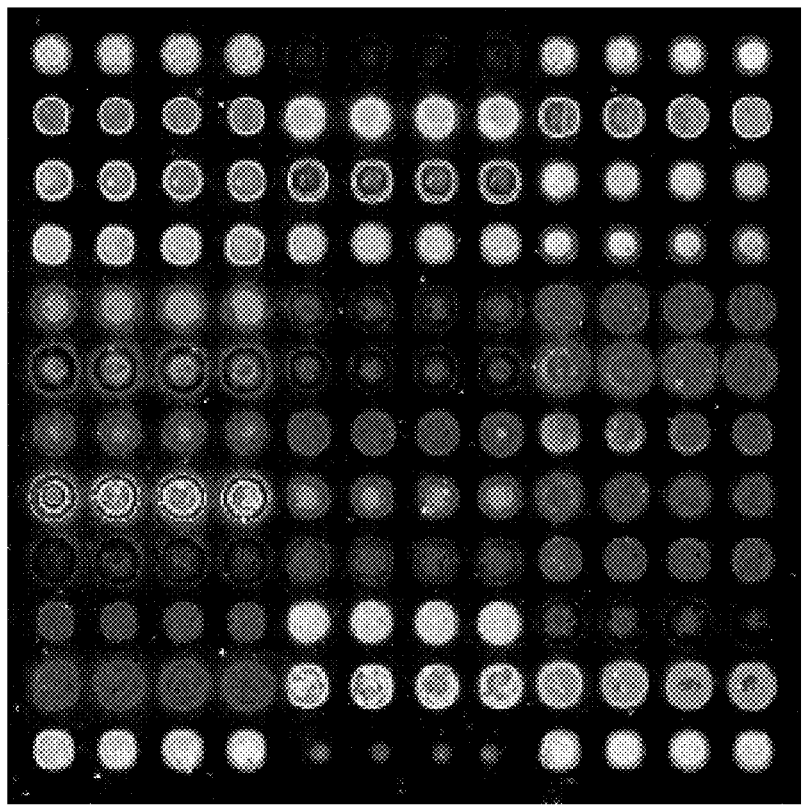
FIG. 15 depicts a fluorescent image of the array of FIG. 14 following incubation with cognate target proteins.

FIG. 15 depicts a fluorescent image of an array following incubation with cognate target proteins. All proteins could be detected at less than 1 nM concentration in 5% defibrinated/ delipidated serum base matrix or 50% urine or 95% tissue culture supernatant.

Figure 16:
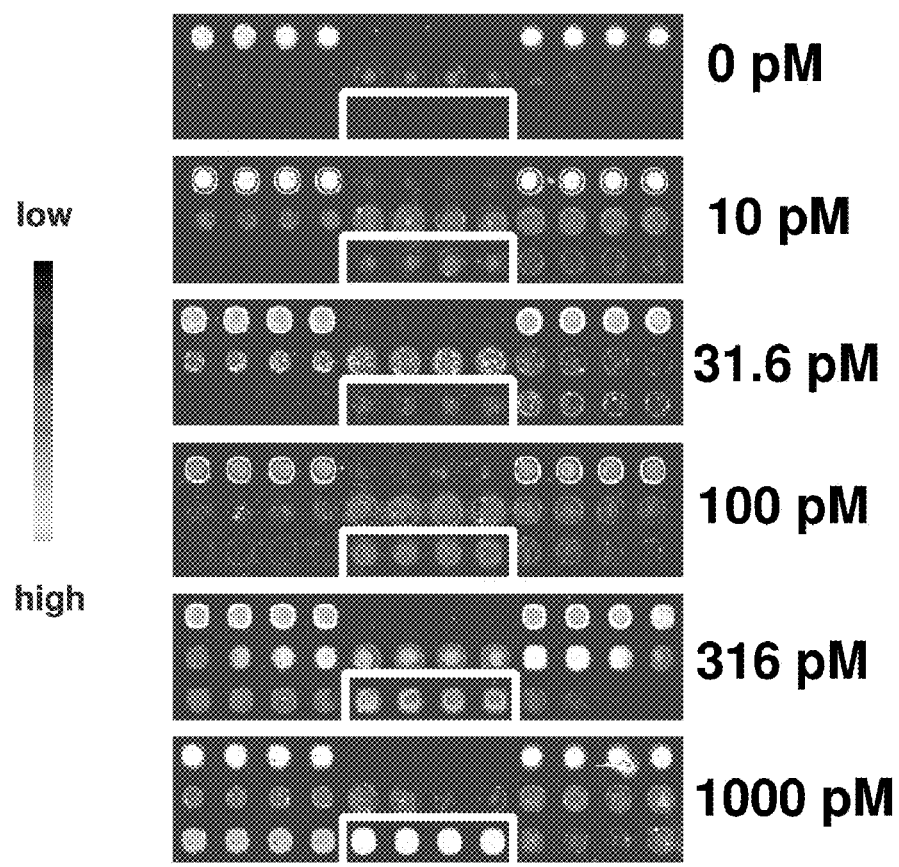
FIG. 16 provides images of an array showing the dose response profile of the endostatin nucleic acid ligand (0 pM-10,000 pM endostatin). The endostatin features on the array are delineated by a box.
Figure 17A:
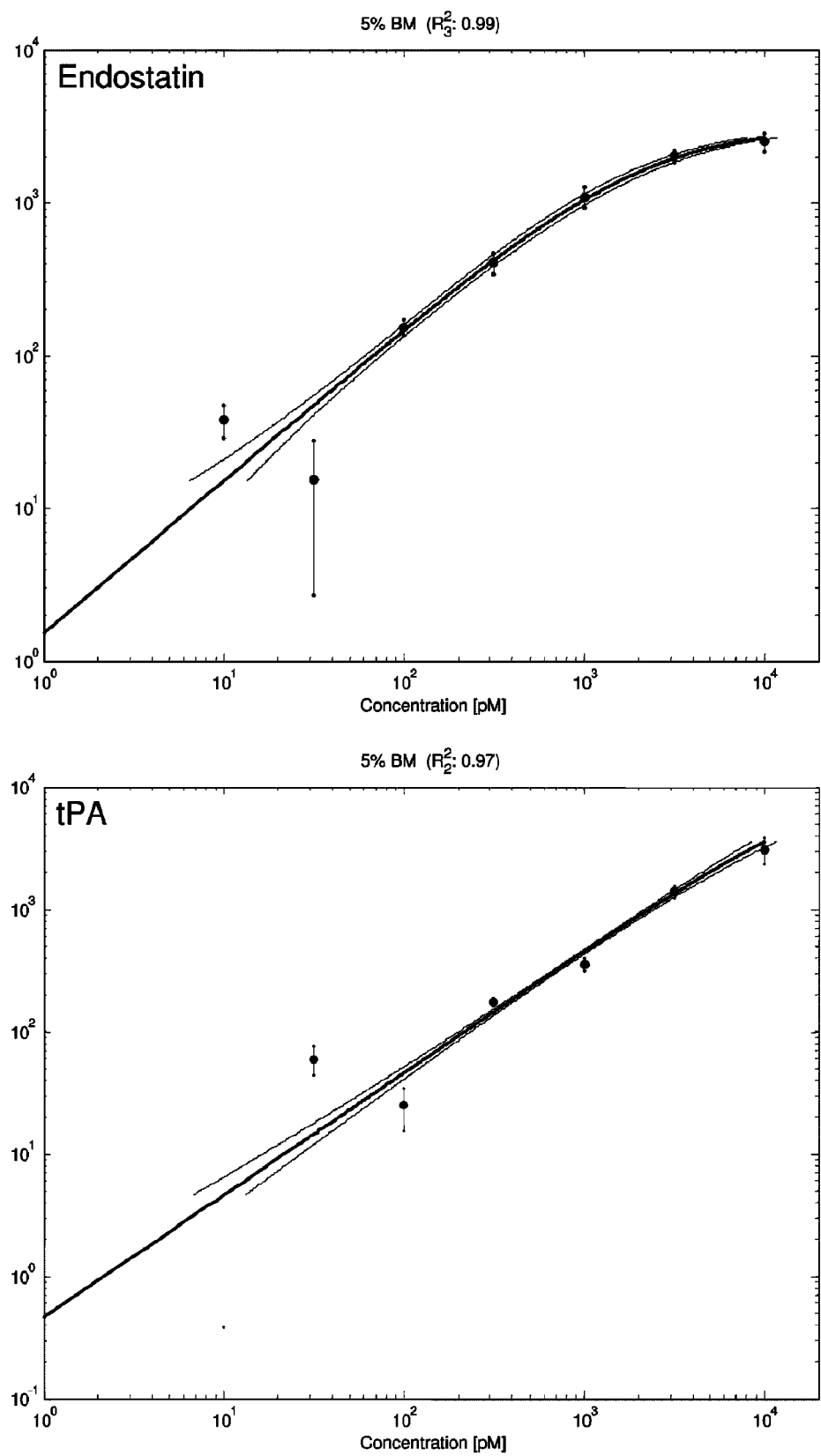
FIG. 17 provides dose response curves for 14 different target proteins in 5% defibrinated/delipidated human serum base matrix. Each plot shows the concentration of the protein target (pM) versus RFU.
Figure 17B:
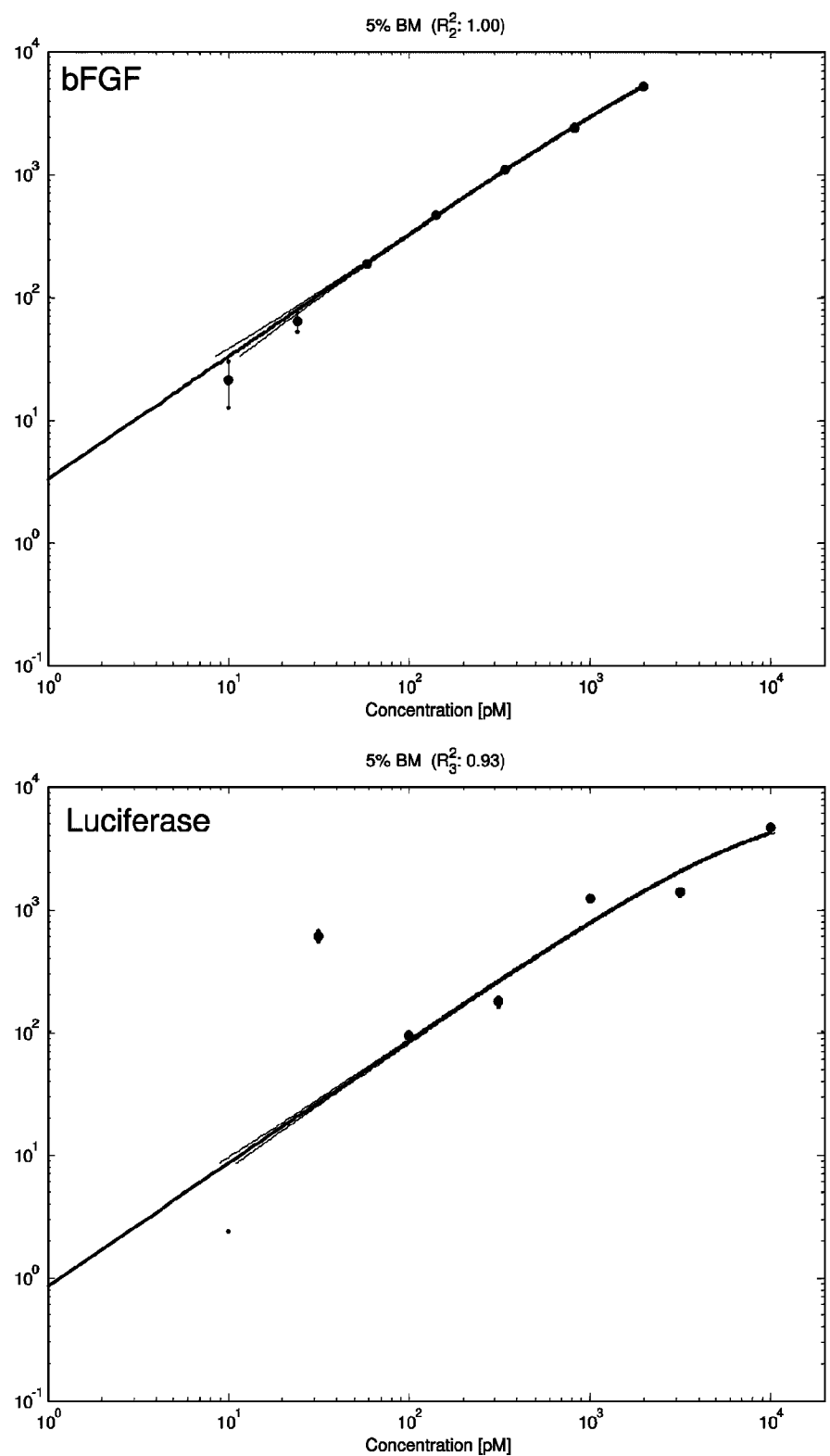
Figure 17C:
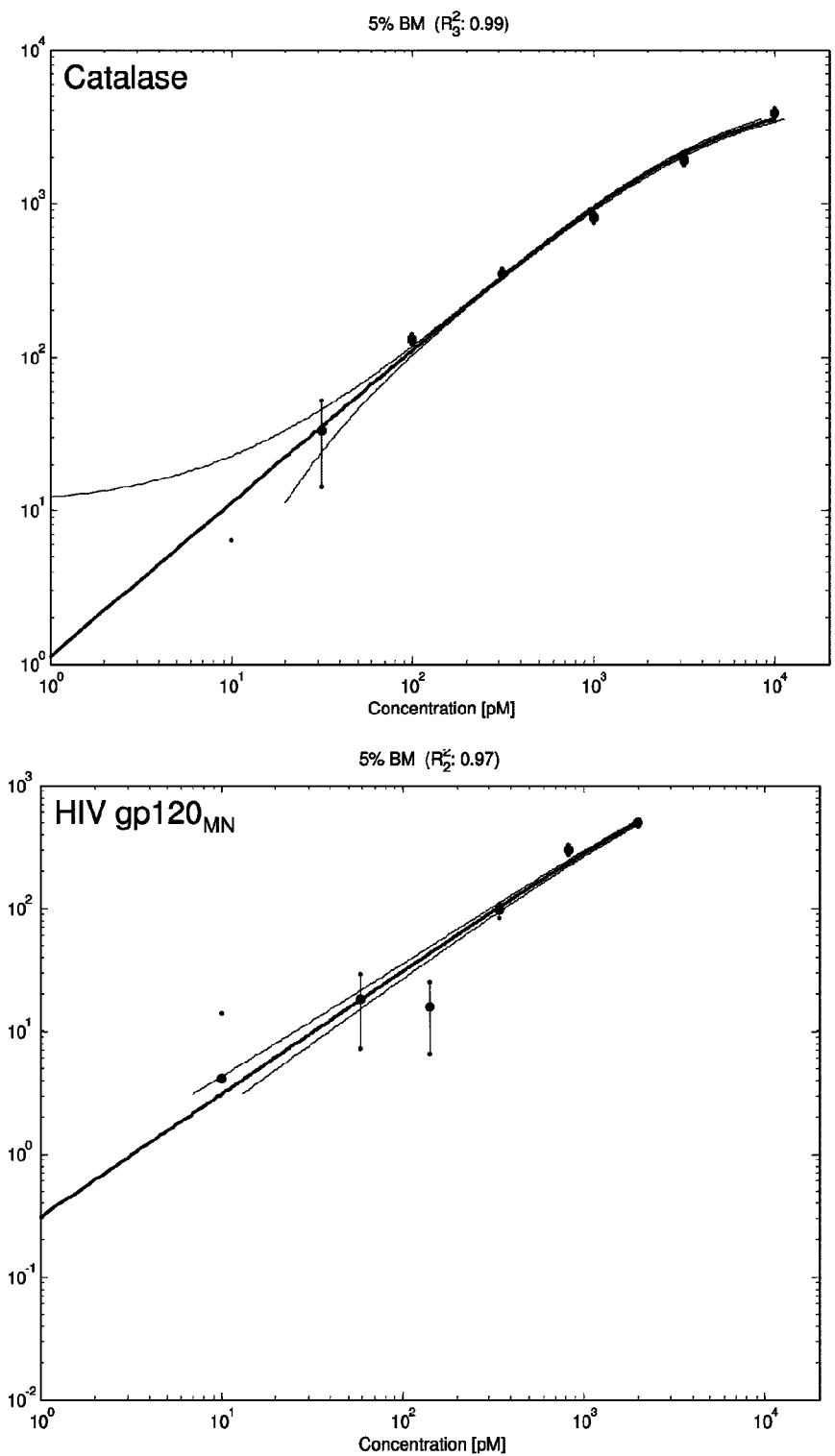
Figure 17D:
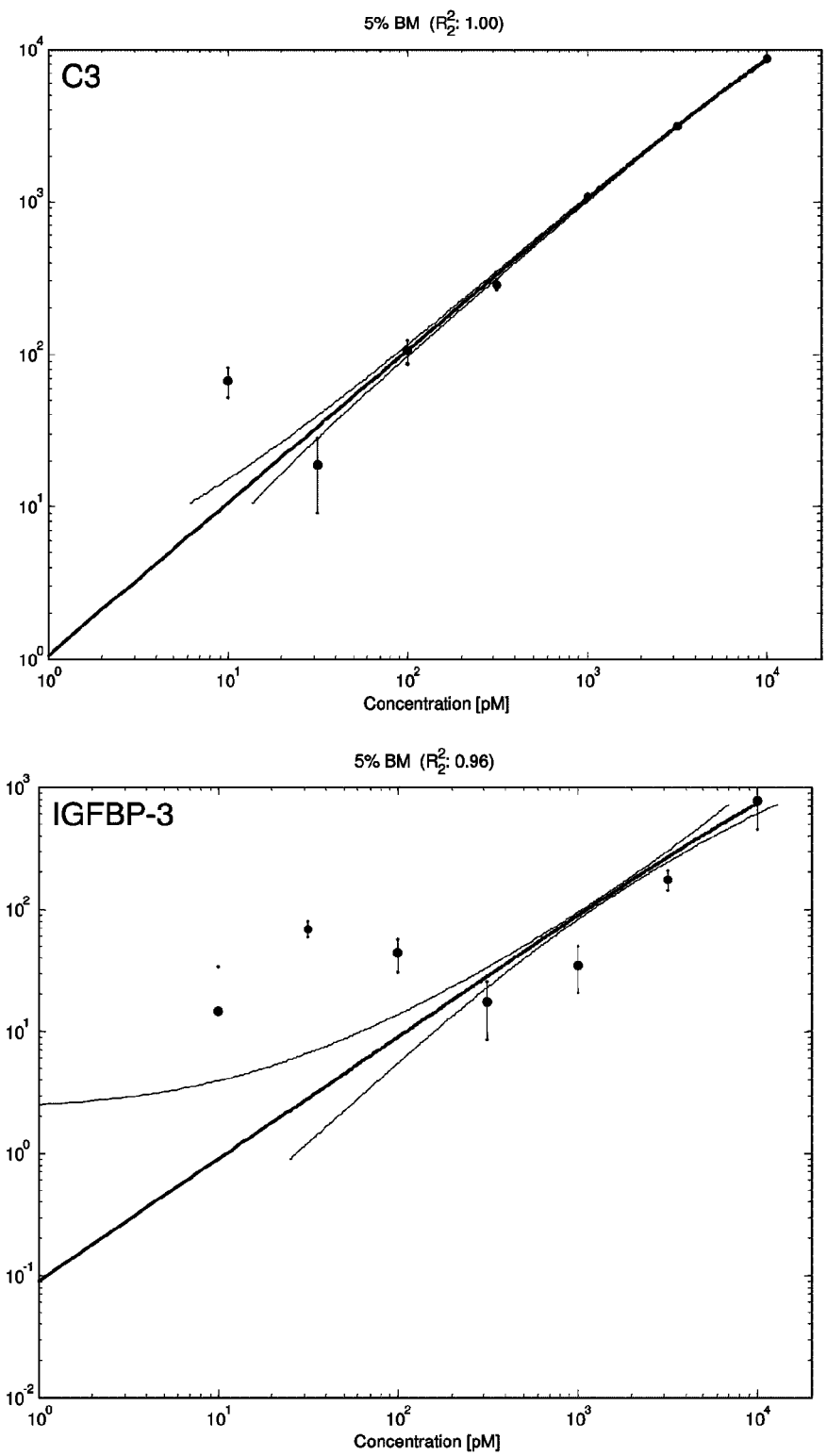
Figure 17E:
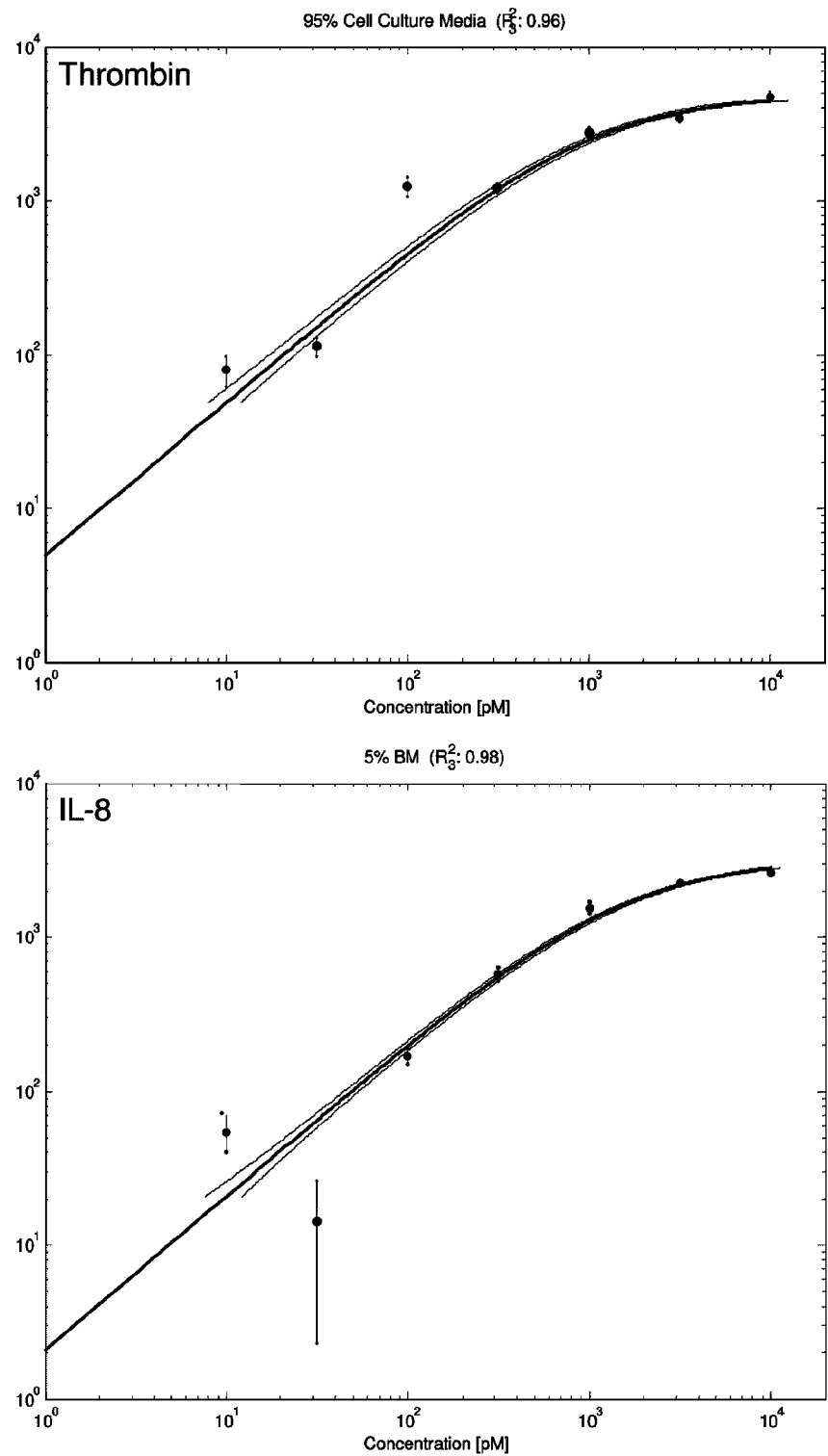
Figure 17F:
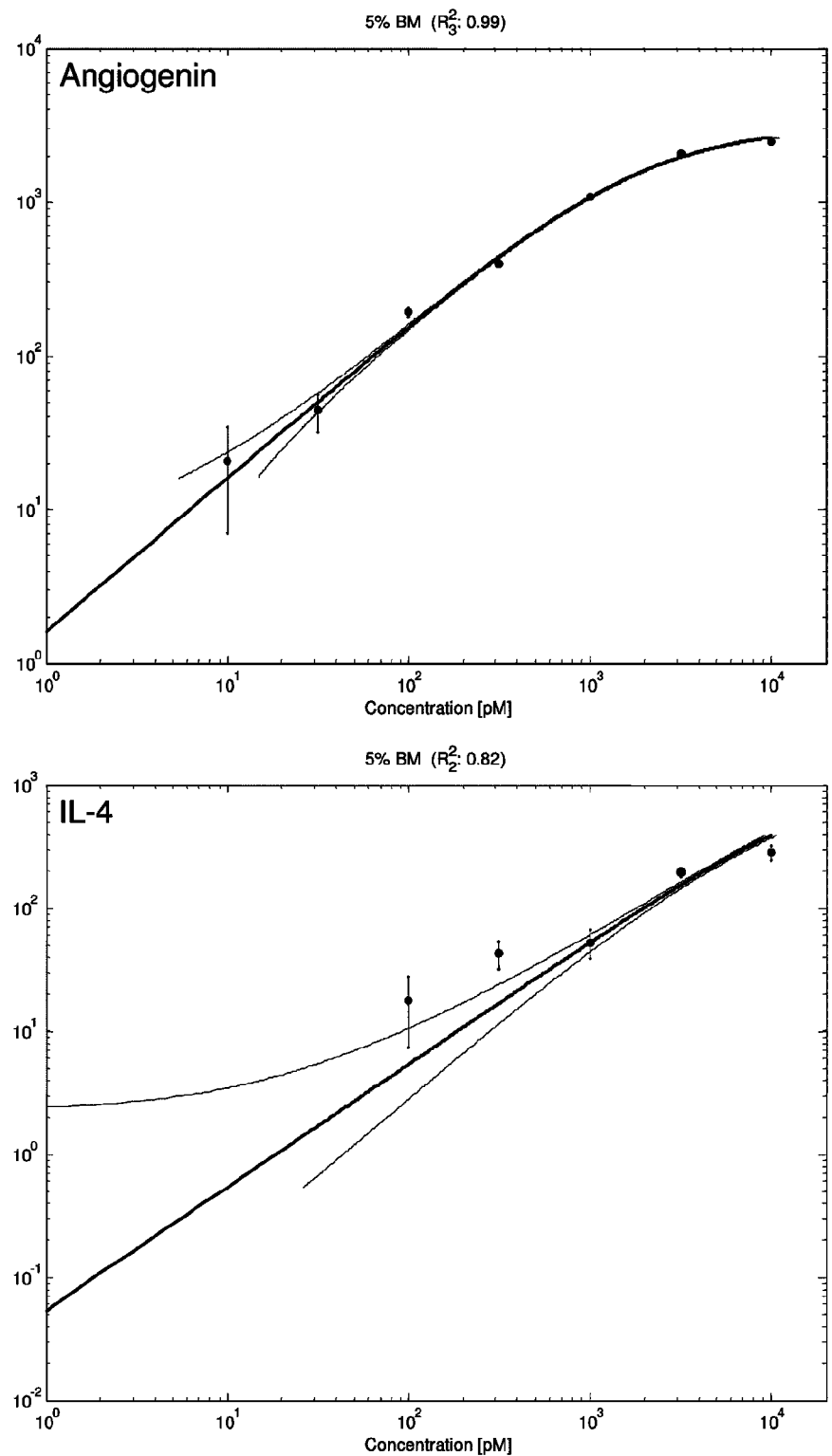
Figure 17G:
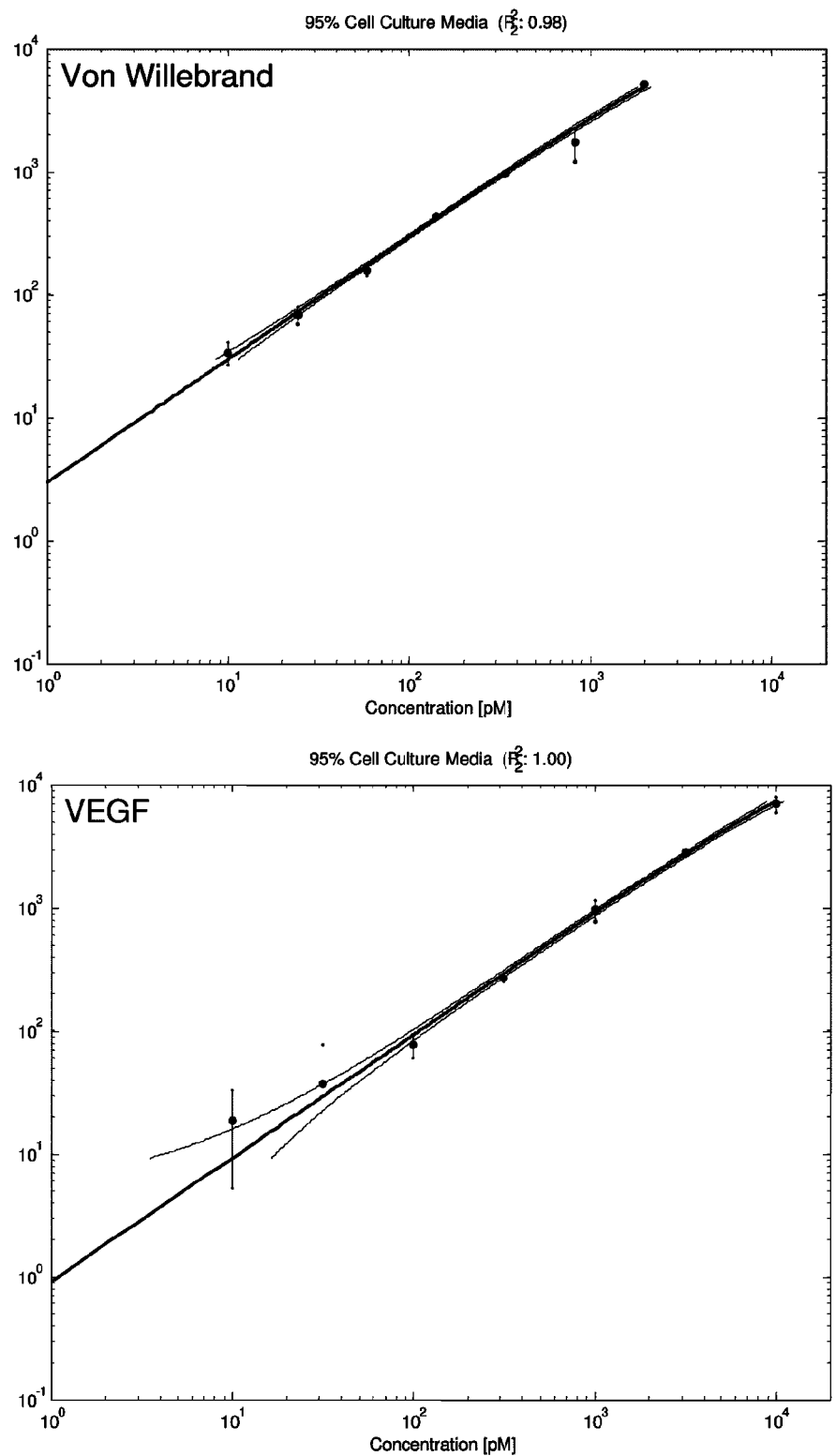

FIG. 16 provides images of the array showing the dose response profile of the endostatin nucleic acid ligand (0 pM-1, 000 pM endostatin). The endostatin features on the array are delineated by a box.

FIG. 17 provides dose response curves for the 14 different target proteins in 5% defibrinated/delipidated human serum base matrix. Each plot shows the concentration of the protein target (pM) versus RFU.

This example demonstrates that nucleic acid ligand microarrays can be used to measure specific protein concentrations in complex protein mixtures, including serum and urine specimens. Dose response curves were generated simultaneously to 14 proteins from 8 arrays printed on a single slide. The sensitivity and reproducibility of the photoaptamer arrays has been demonstrated by subnanomolar measurement of proteins in multiple sample matrices. The results demonstrate that photoaptamer arrays possess the qualities required for use in an analytical laboratory setting, namely: high throughput, ability to assay multiple analytes with consistent conditions, ability to use minimal sample volume (<100 μL), ability to provide reproducible results, and minimal matrix interference.

Example 9

Detection of Cognate Proteins in 5% Serum

Using the techniques in Examples 1 and 3, photocrosslinking nucleic acid ligands to bFGF, VEGF, endostatin, and catalase were arrayed on slides. Microarrays were exposed to 5% serum (filtered through a 0.2 micron filter to remove particulates, but without any other pretreatment) with some samples spiked with additional bFGF, VEGF, endostatin, and catalase in concentrations varying from 1 pM to 1 nM. The dose response for VEGF, endostatin, and catalase in the matrix of 5% serum is clear with minimal interference from the serum. The use of 5% serum in samples requires extensive harsh wash treatment following the UV photocrosslinking step defined as: 10 mM DTT, 0.1% SDS, 70 mM TRIS buffer at pH 11.0, and 500 mM NaCl flowing across the microarray for 30 minutes at 40° C. Nonfouling surfaces provided by Accelr8 and others yield the most definitive dose response curves in the presence of untreated serum. Dose response curves for VEGF, endostatin, and catalase in 5% serum on Accelr8 slide surfaces are shown in FIG. 18. The individual plots are of log [protein, M] versus log RFU.

Example 10

Detection of Cognate Proteins on Beads

Figure 19:
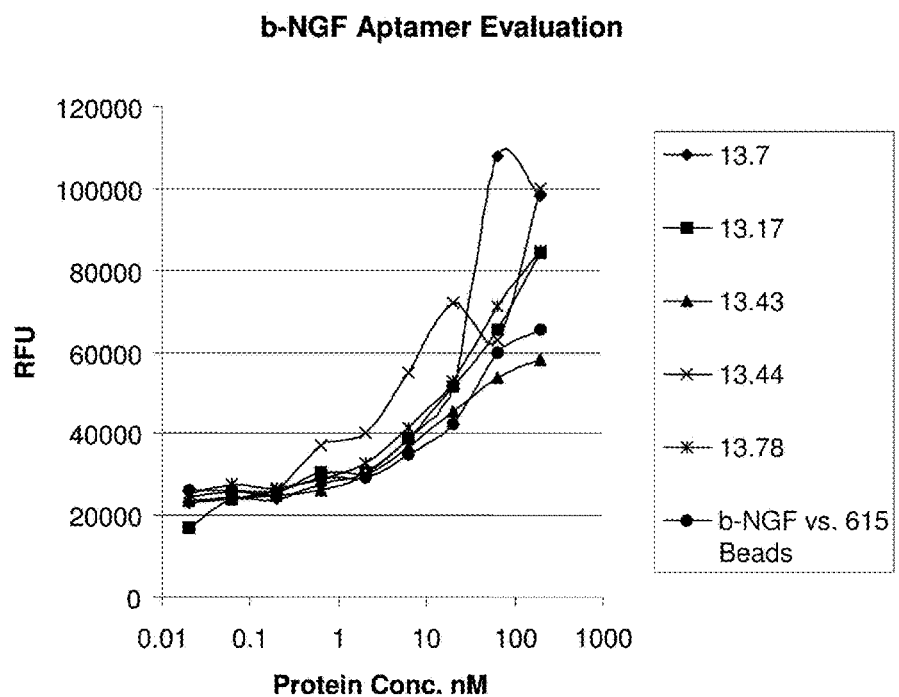
FIG. 19 depicts the protein binding curves for 5 unique nucleic acid ligands immobilized on beads to b-NGF as well as one noncognate aptamer.

When beads are loaded with nucleic acid ligands as described in Example 2, then exposed to cognate protein, dose response curves can be generated that are similar to those observed on flat surfaces. FIG. 19 depicts the protein binding curves for 5 unique nucleic acid ligands to b-NGF as well as one noncognate aptamer. Protein concentrations were tested from 10 pM to 100 nM. The noncognate nucleic acid ligand labeled 6.15 demonstrates the background signal for nonspecific protein binding. These binding curves can be used to rank the nucleic acid ligands for the greatest sensitivity and the lowest nonspecific background.

Example 11

Detection of Endogenous Serum Proteins

Figure 20:
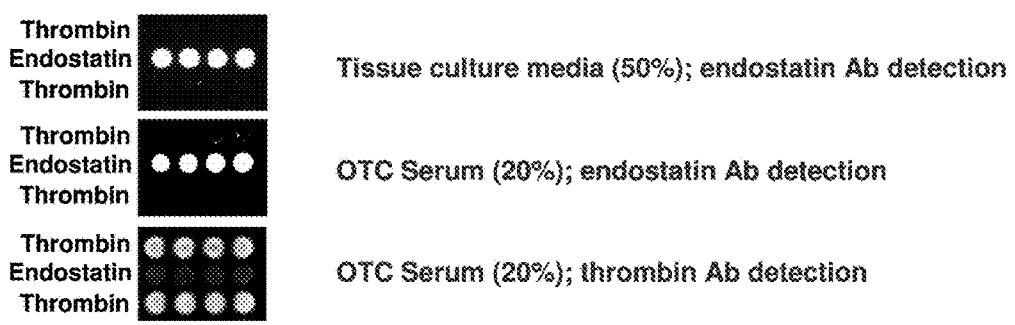
FIG. 20 illustrates the detection of endogenous thrombin and endostatin in tissue culture medium and 20% "Off the Clot" serum using endostatin and thrombin photocrosslinking nucleic acid ligands immobilized on solid supports.

In addition to detecting proteins spiked into serum, photocrosslinking nucleic acid arrays are able to detect endogenous levels of target proteins in test fluids such as serum or tissue culture supernatants. Samples of 1% serum, 5% delipidated serum, 50% serum base matrix or 50% filtered serum were added to arrays (produced according to Example 1), allowed to equilibrate, crosslinked, then washed under native conditions to avoid denaturing the captured proteins. Antibodies specific to endostatin and thrombin were allowed to bind to the captured proteins, and these antibodies were detected by use of an Alexa-555-labeled-anti-rabbit secondary antibody. The reaction of photoaptamers with endogenous protein in tissue culture supernatant or untreated serum was observed; no other photoaptamers on the array reacted with the endogenous proteins. See FIG. 20. Similar results were obtained for arrays treated with supernatant from an LnCAP tissue culture supernatant and labeled with anti-endostatin antibody.

What is claimed is:

1. A method for detecting the presence of a target molecule suspected of being contained in a test mixture, wherein said target molecule is a protein, the method comprising;
   a) providing a solid support, said solid support comprising a photoreactive nucleic acid ligand having specific affinity for said target protein, said photoreactive nucleic acid ligand binding specifically to said target molecule through non-Watson-Crick interactions;
   b) contacting said solid support with said test mixture suspected of containing said target molecule, wherein a nucleic acid ligand-target molecule complex is formed if said target molecule is present;
   c) irradiating said solid support, wherein said nucleic acid ligand-target molecule complex photocrosslinks;
   d) removing non-specifically bound material from said solid support;
   e) contacting said solid support with one or more reagents that label proteins with a detectable moiety; and
   f) detecting the presence of said target molecule by detecting the presence of said detectable moiety on said solid support.

2. The method of claim 1 wherein said step d) is accomplished by exposing said solid support to conditions that denature nucleic acids.

3. The method of claim 1 wherein step d) is accomplished by exposing said solid support to conditions that denature proteins.

4. The method of claim 1 wherein said detectable moiety is a dye.

5. The method of claim 4 wherein said dye is a fluorophore.

6. The method of claim 1 wherein said detectable moiety is an enzyme.

7. The method of claim 6 wherein said enzyme is alkaline phosphatase.

8. The method of claim 6 wherein said enzyme is horseradish peroxidase.

9. The method of claim 1 wherein said detectable moiety is an enzyme substrate.

10. The method of claim 1 wherein said detectable moiety is a radiolabel.

11. The method of claim 1 wherein at least one of said one or more reagents that label proteins with a detectable moiety reacts with primary amines.

12. The method of claim 11 wherein primary amine is present on a lysine residue.

13. The method of claim 11 wherein the reaction of at least one of said one or more reagents that label proteins with a detectable moiety with said primary amine occurs in the presence of an organic solvent.

14. The method of claim 1 wherein at least one of said one or more reagents that label proteins with a detectable moiety reacts with thiols.

15. The method of claim 1 wherein at least one of said one or more reagents that label proteins with a detectable moiety reacts with alcohols.

16. The method of claim 1 wherein at least one of said one or more reagents that label proteins with a detectable moiety reacts with carboxylates.

17. The method of claim 1 wherein said one or more reagents that label proteins with a detectable moiety comprises an N-hydroxysuccinimide-activated dye.

18. The method of claim 17 wherein said one or more reagents that label proteins with a detectable moiety comprises an N-hydroxysuccinimide-activated fluorophore.

19. The method of claim 1 wherein said one or more reagents that label proteins with a detectable moiety comprises CBQCA (3-(4-carboxybenzoyl) quinoline-2-carboxaldehyde).

20. The method of claim 1 wherein said one or more reagents that label proteins with a detectable moiety comprises a reagent that bears an amine reactive group selected from the list consisting of isocyanates, isothiocyanates, acyl azides, sulfonyl chlorides, aldehydes, 4-sulfo-2,3,5,6-tetrafluorophenol (STP) esters, NBD (7-nitrobenz-2-oxa-1, 3-diazole) chloride, NBD fluoride, and dichlorotriazines.

21. The method of claim 1 wherein said one or more reagents that label proteins with a detectable moiety comprises:
   a) a biotin derivative capable of reacting with primary amines; and
   b) a streptavidin conjugated to said detectable moiety.

22. The method of claim 1 wherein said one or more reagents that label proteins with a detectable moiety comprises:
   a) a first biotin derivative capable of reacting with primary amines;
   b) streptavidin; and
   c) a second biotin derivative conjugated to said detectable moiety.

23. The method of claim 1 wherein said one or more reagents that label proteins with a detectable moiety comprises:
   a) 2-iminothiolane; and
   b) a thiol-reactive derivative of a dye.

24. The method of claim 23 wherein said thiol-reactive derivative of said dye comprises a maleimide group.

25. The method of claim 1 wherein said one or more reagents that label proteins with a detectable moiety comprises:
   a) a hapten derivative capable of reacting with primary amines; and
   b) an anti-hapten antibody conjugated to said detectable moiety.

26. The method of claim 1 wherein said one or more reagents that label proteins with a detectable moiety comprises:
   a) a hapten derivative capable of reacting with primary amines;
   b) an anti-hapten antibody; and
   c) a secondary antibody conjugated to said detectable moiety, wherein said secondary antibody binds to said anti-hapten antibody.

27. The method of claim 1 wherein said one or more reagents that label proteins with a detectable moiety comprises:
   a) a reagent that modifies amino acid side chains;
   b) an antibody that specifically recognizes said modified amino acid side chain.

28. The method of claim 27 wherein said antibody is conjugated to said detectable moiety.

29. The method of claim 27 wherein said reagent that modifies amino acid side chains is a nitrosylating agent and wherein said antibody is an anti-nitro tyrosine antibody.

30. The method of claim 29 wherein said nitrosylating agent is tetranitromethane.

31. The method of claim 27 wherein said reagent that modifies amino acid side chains is a sulfo-N-hydroxysuccinimide acetate and wherein said antibody is an anti-acetylated lysine antibody.

32. A method for detecting the presence of a target molecule suspected of being contained in a test mixture, wherein said target molecule to be detected is a protein, the method comprising;
 a) providing a biochip comprising a solid support, said solid support comprising a plurality of spatially defined addresses, each said address comprising at least one copy of a single species of nucleic acid ligand attached thereto, each said species of nucleic acid ligand having specific affinity for one of said target molecules suspected of being contained in said test mixture, and each said species of nucleic acid ligand binding specifically to said target molecule through non-Watson-Crick interactions;
 b) contacting said biochip with said test mixture suspected of containing said target molecule;
 c) removing non-specifically bound material from said biochip;
 d) contacting said solid support with one or more reagents that label proteins with a detectable moiety; and
 e) detecting the presence of said target molecule by detecting the presence of said detectable moiety at the appropriate address on said biochip.

33. A method for detecting the presence of a target molecule suspected of being contained in a test mixture, wherein said target molecule is a protein, the method comprising;
 a) providing a solid support, said solid support comprising a nucleic acid ligand having specific affinity for said target protein, said nucleic acid ligand binding specifically to said target protein through non-Watson-Crick interactions;
 b) contacting said solid support with said test mixture suspected of containing said target molecule;
 c) removing non-specifically bound material from said solid support;
 d) contacting said solid support with one or more reagents that label proteins with a detectable moiety; and
 e) detecting the presence of said target molecule by detecting the presence of said detectable moiety at the appropriate address on said biochip.

34. A method for detecting the presence of a target molecule suspected of being contained in a test mixture, wherein said target molecule to be detected is a protein, the method comprising;
 a) providing a biochip comprising a solid support, said solid support comprising a plurality of spatially defined addresses, each said address comprising at least one copy of a single species of nucleic acid ligand attached thereto, each said species of nucleic acid ligand having specific affinity for one of said target molecules suspected of being contained in said test mixture, each said species of nucleic acid ligand binding specifically to said target molecule through non-Watson-Crick interactions, and wherein said nucleic acid ligand having specific affinity for said target molecule to be detected is a photoreactive nucleic acid ligand;
 b) contacting said biochip with said test mixture suspected of containing said target molecule, wherein a nucleic acid ligand-target molecule complex is formed if said target molecule is present;
 c) irradiating said biochip, wherein said nucleic acid ligand-target molecule complex photocrosslinks;
 d) removing non-specifically bound material from said biochip;
 e) contacting said biochip with a reagent that reacts covalently with proteins and not with nucleic acids; and
 f) detecting the presence of said target molecule by detecting the presence of said detectable moiety at the appropriate address on said biochip.

* * * * *